US008586579B2

(12) United States Patent
Gobbi et al.

(10) Patent No.: US 8,586,579 B2
(45) Date of Patent: Nov. 19, 2013

(54) ANELLATED PYRIDINE COMPOUNDS

(75) Inventors: Luca Gobbi, Muttenz (CH); Rosa Maria Rodriguez Sarmiento, Basel (CH); Juergen Wichmann, Steinen (DE)

(73) Assignee: Hoffmann-La Roche Inc., Nutley, NJ (US)

( * ) Notice: Subject to any disclaimer, the term of this patent is extended or adjusted under 35 U.S.C. 154(b) by 167 days.

(21) Appl. No.: 13/161,548

(22) Filed: Jun. 16, 2011

(65) Prior Publication Data
US 2011/0313151 A1  Dec. 22, 2011

(30) Foreign Application Priority Data
Jun. 21, 2010  (EP) .................................. 10166652

(51) Int. Cl.
A61K 31/496 (2006.01)
C07D 491/04 (2006.01)
C07D 495/04 (2006.01)

(52) U.S. Cl.
USPC ............... 514/228.2; 514/233.8; 514/253.04; 514/253.06; 544/58.2; 544/121; 544/362

(58) Field of Classification Search
None
See application file for complete search history.

(56) References Cited

U.S. PATENT DOCUMENTS

2010/0075985 A1  3/2010 Prior et al.

FOREIGN PATENT DOCUMENTS

| EP | 1870405 | 12/2007 |
|---|---|---|
| WO | 2007/148208 | 12/1997 |
| WO | 2006/082456 | 8/2006 |
| WO | 2007093540 | 8/2007 |
| WO | 2009019174 | 2/2009 |
| WO | 2010/031735 | 3/2010 |
| WO | 2010/034646 | 4/2010 |
| WO | 2010/034656 | 4/2010 |

OTHER PUBLICATIONS

Ashby et al., "Synapse" 48:154-156 ( 2003).
Mach et al., "ChemBioChem." (XP002650943), 5(4):508-518 ( 2004).
Howard et al., "Annual Reports in Medicinal Chemistry" 28:39 ( 1993), 39-47.
Vorel et al., "The Journal of Neuroscience" 22:9595-9603 ( 2002).
Moore et al., "European Journal of Pharmacology" 237:1-7 ( 1993).
Harrison et al., "British Journal of Psychiatry" 174(Suppl 38):12-22 ( 1999).
Levitan et al., "Journal of Affective Disorders" 71:229-233 ( 2002).
Gackenheimer et al., "Journal of Pharmacology & Experimental Therapeutics" 274:1558-1565 ( 1995).
Roth et al., "Nature Reviews & Drug Discovery" 3:353-359 ( 2004).
Drescher et al., "Am. Soc. Neurosci." 894:6 ( 2002), Abstract.
PCT International Search Report—PCT/EP2011/060080 Mailing Date Aug. 1, 2011.
Co-pending U.S. Appl. No. 13/171,499, filed Jun. 29, 2011.
Porras et al., "Neuropsychopharmacology" 26:311-324 ( 2002).
Retz et al., "Journal of Neural. Transmission" 110:531-572 ( 2003).
Arranz et al., "Lancet" 355:1615-1616 ( 2000).
Wiecki et al., "Psychopharmacology" 204:265-277 ( 2009).
PCT International Search Report—PCT/EP2011/061167—Mailed Sep. 22, 2011.
Spurlock et al., "Molecular Psychiatry" 3:42-49 ( 1998).
Belliotti, T. R., "Bioorganic & Medicinal Chemistry Lett." 7:2403 ( 1997).
Leikin et al., "Med. Toxicol. Adverse Drug Experiences" 4:324-350 ( 1989).
Joyce et al., "Drug Discovery Today" 10:917-925 ( 2005).
Campos et al., "Society for Neuroscience Abstract" 322:8 ( 2003).
Lieberman et al., "New England Journal of Medicine" 353:1209-1223 ( 2005).
Deangelis, L., "Current Opinion in Investigational Drugs" 3:106-112 ( 2002).
Gurevich et al., "ARchives of General Psychiatry" 54:225-232 ( 1997).
Millan et al., "The Journal of Pharmacology & Experimental Therapeutics" 324:1212-1226 ( 2008).
Reavill et al., "The Journal of Pharmacology & Experimental Therapeutics" 294:1154-1165 ( 2000).

Primary Examiner — Emily Bernhardt

(57) ABSTRACT

The present invention is concerned with novel dual modulators of the 5-$HT_{2A}$ and $D_3$ receptors of formula (I)

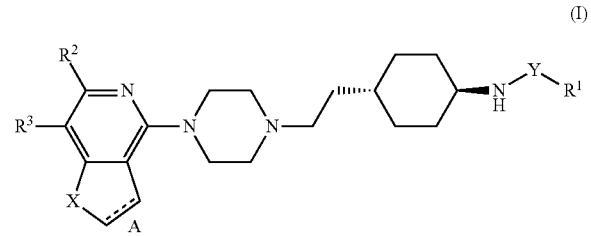

wherein X, Y, A, $R^1$, $R^2$, and $R^3$ are as described herein, as well as pharmaceutically acceptable salts and esters thereof. Further the present invention is concerned with the manufacture of the compounds of formula (I), pharmaceutical compositions comprising them and their use as therapeutics.

36 Claims, No Drawings

ANELLATED PYRIDINE COMPOUNDS

PRIORITY TO RELATED APPLICATION(S)

This application claims the benefit of European Patent Application No. 10166652.7, filed Jun. 21, 2010, which is hereby incorporated by reference in its entirety.

BACKGROUND OF THE INVENTION

In particular schizophrenia is characterized by complex symptomatology including positive symptoms, (i.e. delusions and hallucinations), and negative symptoms, (i.e. anhedonia, restricted fluency and productivity of thought and speech). In addition it is now well recognized that cognitive impairment is the third major diagnostic category of schizophrenia, characterized by loss in working memory as well as other deficits. Other symptoms include aggressiveness, depression and anxiety (Stahl, S. M., *Essential Psychopharmacology. Neuroscientific Basis and Practical Applications* (2000) $2^{nd}$ edition, Cambridge University Press, Cambridge, UK).

Dopamine, a major catecholamine neurotransmitter, is involved in the regulation of a variety of functions which include emotion, cognition, motor functions, and positive reinforcement. The biological activities of dopamine are mediated through G protein-coupled receptors (GPCRs) and in human, five different dopamine receptors $D_1$-$D_5$ have been identified, where the $D_2$-like receptors ($D_2$, $D_3$ and $D_4$) couple to the G-protein $G_{\alpha i}$. The $D_3$ dopamine receptor is most highly expressed in the nucleus accumbens and is proposed to modulate the mesolimbic pathway consisting of neuronal projections from the ventral tegmental area, hippocampus and amygdala to the nucleus accumbens, which projects to the prefrontal and cingulate cortices as well as various thalamic nuclei. The limbic circuit is thought to be important for emotional behavior and thus $D_3$ receptor antagonists are proposed to modulate psychotic symptoms such as hallucinations, delusions and thought disorder (Joyce J. N., Millan M. J., *Drug Discovery Today* (2005) 10:917-925). In addition, it has been reported that drug naive schizophrenic patients show altered levels of $D_3$ receptor expression (Gurevich E. V. et al., *Arch. Gen. Psychiatry* (1997) 54, 225-232) and dopamine release (Laruelle M, *Presentation at Institut de Recherches Internationales Servier Workshop on Schizophrenia: Pathological Bases and Mechanisms of Antipsychotic Action*, Chicago, Ill., 2000), indicating that a disturbed homeostasis of dopamine plays an important role in the etiology of schizophrenic symptoms.

The neurotransmitter serotonin (5-Hydroxytryptamine; 5-HT) is implicated in several psychiatric conditions including schizophrenia (Kandel E. R. et al. (eds.), *Principles of Neural Science* (2000) $3^{rd}$ edition, Appleton & Lange, Norwalk, Conn.). The involvement of serotonin in psychotic disorders is suggested by multiple studies which include treatment in humans with the psychotropic drug Lysergic acid (LSD; a serotonin agonist) which can induce schizophrenia-like symptoms such as hallucinations (Leikin J. B. et al., *Med. Toxicol. Adverse Drug Exp.* (1989) 4:324-350). Furthermore, altered brain distribution of serotonin receptors as well as an altered serotonergic tone, have been detected in schizophrenic patients (Harrison P. J., *Br. J. Psychiatry Suppl.* (1999) 38:12-22).

In mammals, serotonin exerts its biological activities through a family of 14 5-HT GPCRs. The 5-$HT_{2A}$ receptor is most prominently expressed in the prefrontal cortex and at lower levels in the basal ganglia and the hippocampus in human brain, and is coupled predominantly to the G-protein $G\alpha q$. Genetic linkage studies of a 5-$HT_{2A}$ polymorph to schizophrenia (Spurlock G. et al., *Mol. Psychiatry.* (1998) 3:42-49), as well as responsiveness to antipsychotic drugs (Arran, M. J. et al., *Lancet* (2000) 355:1615-1616), further suggest a role for the 5-$HT_{2A}$ receptor both in the treatment and pathology of psychosis. In addition, dopaminergic neurotransmission appears to be under the afferent regulation of the 5-$HT_{2A}$ receptor (Porras G. et al., *Neuropsychopharmacology* (2002) 26:311-324). Overall 5-$HT_{2A}$ receptor antagonists are proposed to be suitable for the treatment of disorders associated with dysfunctional dopaminergic systems. Moreover, 5-$HT_{2A}$ receptor antagonism has been recognized as beneficial for the treatment of psychosis (de Angelis L., *Curr. Opin. Investig. Drugs* (2002) 3:106-112).

The $D_3$ and 5-$HT_{2A}$ receptors besides the mentioned psychotic disorders are further reported to be linked to other psychoses including paranoia and delusions (Reavill C. et al., *JPET* (2000) 294:1154-1165; Harrison P. J., *Br. J. Psychiatry Suppl.* (1999) 38:12-22), to drug dependency, abuse and withdrawal (Voxel S. R. et al., *J. Neurosci.* (2002) 22:9595-9603; Campos A. C. et al., *Soc. Neurosci. Abstr.*, (2003) 322:8; Ashby C. R. et al., *Synapse* (2003) 48:154-156), attention deficit hyperactivity disorders (ADHD) (Retz W. et al., *J. Neural. Transm.* (2003) 110:531-572; Levitan R. D. et al., *J. Affective Disorder* (2002) 71:229-233), as well as to anxiety and depression (Reavill C. et al., *JPET* (2000) 294:1154-1165; Drescher K. et al. *Am. Soc. Neurosci.* (2002) 894:6).

Currently used medications to treat schizophrenia, bipolar mania and other psychoses, include both typical ($D_2$/$D_3$ preferring) or the more recent atypicals, which exhibit polypharmacology interacting at multiple receptors (e.g., $D_1$, $D_2$, $D_3$, $D_4$, 5-$HT_{1A}$, 5-$HT_{2A}$, 5-$HT_{2C}$, $H_1$, $M_1$, $M_2$, $M_4$, etc.)(Roth B. L. et al., *Nat. Rev. Drug Discov.* (2004) 3:353-359). These antipsychotics, although relatively successful (some patients exhibit treatment resistance) at treating the positive symptoms of schizophrenia, are less effective at treating negative symptoms, cognitive deficits, and associated depression and anxiety, all of which lead to reduced patient quality of life and socioeconomic problems. Furthermore, patient compliance is compromised by prevalent side effects such as weight gain, extrapyramidal symptoms (EPS), and cardiovascular effects (Lieberman J. A. et al., *N. Engl. J. Med.* (2005) 353:1209-1223).

Antipsychotic drug treatment has frequently been complicated by serious side effects of widespread $D_2$ antagonism, notably an extrapyramidal or parkinsonian syndrome caused by antagonism of the dopaminergic projection from substantia nigra to corpus striatum. $D_2$ receptor blockade induces catalepsy and has been associated with negative effects against cognition. Also preferential blockade of $D_3$ vs. $D_2$ receptors, preserves and/or enhances cognitive function, and increases frontocortical cholinergic transmission. (Joyce J. N., Millan M J., *Drug Discovery Today* (2005) 10:917-925, Moore N. A. et al., *European Journal of Pharmacology* (1993) 237:1-7; Barth V. N., *Typical and atypical antipsychotics: Relationships between rat in vivo dopamine D(2) receptor occupancy assessed using LC/MS and changes in neurochemistry and catalepsy. Dissertation Indiana University* (2006); Millan M. J. et al., *Fr. Journal of Pharmacology and Experimental Therapeutics* (2008) 324:1212-1226; Wiecki T. V. et al., *Psychopharmacology* (2009) 204:265-277).

The typical antipsychotic agents on the market today display $D_2$ antagonism, and most have extrapyramidal side effects (EPS) such as pseudoparkinsonism and tardive dyskinesia (Howard H. R., Seeger T. F., *Annual Reports in Medici-* nal *Chemistry* (1993) 28:39). It has been shown by selective binding experiments that $D_2$ receptors are more concentrated in the striatal regions of the brain, which are responsible for locomotor control than in the limbic regions which are responsible for thought processes. $D_3$ receptors are more concentrated in the limbic than in the striatal regions. It is therefore believed that selective $D_3$ ligands may relieve symptoms of schizophrenia without causing the EPS associated with blockade of $D_2$ receptors (Gackenheimer S. L. et al., *J. Pharmacol. Exp. Ther.* (1995) 274:1558, Belliotti T. R., *Bioorg. Med. Chem. Lett.* (1997) 7:2403).

SUMMARY OF THE INVENTION

The present invention provides dual modulators of the $5\text{-HT}_{2A}$ and $D_3$ receptors, their manufacture, pharmaceutical compositions comprising them and their use as therapeutics.

In particular, the present invention provides compounds of formula (I)

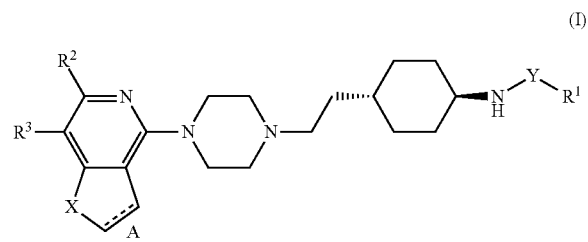

wherein
X is O or S;
Y is —C(O)— or —S(O)$_2$—;
A is a single bond or double bond,
  with the proviso that when X is S then A is a double bond;
$R^1$ is hydrogen, $C_{1-7}$ alkyl, $C_{1-7}$ haloalkyl, $C_{2-7}$ alkenyl, $C_{2-7}$ alkynyl, cycloalkyl, heterocycloalkyl, aryl, aryl annellated to heterocycloalkyl, heteroaryl, or —N($R^6$)$_2$, wherein $C_{1-7}$ alkyl, $C_{1-7}$ haloalkyl, $C_{2-7}$ alkenyl, $C_{2-7}$ alkynyl are optionally substituted by one to three substituents selected independently from the group consisting of cyano, cycloalkyl, heterocycloalkyl, aryl, aryl annellated to heterocycloalkyl, heteroaryl, —C(O)N($R^6$)$_2$, —N($R^6$)$_2$, —NH(CO)—$C_{1-7}$ alkyl, hydroxy, $C_{1-7}$ alkoxy, $C_{1-7}$ haloalkoxy, oxo, and —S(O)$_2R^7$, and wherein cycloalkyl, heterocycloalkyl, aryl, aryl annellated to heterocycloalkyl and heteroaryl are optionally substituted by one to three independent $R^4$;
$R^2$ and $R^3$ are each independently hydrogen, halogen, $C_{1-7}$ alkyl, $C_{1-7}$ haloalkyl, hydroxy, $C_{1-7}$ alkoxy or $C_{1-7}$ haloalkoxy;
$R^4$ is halogen, cyano, $C_{1-7}$ alkyl, $C_{1-7}$ haloalkyl, cycloalkyl, heterocycloalkyl, aryl, aryl annellated to heterocycloalkyl, heteroaryl, —C(O)N($R^6$)$_2$, —N($R^6$)$_2$, —NH(CO)—$C_{1-7}$ alkyl, hydroxy, $C_{1-7}$ alkoxy, $C_{1-7}$ haloalkoxy, oxo, —S(O)$_2$ $R^7$, or $C_{1-7}$ alkyl substituted by one to three substituents selected independently from the group consisting of cyano, hydroxy, $C_{1-7}$ alkoxy, and $C_{1-7}$ haloalkoxy, wherein cycloalkyl, heterocycloalkyl, aryl, and heteroaryl are optionally substituted by one to three independent $R^5$;
$R^5$ is halogen, cyano, $C_{1-7}$ alkyl, $C_{1-7}$ haloalkyl, hydroxy, $C_{1-7}$ alkoxy, $C_{1-7}$ haloalkoxy, or oxo;
$R^6$ is hydrogen or $C_{1-7}$ alkyl; and
$R^7$ is hydrogen, $C_{1-7}$ alkyl, or aryl, wherein aryl is optionally substituted by one to three independent $R^5$;
and pharmaceutically acceptable salts and esters thereof.

The compounds of the invention and their pharmaceutically acceptable salts have high affinity and selectivity for both, the dopamine $D_3$ and serotonin $5\text{-HT}_{2A}$ receptors and are effective, alone or in combination with other drugs, in the treatment or prevention of psychotic disorders, as well as other diseases such as depression, anxiety, drug addiction, attention deficit hyperactivity disorders, dementia and memory impairment, while exhibiting fewer associated side effects. Psychotic disorders encompass a variety of diseases, which include schizophrenia, positive, negative and/or cognitive symptoms associated with schizophrenia, schizoaffective disorders, bipolar disease, mania, psychotic depression, and other psychoses involving paranoia and delusions.

The current invention provides compounds with high affinity and improved selectivity for $D_3$ and $5\text{-HT}_{2A}$ receptors as well as methods for the treatment of psychoses and other diseases, with fewer associated side affects. The compounds of the invention are dual modulators of the $5\text{-HT}_{2A}$ and $D_3$ receptors and are selective at the $D_2$ receptor.

DETAILED DESCRIPTION OF THE INVENTION

The definitions described herein apply irrespective of whether the terms in question appear alone or in combination. It is contemplated that the definitions described herein may be appended to form chemically-relevant combinations, such as "heterocycloalkyl-aryl," "aryl-$C_{1-7}$ alkyl-heterocycloalkyl," "$C_{1-7}$ alkoxy-$C_{1-7}$ alkyl," and the like.

The singular forms "a", "an," and "the" include plural referents unless the context clearly dictates otherwise, e.g. a compound refers to one or more compounds or at least one compound.

The term "substituted" denotes that a specified group or moiety can bear 1, 2, 3, 4, 5 or 6 substituents. Where any group can carry multiple substituents and a variety of possible substituents is provided, the substituents are independently selected and need not to be the same. When indicating the number of substituents, the term "one or more" refers to the range from one substituent to the highest possible number of substitution, i.e. replacement of one hydrogen up to replacement of all hydrogens by substituents. The term "unsubstituted" means that the specified group bears no substituents. The term "optionally substituted" means that the specified group is unsubstituted or substituted by one or more substituents, independently chosen from the group consisting of possible substituents.

The term "optional" or "optionally" denotes that a subsequently described event or circumstance can, but need not, occur, and that the description includes instances where the event or circumstance occurs and instances in which it does not. For example, "optional bond" means that the bond may or may not be present, and that the description includes single, double, or triple bonds.

The term "as defined above" and "as defined herein" when referring to a variable incorporates by reference the broad definition of the variable as well as particular, preferred, more preferred and most preferred definitions, if any.

Particular groups for the chemical groups whose definitions are given herein are those specifically exemplified herein.

The nomenclature used in this Application is based on AutoNom 2000™, a Symyx Solutions Inc. computerized system for the generation of IUPAC systematic nomenclature.

Chemical structures shown herein were prepared using ISIS/Draw version 2.5. Any open valency appearing on a carbon, oxygen, sulfur or nitrogen atom in the structures herein indicates the presence of a hydrogen.

The term "compound(s) of this invention" and "compound(s) of the present invention" refers to compounds of formula (I) and stereoisomers, tautomers, solvates, metabolites, salts (e.g., pharmaceutically acceptable salts), polymorphs and prodrugs thereof.

It will be appreciated, that the compounds of present invention can be derivatized at functional groups to provide derivatives which are capable of conversion back to the parent compound in vivo. Physiologically acceptable and metabolically labile derivatives, which are capable of producing the parent compounds of present invention in vivo are also within the scope of this invention.

The term "pharmaceutically acceptable salt" denotes those salts which retain the biological effectiveness and properties of the free bases and which are not biologically or otherwise undesirable, formed with inorganic acids such as hydrochloric acid, hydrobromic acid, sulfuric acid, nitric acid, carbonic acid, phosphoric acid and the like, and organic acids can be selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, salicyclic acid and the like. Particular embodiments of this invention are hydrochloride salts.

The term "pharmaceutically acceptable esters" denotes derivatives of the compounds of present invention in which hydroxy groups have been converted to the corresponding esters with inorganic or organic acids such as nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

The terms "therapeutically inert carrier" and pharmaceutically acceptable excipient" denote any ingredient having no therapeutic activity and being non-toxic such as disintegrators, binders, fillers, solvents, buffers, tonicity agents, stabilizers, antioxidants, surfactants or lubricants used in formulating pharmaceutical products.

The term "therapeutically effective amount" denotes an amount of a compound of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, disease state being treated, the severity or the disease treated, the age and relative health of the subject, the route and form of administration, the judgment of the attending medical or veterinary practitioner, and other factors.

Compounds of present invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., *Stereochemistry of Organic Compounds*, John Wiley & Sons, Inc., New York, 1994.

The term "halogen," "halo," and "halide" are used interchangeably herein and denote fluoro, chloro, bromo, or iodo. Particular examples of halogen are fluoro and chloro, particularly fluoro.

The term "alkyl" denotes a monovalent linear or branched saturated hydrocarbon group of 1 to 20 carbon atoms, in particular 1 to 12 carbon atoms. Furthermore, $C_{1-7}$ alkyl groups as described herein are particular alkyl groups.

The term "$C_{1-7}$ alkyl" denotes a monovalent linear or branched saturated hydrocarbon group of 1 to 7 carbon atoms, in particular 1 to 4 carbon atoms, for example, methyl, ethyl, propyl, isopropyl, n-butyl, iso-butyl, sec-butyl, tert-butyl and the like. Particular examples of $C_{1-7}$ alkyl are methyl, ethyl, n-propyl, iso-propyl, n-butyl, iso-butyl, tert-butyl, iso-pentyl, and tert-pentyl, particularly methyl, ethyl and iso-propyl.

The term "$C_{1-7}$ haloalkyl" denotes a $C_{1-7}$ alkyl group as defined above wherein at least one of the hydrogen atoms of the $C_{1-7}$ alkyl group has been replaced by the same or different halogen atoms, in particular by fluoro. Examples of $C_{1-7}$ haloalkyl include but are not limited to monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl, as well as those groups specifically illustrated by the examples herein below. Particular examples of $C_{1-7}$ haloalkyl are trifluoro-methyl, trifluoro-ethyl, and trifluoro n-propyl, most particularly trifluoro-ethyl.

The term "$C_{2-7}$ alkenyl" denotes a straight- or branched-hydrocarbon chain of 2 to 7, in particular 2 to 4, carbon atoms with at least one double bond. Examples of $C_{2-7}$ alkenyl include, but are not limited to, ethenyl, propenyl, prop-2-enyl, isopropenyl, n-butenyl, i-butenyl, t-butenyl and the like. Particular examples of $C_{2-7}$ alkenyl are (E)-butenyl, and iso-butenyl, most particularly (E)-butenyl.

The term "$C_{2-7}$ alkynyl" denotes a straight- or branched hydrocarbon chain of 2 to 7 carbon atoms, in particular from 2 to 4 carbon atoms, and comprising one, two or three triple bonds. Examples of $C_{2-7}$ alkynyl include, but are not limited to, ethynyl, propynyl, prop-1-ynyl, prop-2-ynyl, isopropynyl, n-butynyl, i-butynyl, t-butynyl and the like. Particular example of $C_{2-7}$ alkynyl is pronynyl, most particularly prop-1-ynyl, The term "$C_{1-7}$ alkoxy" denotes a moiety of the formula —O—R, wherein R is a $C_{1-7}$ alkyl moiety as defined herein. Examples of $C_{1-7}$ alkoxy moieties include, but are not limited to, methoxy, ethoxy, isopropoxy, tert-butoxy and the like. Particular examples of $C_{1-7}$ alkoxy are methoxy, ethoxy, and tert-butoxy, most particularly methoxy.

The term "$C_{1-7}$ haloalkoxy" denotes a $C_{1-7}$ alkoxy group as defined above wherein at least one of the hydrogen atoms of the $C_{1-7}$ alkoxy group has been replaced by the same or different halogen atoms, in particular by fluoro. Examples of $C_{1-7}$ haloalkoxy include but are not limited to monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy, as well as those groups specifically illustrated by the examples herein below.

The term "cycloalkyl" denotes a monovalent saturated monocyclic or bicyclic hydrocarbon radical of 3 to 8 ring carbon atoms. Bicyclic means consisting of two saturated carbocycles having two carbon atoms in common, i.e. the bridge separating the two rings is either a single bond or a chain of one or two carbon atoms. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, bicyclo[2.2.2]octanyl or adamantanyl. Particular examples of cycloalkyl are cyclopropyl, cyclobutyl, cyclopentyl, and cyclohexyl, particularly cyclopropyl and cyclobutyl.

The term "heterocycloalkyl" denotes a monovalent saturated or partly unsaturated mono- or bicyclic ring system of 4 to 9 ring atoms, comprising 1, 2, or 3 ring heteroatoms selected from N, O and S, the remaining ring atoms being carbon. Bicyclic means consisting of two saturated cycles having two ring atoms in common, i.e. the bridge separating the two rings is either a single bond or a chain of one or two ring atoms. Heterocycloalkyl can be unsubstituted or substituted as described herein. Examples for monocyclic saturated heterocycloalkyl are azetidinyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl are oxetanyl, piperidinyl, piperazinyl, tetrahydrofuranyl, tetrahydropyranyl, morpholinyl, thiomorpholinyl and dioxanyl, most particularly dioxanyl, and tetrahydrofuranyl.

The term "aryl" denotes a monovalent aromatic carbocyclic mono- or bicyclic ring system comprising 6 to 10 carbon ring atoms. The aryl group can optionally be substituted with one, two or three substituents, wherein each substituent is independently e.g. $C_{1-7}$ alkyl, halo, $C_{1-7}$ alkoxy, sulfonyl, cyano, cycloalkyl, heterocyclyl, phenyl, unless otherwise specifically indicated. Examples of aryl moieties include optionally substituted phenyl and optionally substituted naphthyl. Particular example of aryl is phenyl.

The term "aryl annellated to heterocycloalkyl" denotes an aryl as defined herein and a heterocycloalkyl as defined herein which are fused together sharing two adjacent ring atoms. Examples of aryl annellated to heterocycloalkyl include optionally substituted benzodioxolyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. The heteroaryl group can optionally be substituted as described herein. Examples of heteroaryl moieties include optionally substituted pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, quinoxalinyl, carbazolyl, or acridinyl. Particular example of heteroaryl is isoxazolyl, benzoisoxazolyl, pyrrolyl, pyrazolyl, oxadiazolyl, pyridinyl, thienyl, pyrazinyl, or quinolinyl, most particularly isoxazolyl, benzoisoxazolyl, thienyl, or quinolinyl.

The term "oxo" denotes a divalent oxygen radical atom, e.g. =O.

The term "amino-protecting group" denotes groups intended to protect an amino group against undesirable reactions during synthetic procedures and includes, but is not limited to, benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (Boc), trifluoroacetyl, and the like. Further examples of these groups are found in T. W. Greene and P. G. M. Wuts, "*Protective Groups in Organic Synthesis*", 2nd ed., John Wiley & Sons, Inc., New York, N.Y., 1991, chapter 7; E. Haslam, "*Protective Groups in Organic Chemistry*", J. G. W. McOmie, Ed., Plenum Press, New York, N.Y., 1973, *Chapter 5*, and T. W. Greene, "*Protective Groups in Organic Synthesis*", John Wiley and Sons, New York, N.Y., 1981. The term "protected amino group" refers to an amino group substituted with one of the above amino-protecting groups.

In detail, the present invention relates to compounds of formula (I)

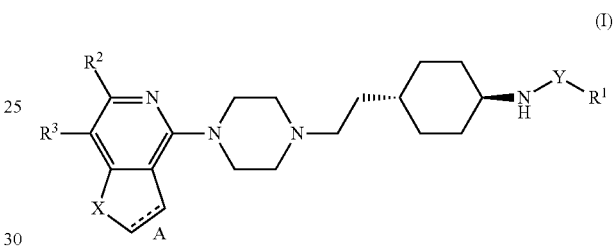

wherein

X is O or S;

Y is —C(O)— or —S(O)$_2$—;

A is a single bond or double bond,
with the proviso that when X is S then A is a double bond;

$R^1$ is hydrogen, $C_{1-7}$ alkyl, $C_{1-7}$ haloalkyl, $C_{2-7}$ alkenyl, $C_{2-7}$ alkynyl, cycloalkyl, heterocycloalkyl, aryl, aryl annellated to heterocycloalkyl, heteroaryl, or —N(R$^6$)$_2$, wherein $C_{1-7}$ alkyl, $C_{1-7}$ haloalkyl, $C_{2-7}$ alkenyl, $C_{2-7}$ alkynyl are optionally substituted by one to three substituents selected independently from the group consisting of cyano, cycloalkyl, heterocycloalkyl, aryl, aryl annellated to heterocycloalkyl, heteroaryl, —C(O)N(R$^6$)$_2$, —N(R$^6$)$_2$, —NH(CO)—$C_{1-7}$ alkyl, hydroxy, $C_{1-7}$ alkoxy, $C_{1-7}$ haloalkoxy, oxo, and —S(O)$_2$R$^7$, and wherein cycloalkyl, heterocycloalkyl, aryl, aryl annellated to heterocycloalkyl, and heteroaryl are optionally substituted by one to three independent R$^4$;

$R^2$ and $R^3$ are each independently hydrogen, halogen, $C_{1-7}$ alkyl, $C_{1-7}$ haloalkyl, hydroxy, $C_{1-7}$ alkoxy or $C_{1-7}$ haloalkoxy;

$R^4$ is halogen, cyano, $C_{1-7}$ alkyl, $C_{1-7}$ haloalkyl, cycloalkyl, heterocycloalkyl, aryl, heteroaryl, —C(O)N(R$^6$)$_2$, —N(R$^6$)$_2$, —NH(CO)—$C_{1-7}$ alkyl, hydroxy, $C_{1-7}$ alkoxy, $C_{1-7}$ haloalkoxy, oxo, —S(O)$_2$R$^7$, or $C_{1-7}$ alkyl substituted by one to three substituents selected independently from the group consisting of cyano, hydroxy, $C_{1-7}$ alkoxy, and $C_{1-7}$ haloalkoxy, wherein cycloalkyl, heterocycloalkyl, aryl, and heteroaryl are optionally substituted by one to three independent R$^5$;

$R^5$ is halogen, cyano, $C_{1-7}$ alkyl, $C_{1-7}$ haloalkyl, hydroxy, $C_{1-7}$ alkoxy, $C_{1-7}$ haloalkoxy, or oxo;

$R^6$ is hydrogen or $C_{1-7}$ alkyl; and $R^7$ is hydrogen, $C_{1-7}$ alkyl, or aryl, wherein aryl is optionally substituted by one to three independent R$^5$;

and pharmaceutically acceptable salts and esters thereof.

Particular embodiments of present invention provide compounds of formula (I) and pharmaceutically acceptable salts thereof and pharmaceutically acceptable esters thereof.

Further, it is to be understood that every embodiment relating to a specific residue X, Y, A $R^1$, $R^2$, $R^3$, $R^4$, $R^5$, $R^6$, or $R^7$ as disclosed herein can be combined with any other embodiment relating to another residue X, Y, A $R^1$, $R^2$, $R^3$, $R^4$, $R^5$, $R^6$, or $R^7$ as disclosed herein.

In particular the present invention provides compounds of formula (I) wherein

X is O or S;

Y is —C(O)— or —S(O)$_2$—;

A is a single bond or double bond, with the proviso that when X is S then A is a double bond;

$R^1$ is hydrogen, $C_{1-7}$ alkyl, $C_{1-7}$ haloalkyl, $C_{2-7}$ alkenyl, $C_{2-7}$ alkynyl, cycloalkyl, heterocycloalkyl, aryl, heteroaryl, or —N($R^6$)$_2$, wherein $C_{1-7}$ alkyl, $C_{1-7}$ haloalkyl, $C_{2-7}$ alkenyl, $C_{2-7}$ alkynyl are optionally substituted by one to three substituents selected independently from the group consisting of cyano, cycloalkyl, heterocycloalkyl, aryl, heteroaryl, —C(O)N($R^6$)$_2$, —N($R^6$)$_2$, —NH(CO)—$C_{1-7}$ alkyl, hydroxy, $C_{1-7}$ alkoxy, $C_{1-7}$ haloalkoxy, oxo, and —S(O)$_2$$R^7$, and wherein cycloalkyl, heterocycloalkyl, aryl, and heteroaryl are optionally substituted by one to three independent $R^4$;

$R^2$ and $R^3$ are each independently hydrogen, halogen, $C_{1-7}$ alkyl, $C_{1-7}$ haloalkyl, hydroxy, $C_{1-7}$ alkoxy or $C_{1-7}$ haloalkoxy;

$R^4$ is halogen, cyano, $C_{1-7}$ alkyl, $C_{1-7}$ haloalkyl, cycloalkyl, heterocycloalkyl, aryl, heteroaryl, —C(O)N($R^6$)$_2$, —N($R^6$)$_2$, —NH(CO)—$C_{1-7}$ alkyl, hydroxy, $C_{1-7}$ alkoxy, $C_{1-7}$ haloalkoxy, oxo, —S(O)$_2$$R^7$, or $C_{1-7}$ alkyl substituted by one to three substituents selected independently from the group consisting of cyano, hydroxy, $C_{1-7}$ alkoxy, and $C_{1-7}$ haloalkoxy, wherein cycloalkyl, heterocycloalkyl, aryl, and heteroaryl are optionally substituted by one to three independent $R^5$;

$R^5$ is halogen, cyano, $C_{1-7}$ alkyl, $C_{1-7}$ haloalkyl, hydroxy, $C_{1-7}$ alkoxy, $C_{1-7}$ haloalkoxy, or oxo;

$R^6$ is hydrogen or $C_{1-7}$ alkyl; and $R^7$ is hydrogen, $C_{1-7}$ alkyl, or aryl, wherein aryl is optionally substituted by one to three independent $R^5$;

and pharmaceutically acceptable salts and esters thereof.

In a particular embodiment of the compound of formula (I), X is O.

In a particular embodiment of the compound of formula (I), A is a single bond.

In a particular embodiment of the compound of formula (I), A is a double bond.

In a particular embodiment of the compound of formula (I), X is O and A is a single bond.

In a particular embodiment of the compound of formula (I), X is O and A is a double bond.

In a particular embodiment of the compound of formula (I), X is S and A is a double bond.

In a particular embodiment of the compound of formula (I), Y is —C(O)—.

In a particular embodiment of the compound of formula (I), X is O, A is a single bond and Y is —C(O)—.

In a particular embodiment of the compound of formula (I), X is O, A is a double bond and Y is —C(O)—.

In a particular embodiment of the compound of formula (I), $R^1$ is hydrogen, $C_{1-7}$ alkyl, $C_{1-7}$ haloalkyl, $C_{2-7}$ alkenyl, $C_{2-7}$ alkynyl, cycloalkyl, heterocycloalkyl, aryl, aryl annellated to heterocycloalkyl, heteroaryl, or —N($R^6$)$_2$, wherein $C_{1-7}$ alkyl, and $C_{1-7}$ haloalkyl are optionally substituted by one to three substituents selected independently from the group consisting of cyano, cycloalkyl, heterocycloalkyl, aryl annellated to heterocycloalkyl, heteroaryl, —C(O)N($R^6$)$_2$, hydroxy, $C_{1-7}$ alkoxy, $C_{1-7}$ haloalkoxy, and —S(O)$_2$$R^7$, and wherein cycloalkyl, heterocycloalkyl, aryl, and heteroaryl are optionally substituted by one to three independent $R^4$;

In a particular embodiment of the compound of formula (I), $R^1$ is $C_{1-7}$ alkyl, $C_{1-7}$ haloalkyl, cycloalkyl, heterocycloalkyl, aryl, heteroaryl, —N($R^6$)$_2$, or $C_{1-7}$ alkyl substituted by one to three substituents selected independently from the group consisting of cyano, cycloalkyl, heterocycloalkyl, hydroxy, $C_{1-7}$ alkoxy, and —S(O)$_2$$R^7$, wherein cycloalkyl, heterocycloalkyl, aryl, and heteroaryl are optionally substituted by one to three independent $R^4$.

In a particular embodiment of the compound of formula (I), $R^1$ is —N(methyl)$_2$.

In a particular embodiment of the compound of formula (I), $R^1$ is methyl; methyl substituted by a substituent selected from the group consisting of cyano, cyclopropyl, cyclobutyl, hydroxy-cyclobutyl, methoxy-cyclopentyl, hydroxy-cyclohexyl, methoxy-cyclohexyl, oxetanyl, tetrahydrofuranyl, hydroxy-tetrahydrofuranyl, tetrahydropyranyl, dioxanyl, benzodioxolyl, methyl-isoxazolyl, benzoisoxazolyl, hydroxy, methoxy, ethoxy, and —S(O)$_2$-methyl; ethyl; ethyl substituted with a substituent selected from the group consisting of hydroxy, methoxy, and C(O)—N(methyl)$_2$; n-propyl; n-propyl substituted by methoxy; iso-propyl; iso-propyl substituted by hydroxy; n-butyl; n-butyl substituted by hydroxy; iso-butyl; iso-butyl substituted by hydroxy; tert-butyl; iso-pentyl; tert-pentyl; trifluoro-methyl; trifluoro-ethyl; trifluoro-ethyl substituted by hydroxy; trifluoro-n-propyl; trifluoro-n-propyl substituted by hydroxy; (E)-butenyl; iso-butenyl; propynyl; cyclopropyl; cyclopropyl substituted by fluoro; cyclopropyl substituted by hydroxy; cyclobutyl; cyclobutyl substituted by hydroxy; cyclohexyl; cyclohexyl substituted by methyl and hydroxy; tetrahydrofuranyl; tetrahydropyranyl; phenyl; phenyl substituted by a substituent selected from the group consisting of fluoro, chloro, cyano, methyl, tert-butyl, tert-butoxy, piperidinyl, methyl-piperazinyl, morpholinyl, dioxo-thiomorpholinyl, phenyl, pyrrolyl, pyrazolyl, methyl-oxadiazolyl, and pyridinyl; benzodioxolyl; thienyl; thienyl substituted by —S(O)$_2$-methyl; isoxazolyl; methyl-isoxazolyl; pyridinyl; methyl-pyridinyl; morpholinyl-pyridinyl; pyrazinyl; morpholinyl-pyrazinyl; or quinolinyl.

In a particular embodiment of the compound of formula (I), $R^1$ is methyl; methyl substituted with a substituent selected from the group consisting of cyano, cyclopropyl, cyclobutyl, methoxy-cyclopentyl, hydroxy-cyclohexyl, methoxy-cyclohexyl, hydroxy, methoxy, ethoxy, oxetanyl, tetrahydrofuranyl, hydroxy-tetrahydrofuranyl, tetrahydropyranyl, dioxanyl, methyl-isoxazolyl, benzoisoxazolyl and —S(O)$_2$-methyl; ethyl; ethyl substituted with a substituent selected from the group consisting of fluoro, hydroxy and methoxy; n-propyl, iso-propyl; n-butyl, n-butyl substituted by hydroxy, iso-butyl; tert-butyl; iso-pentyl, tert-pentyl; (E)-butenyl, propynyl; cyclopropyl; cyclopropyl substituted by fluoro; cyclopropyl substituted by hydroxy; cyclobutyl; cyclohexyl substituted by methyl and hydroxy; tetrahydrofuranyl; tetrahydropyranyl; phenyl; phenyl substituted with a substituent selected from the group consisting of fluoro, chloro, trifluoro-methyl, morpholinyl, piperidinyl and phenyl; thienyl, thienyl substituted by methylsulfonyl, or quinolinyl.

In a particular embodiment of the compound of formula (I), $R^1$ is methyl; methyl substituted with a substituent selected from the group consisting of cyano, cyclopropyl, cyclobutyl, methoxy-cyclopentyl, hydroxy-cyclohexyl, methoxy-cyclohexyl, hydroxy, methoxy, oxetanyl, tetrahydrofuranyl, tetrahydropyranyl, dioxanyl and —S(O)₂-methyl; ethyl; ethyl substituted with a substituent selected from the group consisting of fluoro, hydroxy and methoxy; iso-propyl; iso-butyl; tert-pentyl; cyclopropyl; cyclobutyl; tetrahydrofuranyl; tetrahydropyranyl; phenyl; phenyl substituted with a substituent selected from the group consisting of fluoro, morpholinyl and piperidinyl; or quinolinyl.

In a particular embodiment of the compound of formula (I), $R^1$ is methyl; methyl substituted with a substituent selected from the group consisting of cyano, cyclopropyl, hydroxy, dioxanyl and —S(O)₂-methyl; ethyl; ethyl substituted with fluoro; iso-propyl, cyclopropyl; cyclobutyl; or tetrahydrofuranyl.

In a particular embodiment of the compound of formula (I), $R^2$ is hydrogen.

In a particular embodiment of the compound of formula (I), $R^3$ is hydrogen or methyl.

In a particular embodiment of the compound of formula (I), $R^3$ is hydrogen.

In a particular embodiment of the compound of formula (I), $R^4$ is halogen, cyano, $C_{1-7}$ alkyl, $C_{1-7}$ haloalkyl, cycloalkyl, heterocycloalkyl, hydroxy, $C_{1-7}$ alkoxy, aryl, aryl annellated to heterocycloalkyl, heteroaryl or —S(O)₂R⁷, wherein cycloalkyl, heterocycloalkyl, aryl, aryl annellated to heterocycloalkyl and heteroaryl, are optionally substituted by one to three independent $R^5$.

In a particular embodiment of the compound of formula (I), $R^4$ is fluoro, chloro, cyano, methyl, trifluoro-methyl, tert-butyl, cyclopropyl, cyclobutyl, cyclopentyl substituted by methoxy, cyclohexyl substituted by hydroxy or methoxy, oxetanyl, tetrahydrofuranyl, tetrahydropyranyl, piperidinyl, piperazinyl, morpholinyl, thiomorpholinyl, thiomorpholinyl substituted by oxo, dioxanyl, phenyl, benzodioxolyl, pyrrolyl, pyrazolyl, oxadiazolyl, methyl-oxadiazolyl, pyridinyl, hydroxy, methoxy, ethoxy, tert-butoxy, or —S(O)₂-methyl.

In a particular embodiment of the compound of formula (I), $R^4$ is fluoro, cyano, cyclopropyl, cyclobutyl, cyclopentyl substituted by methoxy, cyclohexyl substituted by hydroxy or methoxy, oxetanyl, tetrahydrofuranyl, tetrahydropyranyl, morpholinyl, dioxanyl, hydroxy, methoxy, or —S(O)₂-methyl.

In a particular embodiment of the compound of formula (I), $R^4$ is fluoro, morpholinyl, phenyl, or —S(O)₂-methyl.

In a particular embodiment of the compound of formula (I), $R^4$ is fluoro, cyano, cyclopropyl, dioxanyl, hydroxy, or —S(O)₂-methyl.

In a particular embodiment of the compound of formula (I), $R^5$ is halogen, hydroxy, $C_{1-7}$ alkyl, $C_{1-7}$ alkoxy and oxo.

In a particular embodiment of the compound of formula (I), $R^5$ is fluoro, hydroxy, methyl, methoxy, or oxo.

In a particular embodiment of the compound of formula (I), $R^6$ is $C_{1-7}$ alkyl.

In a particular embodiment of the compound of formula (I), $R^6$ is methyl.

In a particular embodiment of the compound of formula (I), $R^7$ is $C_{1-7}$ alkyl.

In a particular embodiment of the compound of formula (I), $R^7$ is methyl.

A particular embodiment of the present invention relates to compounds of formula (I) wherein the two opposing substituents at the central cyclohexyl moiety of the molecular backbone, the amidyl residue and the piperazinyl-ethyl residue, are oriented in trans-configuration.

A particular embodiment of the present invention relates to compounds of formula (I')

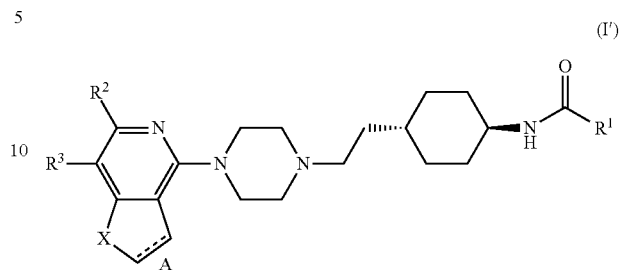

wherein X, A, $R^1$, $R^2$ and $R^3$ are as defined above.

A particular embodiment of the present invention relates to compounds of formula (I")

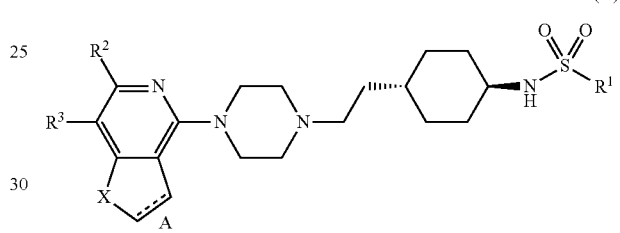

wherein X, A, $R^1$, $R^2$ and $R^3$ are as defined above.

A particular embodiment of the present invention relates to compounds of formula (Ia)

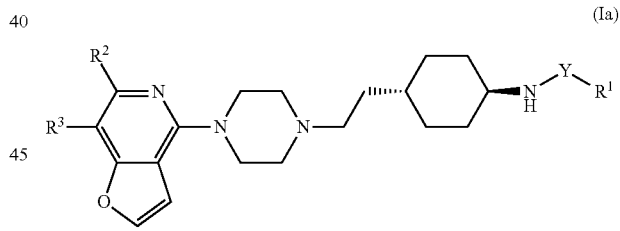

wherein Y, $R^1$, $R^2$ and $R^3$ are as defined above.

A particular embodiment of the present invention relates to compounds of formula (Ia')

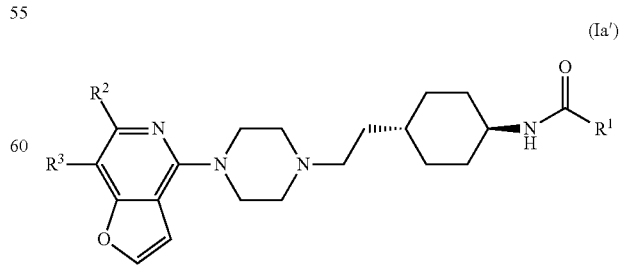

wherein $R^1$, $R^2$ and $R^3$ are as defined above.

A particular embodiment of the present invention relates to compounds of formula (Ia")

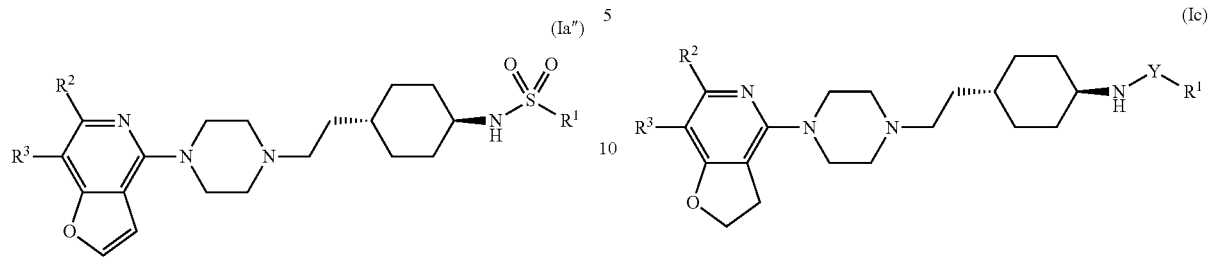

wherein R¹, R² and R³ are as defined above.

A particular embodiment of the present invention relates to compounds of formula (Ib)

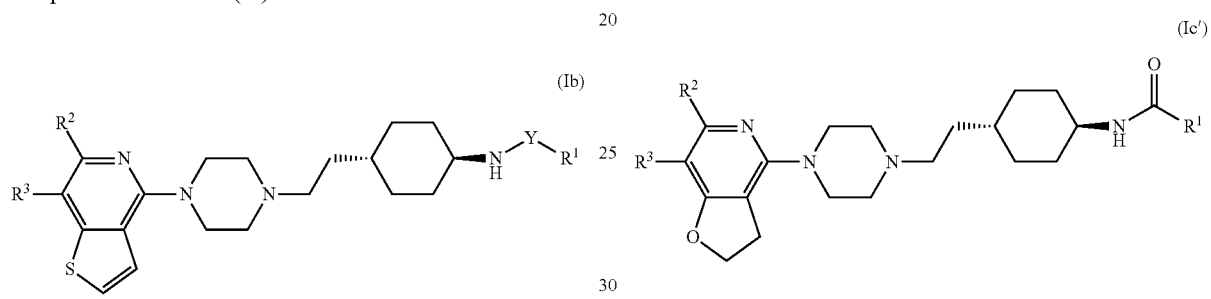

wherein Y, R¹, R² and R³ are as defined above.

A particular embodiment of the present invention relates to compounds of formula (Ib')

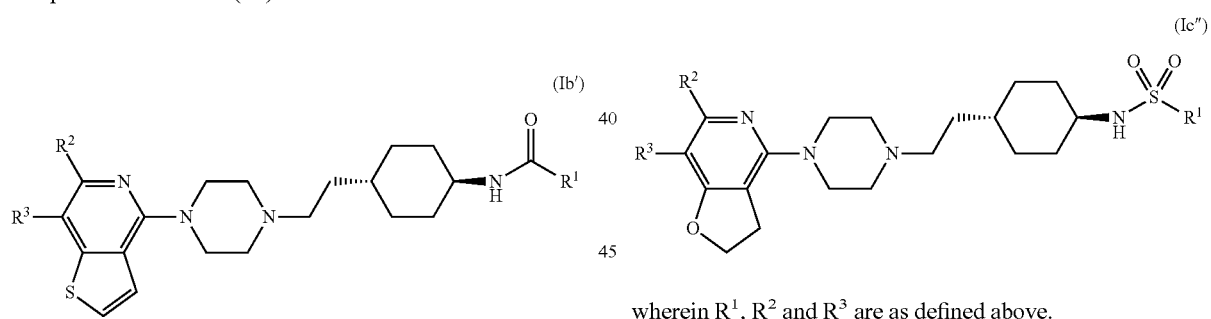

wherein R¹, R² and R³ are as defined above.

A particular embodiment of the present invention relates to compounds of formula (Ib")

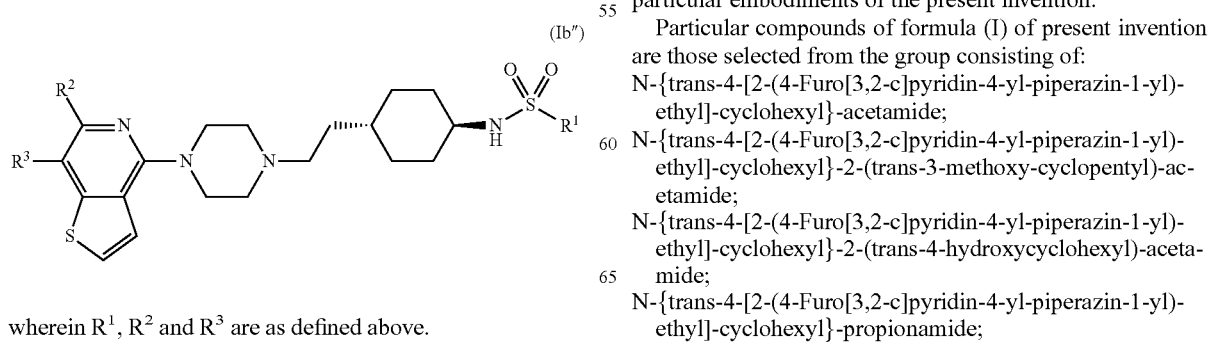

wherein R¹, R² and R³ are as defined above.

A particular embodiment of the present invention relates to compounds of formula (Ic)

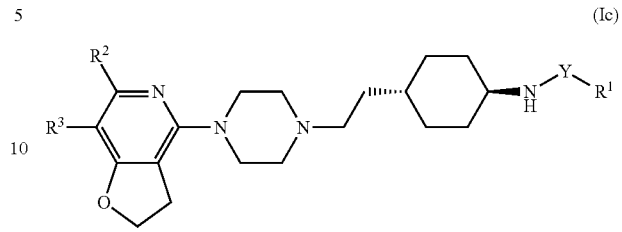

wherein Y, R¹, R² and R³ are as defined above.

A particular embodiment of the present invention relates to compounds of formula (Ic')

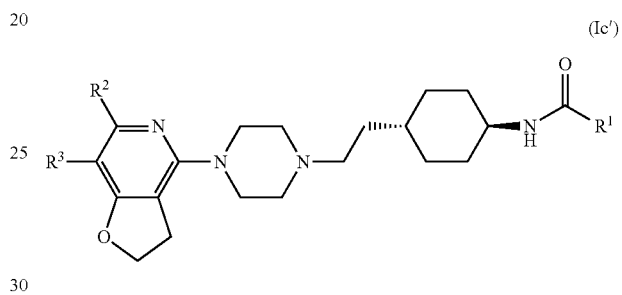

wherein R¹, R² and R³ are as defined above.

A particular embodiment of the present invention relates to compounds of formula (Ic")

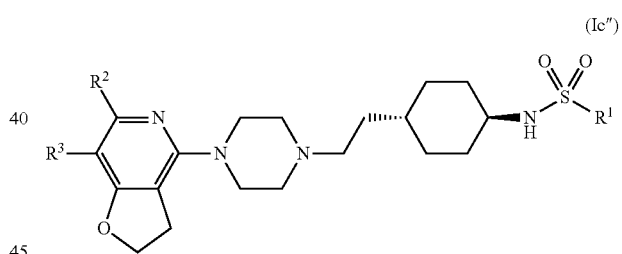

wherein R¹, R² and R³ are as defined above.

A particular embodiment of the present invention relates to compounds of formula (I) as described in the examples as individual compounds as well as pharmaceutically acceptable salts as well as pharmaceutically acceptable esters thereof. Furthermore, the substituents as found in the specific examples described below, individually constitute separate particular embodiments of the present invention.

Particular compounds of formula (I) of present invention are those selected from the group consisting of:
N-{trans-4-[2-(4-Furo[3,2-c]pyridin-4-yl-piperazin-1-yl)-ethyl]-cyclohexyl}-acetamide;
N-{trans-4-[2-(4-Furo[3,2-c]pyridin-4-yl-piperazin-1-yl)-ethyl]-cyclohexyl}-2-(trans-3-methoxy-cyclopentyl)-acetamide;
N-{trans-4-[2-(4-Furo[3,2-c]pyridin-4-yl-piperazin-1-yl)-ethyl]-cyclohexyl}-2-(trans-4-hydroxycyclohexyl)-acetamide;
N-{trans-4-[2-(4-Furo[3,2-c]pyridin-4-yl-piperazin-1-yl)-ethyl]-cyclohexyl}-propionamide;

N-{trans-4-[2-(4-Furo[3,2-c]pyridin-4-yl-piperazin-1-yl)-ethyl]-cyclohexyl}-3-methoxypropionamide;
N-{trans-4-[2-(4-Furo[3,2-c]pyridin-4-yl-piperazin-1-yl)-ethyl]-cyclohexyl}-3-hydroxypropionamide;
N-{trans-4-[2-(4-Furo[3,2-c]pyridin-4-yl-piperazin-1-yl)-ethyl]-cyclohexyl}-2-hydroxyacetamide;
N-{trans-4-[2-(4-Furo[3,2-c]pyridin-4-yl-piperazin-1-yl)-ethyl]-cyclohexyl}-2-methoxyacetamide;
N-{trans-4-[2-(4-Furo[3,2-c]pyridin-4-yl-piperazin-1-yl)-ethyl]-cyclohexyl}-2-(trans-4-methoxy-cyclohexyl)-acetamide;
N-{trans-4-[2-(4-Furo[3,2-c]pyridin-4-yl-piperazin-1-yl)-ethyl]-cyclohexyl}-2-(tetrahydropyran-4-yl)-acetamide;
Tetrahydro-pyran-4-carboxylic acid {trans-4-[2-(4-furo[3,2-c]pyridin-4-yl-piperazin-1-yl)-ethyl]-cyclohexyl}-amide;
2-Ethoxy-N-{trans-4-[2-(4-furo[3,2-c]pyridin-4-yl-piperazin-1-yl)-ethyl]-cyclohexyl}-acetamide;
Cyclopropanecarboxylic acid {trans-4-[2-(4-furo[3,2-c]pyridin-4-yl-piperazin-1-yl)-ethyl]-cyclohexyl}-amide;
N-{trans-4-[2-(4-Furo[3,2-c]pyridin-4-yl-piperazin-1-yl)-ethyl]-cyclohexyl}-methanesulfonamide;
N-{trans-4-[2-(4-Thieno[3,2-c]pyridin-4-yl-piperazin-1-yl)-ethyl]-cyclohexyl}-acetamide;
Ethanesulfonic acid {trans-4-[2-(4-furo[3,2-c]pyridin-4-yl-piperazin-1-yl)-ethyl]-cyclohexyl}-amide;
N'-(trans-4{[4-(furo[3,2-c]pyridin-4-yl)-piperazin-1-yl]-ethyl}cyclohexyl)-N,N-dimethylsulfamide;
N-{trans-4-[2-(4-Thieno[3,2-c]pyridin-4-yl-piperazin-1-yl)-ethyl]-cyclohexyl}-propionamide;
3-Methoxy-N-{trans-4-[2-(4-thieno[3,2-c]pyridin-4-yl-piperazin-1-yl)-ethyl]-cyclohexyl}-propionamide;
2-(trans-4-Methoxy-cyclohexyl)-N-{trans-4-[2-(4-thieno[3,2-c]pyridin-4-yl-piperazin-1-yl)-ethyl]-cyclohexyl}-acetamide;
2-(trans-3-Methoxy-cyclopentyl)-N-{trans-4-[2-(4-thieno[3,2-c]pyridin-4-yl-piperazin-1-yl)-ethyl]-cyclohexyl}-acetamide;
2-Methoxy-N-{trans-4-[2-(4-thieno[3,2-c]pyridin-4-yl-piperazin-1-yl)-ethyl]-cyclohexyl}-acetamide;
2-(Tetrahydro-pyran-4-yl)-N-{trans-4-[2-(4-thieno[3,2-c]pyridin-4-yl-piperazin-1-yl)-ethyl]-cyclohexyl}-acetamide;
Tetrahydro-pyran-4-carboxylic acid {trans-4-[2-(4-thieno[3,2-c]pyridin-4-yl-piperazin-1-yl)-ethyl]-cyclohexyl}-amide;
2-((1R,3R)-3-Methoxy-cyclopentyl)-N-{trans-4-[2-(4-thieno[3,2-c]pyridin-4-yl-piperazin-1-yl)-ethyl]-cyclohexyl}-acetamide;
2-((1S,3S)-3-Methoxy-cyclopentyl)-N-{trans-4-[2-(4-thieno[3,2-c]pyridin-4-yl-piperazin-1-yl)-ethyl]-cyclohexyl}-acetamide;
2-Hydroxy-N-{trans-4-[2-(4-thieno[3,2-c]pyridin-4-yl-piperazin-1-yl)-ethyl]-cyclohexyl}-acetamide;
2-(trans-4-Hydroxy-cyclohexyl)-N-{trans-4-[2-(4-thieno[3,2-c]pyridin-4-yl-piperazin-1-yl)-ethyl]-cyclohexyl}-acetamide;
Quinoline-4-carboxylic acid {trans-4-[2-(4-furo[3,2-c]pyridin-4-yl-piperazin-1-yl)-ethyl]-cyclohexyl}-amide;
N-{trans-4-[2-(4-Thieno[3,2-c]pyridin-4-yl-piperazin-1-yl)-ethyl]-cyclohexyl}-methanesulfonamide;
Ethanesulfonic acid {trans-4-[2-(4-thieno[3,2-c]pyridin-4-yl-piperazin-1-yl)-ethyl]-cyclohexyl}-amide;
trans-N-(4-{2-[4-(2,3-Dihydro-furo[3,2-c]pyridin-4-yl)-piperazin-1-yl]-ethyl}-cyclohexyl)-acetamide;
trans-N-(4-{2-[4-(2,3-Dihydrofuro[3,2-c]pyridin-4-yl)-piperazin-1-yl]-ethyl}-cyclohexyl)-tetrahydro-2H-pyran-4-carboxamide;
trans-N-(4-{2-[4-(2,3-Dihydrofuro[3,2-c]pyridin-4-yl)-piperazin-1-yl]-ethyl}-cyclohexyl)-2-(tetrahydro-2H-pyran-4-yl)-acetamide;
trans-N-(4-{2-[4-(2,3-Dihydrofuro[3,2-c]pyridin-4-yl)-piperazin-1-yl]-ethyl}-cyclohexyl)-3-methoxypropanamide;
trans-N-(4-{2-[4-(2,3-Dihydrofuro[3,2-c]pyridin-4-yl)-piperazin-1-yl]-ethyl}-cyclohexyl)-propionamide;
trans-N-(4-{2-[4-(2,3-Dihydrofuro[3,2-c]pyridin-4-yl)-piperazin-1-yl]-ethyl}-cyclohexyl)-2-(rac-1,4-dioxan-2-yl)-acetamide;
trans-N-(4-{2-[4-(2,3-Dihydrofuro[3,2-c]pyridin-4-yl)-piperazin-1-yl]-ethyl}-cyclohexyl)-2-methoxyacetamide;
trans-N-(4-{2-[4-(2,3-Dihydrofuro[3,2-c]pyridin-4-yl)-piperazin-1-yl]-ethyl}-cyclohexyl)-methylsulfonyl-acetamide;
trans-N-(4-{2-[4-(2,3-Dihydrofuro[3,2-c]pyridin-4-yl)-piperazin-1-yl]-ethyl}-cyclohexyl)-hydroxyacetamide;
trans-N-(4-{2-[4-(2,3-Dihydrofuro[3,2-c]pyridin-4-yl)-piperazin-1-yl]-ethyl}-cyclohexyl)-3-hydroxypropanamide;
trans-N-(4-{2-[4-(2,3-Dihydrofuro[3,2-c]pyridin-4-yl)-piperazin-1-yl]-ethyl}-cyclohexyl)-rac-tetrahydrofuran-3-carboxamide;
trans-N-(4-{2-[4-(2,3-Dihydrofuro[3,2-c]pyridin-4-yl)-piperazin-1-yl]-ethyl}-cyclohexyl)-rac-tetrahydrofuran-2-carboxamide;
trans-N-(4-{2-[4-(2,3-Dihydro-furo[3,2-c]pyridin-4-yl)-piperazin-1-yl]-ethyl}-cyclohexyl)-benzamide;
trans-N-(4-{2-[4-(2,3-Dihydro-furo[3,2-c]pyridin-4-yl)-piperazin-1-yl]-ethyl}-cyclohexyl)-4-fluoro-benzamide;
trans-4-Chloro-N-(4-{2-[4-(2,3-dihydro-furo[3,2-c]pyridin-4-yl)-piperazin-1-yl]-ethyl}-cyclohexyl)-benzamide;
trans-N-(4-{2-[4-(2,3-Dihydro-furo[3,2-c]pyridin-4-yl)-piperazin-1-yl]-ethyl}-cyclohexyl)-4-trifluoromethyl-benzamide;
trans-N-(4-{2-[4-(2,3-Dihydro-furo[3,2-c]pyridin-4-yl)-piperazin-1-yl]-ethyl}-cyclohexyl)-methanesulfonamide;
Ethanesulfonic acid trans-(4-{2-[4-(2,3-dihydro-furo[3,2-c]pyridin-4-yl)-piperazin-1-yl]-ethyl}-cyclohexyl)-amide;
trans-N-(4-{2-[4-(2,3-Dihydro-furo[3,2-c]pyridin-4-yl)-piperazin-1-yl]-ethyl}-cyclohexyl)-4-fluoro-benzenesulfonamide;
trans-2-Cyclopropyl-N-(4-{2-[4-(2,3-dihydro-furo[3,2-c]pyridin-4-yl)-piperazin-1-yl]-ethyl}-cyclohexyl)-acetamide;
Cyclobutanecarboxylic acid trans-(4-{2-[4-(2,3-dihydrofuro[3,2-c]pyridin-4-yl)-piperazin-1-yl]-ethyl}-cyclohexyl)-amide;
rac-Tetrahydro-pyran-3-carboxylic acid trans-(4-{2-[4-(2,3-dihydro-furo[3,2-c]pyridin-4-yl)-piperazin-1-yl]-ethyl}-cyclohexyl)-amide;
trans-4-Hydroxy-4-methyl-cyclohexanecarboxylic acid trans-(4-{2-[4-(2,3-dihydro-furo[3,2-c]pyridin-4-yl)-piperazin-1-yl]-ethyl}-cyclohexyl)-amide;
cis-4-Hydroxy-4-methyl-cyclohexanecarboxylic acid trans-(4-{2-[4-(2,3-dihydro-furo[3,2-c]pyridin-4-yl)-piperazin-1-yl]-ethyl}-cyclohexyl)-amide;
trans-N-(4-{2-[4-(2,3-Dihydro-furo[3,2-c]pyridin-4-yl)-piperazin-1-yl]-ethyl}-cyclohexyl)-4-piperidin-1-yl-benzamide;
trans-N-(4-{2-[4-(2,3-Dihydro-furo[3,2-c]pyridin-4-yl)-piperazin-1-yl]-ethyl}-cyclohexyl)-4-morpholin-4-yl-benzamide;
1-Hydroxy-cyclopropanecarboxylic acid trans-(4-{2-[4-(2,3-dihydro-furo[3,2-c]pyridin-4-yl)-piperazin-1-yl]-ethyl}-cyclohexyl)-amide;
trans-2-Cyano-N-(4-{2-[4-(2,3-dihydro-furo[3,2-c]pyridin-4-yl)-piperazin-1-yl]-ethyl}-cyclohexyl)-acetamide;

trans-N-(4-{2-[4-(2,3-Dihydro-furo[3,2-c]pyridin-4-yl)-
piperazin-1-yl]-ethyl}-cyclohexyl)-3,3,3-trifluoro-propi-
onamide;
trans-N-(4-{2-[4-(2,3-Dihydro-furo[3,2-c]pyridin-4-yl)-
piperazin-1-yl]-ethyl}-cyclohexyl)-2-(R)-[1,4]dioxan-2-
yl-acetamide;
Quinoline-4-carboxylic acid trans-(4-{2-[4-(2,3-dihydro-
furo[3,2-c]pyridin-4-yl)-piperazin-1-yl]-ethyl}-cyclo-
hexyl)-amide;
Cyclopropanecarboxylic acid trans-(4-{2-[4-(2,3-dihydro-
furo[3,2-c]pyridin-4-yl)-piperazin-1-yl]-ethyl}-cyclo-
hexyl)-amide;
trans-N-(4-{2-[4-(2,3-Dihydro-furo[3,2-c]pyridin-4-yl)-
piperazin-1-yl]-ethyl}-cyclohexyl)-2-rac-(tetrahydro-fu-
ran-2-yl)-acetamide;
trans-N-(4-{2-[4-(2,3-Dihydro-furo[3,2-c]pyridin-4-yl)-
piperazin-1-yl]-ethyl}-cyclohexyl)-2-trans-(4-methoxy-
cyclohexyl)-acetamide;
N'-trans-(4-{2-[4-(2,3-dihydro-furo[3,2-c]pyridin-4-yl)-pip-
erazin-1-yl]-ethyl}-cyclohexyl)-N,N-dimethyl-sulfa-
mide;
trans-N-(4-{2-[4-(2,3-Dihydro-furo[3,2-c]pyridin-4-yl)-
piperazin-1-yl]-ethyl}-cyclohexyl)-2-(S)-[1,4]dioxan-2-
yl-acetamide;
trans-N-(4-{2-[4-(2,3-Dihydro-furo[3,2-c]pyridin-4-yl)-
piperazin-1-yl]-ethyl}-cyclohexyl)-2-(R)-(tetrahydro-fu-
ran-2-yl)-acetamide;
trans-N-(4-{2-[4-(2,3-Dihydro-furo[3,2-c]pyridin-4-yl)-
piperazin-1-yl]-ethyl}-cyclohexyl)-2-(S)-(tetrahydro-fu-
ran-2-yl)-acetamide;
trans-N-(4-{2-[4-(2,3-Dihydro-furo[3,2-c]pyridin-4-yl)-
piperazin-1-yl]-ethyl}-cyclohexyl)-2,2-dimethyl-propi-
onamide;
trans-N-(4-{2-[4-(2,3-Dihydro-furo[3,2-c]pyridin-4-yl)-
piperazin-1-yl]-ethyl}-cyclohexyl)-3-methyl-butyramide;
trans-N-(4-{2-[4-(2,3-Dihydro-furo[3,2-c]pyridin-4-yl)-
piperazin-1-yl]-ethyl}-cyclohexyl)-3,3-dimethyl-butyra-
mide;
trans-2-Cyclobutyl-N-(4-{2-[4-(2,3-dihydro-furo[3,2-c]py-
ridin-4-yl)-piperazin-1-yl]-ethyl}-cyclohexyl)-acetamide;
trans-2,2-Difluoro-cyclopropanecarboxylic acid (4-{2-[4-(2,
3-dihydro-furo[3,2-c]pyridin-4-yl)-piperazin-1-yl]-
ethyl}-cyclohexyl)-amide;
trans-N-(4-{2-[4-(2,3-Dihydro-furo[3,2-c]pyridin-4-yl)-
piperazin-1-yl]-ethyl}-cyclohexyl)-isobutyramide;
trans-N-(4-{2-[4-(2,3-Dihydro-furo[3,2-c]pyridin-4-yl)-
piperazin-1-yl]-ethyl}-cyclohexyl)-rac-2-methyl-butyra-
mide;
trans-N-(4-{2-[4-(2,3-Dihydro-furo[3,2-c]pyridin-4-yl)-
piperazin-1-yl]-ethyl}-cyclohexyl)-2-oxetan-3-yl-aceta-
mide;
trans-3-(4-{2-[4-(2,3-Dihydro-furo[3,2-c]pyridin-4-yl)-pip-
erazin-1-yl]-ethyl}-cyclohexyl)-1,1-dimethyl-urea;
trans-N-(4-{2-[4-(2,3-Dihydro-furo[3,2-c]pyridin-4-yl)-
piperazin-1-yl]-ethyl}-cyclohexyl)-2,2,2-trifluoro-aceta-
mide;
3-Methyl-but-2-enoic acid trans-(4-{2-[4-(2,3-dihydro-furo
[3,2-c]pyridin-4-yl)-piperazin-1-yl]-ethyl}-cyclohexyl)-
amide;
(E)-Pent-3-enoic acid trans-(4-{2-[4-(2,3-dihydro-furo[3,2-
c]pyridin-4-yl)-piperazin-1-yl]-ethyl}-cyclohexyl)-
amide;
But-2-ynoic acid trans-(4-{2-[4-(2,3-dihydro-furo[3,2-c]py-
ridin-4-yl)-piperazin-1-yl]-ethyl}-cyclohexyl)-amide;
trans-N-(4-{2-[4-(2,3-Dihydro-furo[3,2-c]pyridin-4-yl)-
piperazin-1-yl]-ethyl}-cyclohexyl)-formamide;
trans-N-(4-{2-[4-(2,3-Dihydro-furo[3,2-c]pyridin-4-yl)-
piperazin-1-yl]-ethyl}-cyclohexyl)-2-(3-methyl-isoxazol-
5-yl)-acetamide;
3-Methyl-isoxazole-5-carboxylic acid trans-(4-{2-[4-(2,3-
dihydro-furo[3,2-c]pyridin-4-yl)-piperazin-1-yl]-ethyl}-
cyclohexyl)-amide;
trans-N-(4-{2-[4-(2,3-Dihydro-furo[3,2-c]pyridin-4-yl)-
piperazin-1-yl]-ethyl}-cyclohexyl)-N',N'-dimethyl-succi-
namide;
trans-N-(4-{2-[4-(2,3-Dihydro-furo[3,2-c]pyridin-4-yl)-
piperazin-1-yl]-ethyl}-cyclohexyl)-3-hydroxy-3-methyl-
butyramide;
trans-(R)—N-(4-{2-[4-(2,3-Dihydro-furo[3,2-c]pyridin-4-
yl)-piperazin-1-yl]-ethyl}-cyclohexyl)-4,4,4-trifluoro-3-
hydroxy-butyramide;
(S)-3-Hydroxy-pentanoic acid trans-(4-{2-[4-(2,3-dihydro-
furo[3,2-c]pyridin-4-yl)-piperazin-1-yl]-ethyl}-cyclo-
hexyl)-amide;
trans-N-(4-{2-[4-(2,3-Dihydro-furo[3,2-c]pyridin-4-yl)-
piperazin-1-yl]-ethyl}-cyclohexyl)-2-((1S,3S)-3-meth-
oxy-cyclopentyl)-acetamide;
trans-N-(4-{2-[4-(2,3-Dihydro-furo[3,2-c]pyridin-4-yl)-
piperazin-1-yl]-ethyl}-cyclohexyl)-2-((S)-4-hydroxy-tet-
rahydro-furan-2-yl)-acetamide;
trans-N-(4-{2-[4-(2,3-Dihydro-furo[3,2-c]pyridin-4-yl)-
piperazin-1-yl]-ethyl}-cyclohexyl)-butyramide;
4-Methyl-pentanoic acid trans-(4-{2-[4-(2,3-dihydro-furo[3,
2-c]pyridin-4-yl)-piperazin-1-yl]-ethyl}-cyclohexyl)-
amide;
Pentanoic acid trans-(4-{2-[4-(2,3-dihydro-furo[3,2-c]pyri-
din-4-yl)-piperazin-1-yl]-ethyl}-cyclohexyl)-amide;
trans-N-(4-{2-[4-(2,3-Dihydro-furo[3,2-c]pyridin-4-yl)-
piperazin-1-yl]-ethyl}-cyclohexyl)-4,4,4-trifluoro-bu-
tyramide;
trans-N-(4-{2-[4-(6-Methyl-furo[3,2-c]pyridin-4-yl)-piper-
azin-1-yl]-ethyl}-cyclohexyl)-acetamide;
trans-Tetrahydro-pyran-4-carboxylic acid (4-{2-[4-(6-me-
thyl-furo[3,2-c]pyridin-4-yl)-piperazin-1-yl]-ethyl}-cy-
clohexyl)-amide;
trans-N-(4-{2-[4-(6-Methyl-furo[3,2-c]pyridin-4-yl)-piper-
azin-1-yl]-ethyl}-cyclohexyl)-2-(tetrahydro-pyran-4-yl)-
acetamide;
trans-3-Methoxy-N-(4-{2-[4-(6-methyl-furo[3,2-c]pyridin-
4-yl)-piperazin-1-yl]-ethyl}-cyclohexyl)-propionamide;
trans-N-(4-{2-[4-(6-Methyl-2,3-dihydro-furo[3,2-c]pyridin-
4-yl)-piperazin-1-yl]-ethyl}-cyclohexyl)-acetamide
Tetrahydro-pyran-4-carboxylic acid trans-(4-{2-[4-(6-me-
thyl-2,3-dihydro-furo[3,2-c]pyridin-4-yl)-piperazin-1-
yl]-ethyl}-cyclohexyl)-amide;
trans-N-(4-{2-[4-(6-Methyl-2,3-dihydro-furo[3,2-c]pyridin-
4-yl)-piperazin-1-yl]-ethyl}-cyclohexyl)-2-(tetrahydro-
pyran-4-yl)-acetamide;
trans-3-Methoxy-N-(4-{2-[4-(6-methyl-2,3-dihydro-furo[3,
2-c]pyridin-4-yl)-piperazin-1-yl]-ethyl}-cyclohexyl)-pro-
pionamide;
trans-N-(4-{2-[4-(7-Methyl-furo[3,2-c]pyridin-4-yl)-piper-
azin-1-yl]-ethyl}-cyclohexyl)-acetamide;
trans-Tetrahydro-pyran-4-carboxylic acid (4-{2-[4-(7-me-
thyl-furo[3,2-c]pyridin-4-yl)-piperazin-1-yl]-ethyl}-cy-
clohexyl)-amide;
trans-N-(4-{2-[4-(7-Methyl-furo[3,2-c]pyridin-4-yl)-piper-
azin-1-yl]-ethyl}-cyclohexyl)-2-(tetrahydro-pyran-4-yl)-
acetamide;
trans-3-Methoxy-N-(4-{2-[4-(7-methyl-furo[3,2-c]pyridin-
4-yl)-piperazin-1-yl]-ethyl}-cyclohexyl)-propionamide;
trans-N-(4-{2-[4-(7-Methyl-2,3-dihydro-furo[3,2-c]pyridin-
4-yl)-piperazin-1-yl]-ethyl}-cyclohexyl)-acetamide;

Tetrahydro-pyran-4-carboxylic acid trans-(4-{2-[4-(7-methyl-2,3-dihydro-furo[3,2-c]pyridin-4-yl)-piperazin-1-yl]-ethyl}-cyclohexyl)-amide;

trans-N-(4-{2-[4-(7-Methyl-2,3-dihydro-furo[3,2-c]pyridin-4-yl)-piperazin-1-yl]-ethyl}-cyclohexyl)-2-(tetrahydro-pyran-4-yl)-acetamide;

trans-3-Methoxy-N-(4-{2-[4-(7-methyl-2,3-dihydro-furo[3,2-c]pyridin-4-yl)-piperazin-1-yl]-ethyl}-cyclohexyl)-propionamide;

trans-(RS)—N-(4-{2-[4-(2,3-Dihydro-furo[3,2-c]pyridin-4-yl)-piperazin-1-yl]-ethyl}-cyclohexyl)-3,3,3-trifluoro-2-hydroxy-propionamide;

trans-N-(4-{2-[4-(2,3-Dihydro-furo[3,2-c]pyridin-4-yl)-piperazin-1-yl]-ethyl}-cyclohexyl)-3,3-dimethoxy-propionamide;

trans-N-(4-{2-[4-(2,3-Dihydro-furo[3,2-c]pyridin-4-yl)-piperazin-1-yl]-ethyl}-cyclohexyl)-4,4-dimethoxy-butyramide;

5-Methanesulfonyl-thiophene-2-carboxylic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-6-methyl-nicotinamide;

trans-4-Cyano-N-(4-{2-[4-(2,3-dihydro-furo[3,2-c]pyridin-4-yl)-piperazin-1-yl]-ethyl}-cyclohexyl)-benzamide;

trans-N-(4-{2-[4-(2,3-Dihydro-furo[3,2-c]pyridin-4-yl)-piperazin-1-yl]-ethyl}-cyclohexyl)-4-(4-methyl-piperazin-1-yl)-benzamide;

trans-N-(4-{2-[4-(2,3-Dihydro-furo[3,2-c]pyridin-4-yl)-piperazin-1-yl]-ethyl}-cyclohexyl)-6-morpholin-4-yl-nicotinamide;

trans-N-(4-{2-[4-(2,3-Dihydro-furo[3,2-c]pyridin-4-yl)-piperazin-1-yl]-ethyl}-cyclohexyl)-4-pyridin-3-yl-benzamide;

Benzo[1,3]dioxole-5-carboxylic acid trans-(4-{2-[4-(2,3-dihydro-furo[3,2-c]pyridin-4-yl)-piperazin-1-yl]-ethyl}-cyclohexyl)-amide;

trans-2-Benzo[1,3]dioxol-5-yl-N-(4-{2-[4-(2,3-dihydro-furo[3,2-c]pyridin-4-yl)-piperazin-1-yl]-ethyl}-cyclohexyl)-acetamide;

1-Hydroxy-cyclobutanecarboxylic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-2-hydroxy-2-methyl-propionamide;

trans-N-(4-{2-[4-(2,3-Dihydro-furo[3,2-c]pyridin-4-yl)-piperazin-1-yl]-ethyl}-cyclohexyl)-4-(1,2-dioxo-1λ6-thiomorpholin-4-yl)-benzamide;

trans-N-(4-{2-[4-(2,3-Dihydro-furo[3,2-c]pyridin-4-yl)-piperazin-1-yl]-ethyl}-cyclohexyl)-4-pyrazol-1-yl-benzamide;

trans-N-(4-{2-[4-(2,3-Dihydro-furo[3,2-c]pyridin-4-yl)-piperazin-1-yl]-ethyl}-cyclohexyl)-3-(5-methyl-[1,2,4]oxadiazol-3-yl)-benzamide;

Quinoline-6-carboxylic acid trans-(4-{2-[4-(2,3-dihydro-furo[3,2-c]pyridin-4-yl)-piperazin-1-yl]-ethyl}-cyclohexyl)-amide;

trans-2-Benzo[d]isoxazol-3-yl-N-(4-{2-[4-(2,3-dihydro-furo[3,2-c]pyridin-4-yl)-piperazin-1-yl]-ethyl}-cyclohexyl)-acetamide;

5-Morpholin-4-yl-pyrazine-2-carboxylic acid trans-(4-{2-[4-(2,3-dihydro-furo[3,2-c]pyridin-4-yl)-piperazin-1-yl]-ethyl}-cyclohexyl)-amide;

trans-4-tert-Butyl-N-(4-{2-[4-(2,3-dihydro-furo[3,2-c]pyridin-4-yl)-piperazin-1-yl]-ethyl}-cyclohexyl)-benzamide;

trans-2,4-Dichloro-N-(4-{2-[4-(2,3-dihydro-furo[3,2-c]pyridin-4-yl)-piperazin-1-yl]-ethyl}-cyclohexyl)-benzamide;

trans-N-(4-{2-[4-(2,3-Dihydro-furo[3,2-c]pyridin-4-yl)-piperazin-1-yl]-ethyl}-cyclohexyl)-4-pyrrol-1-yl-benzamide;

Biphenyl-4-carboxylic acid trans-(4-{2-[4-(2,3-dihydro-furo[3,2-c]pyridin-4-yl)-piperazin-1-yl]-ethyl}-cyclohexyl)-amide;

trans-(R)—N-(4-{2-[4-(2,3-Dihydro-furo[3,2-c]pyridin-4-yl)-piperazin-1-yl]-ethyl}-cyclohexyl)-2-methoxy-propionamide;

trans-4-tert-Butoxy-N-(4-{2-[4-(2,3-dihydro-furo[3,2-c]pyridin-4-yl)-piperazin-1-yl]-ethyl}-cyclohexyl)-benzamide;

trans-(S)—N-(4-{2-[4-(2,3-Dihydro-furo[3,2-c]pyridin-4-yl)-piperazin-1-yl]-ethyl}-cyclohexyl)-2-methoxy-propionamide;

trans-N-(4-{2-[4-(2,3-Dihydro-furo[3,2-c]pyridin-4-yl)-piperazin-1-yl]-ethyl}-cyclohexyl)-benzenesulfonamide;

trans-N-(4-{2-[4-(2,3-Dihydro-furo[3,2-c]pyridin-4-yl)-piperazin-1-yl]-ethyl}-cyclohexyl)-3-methoxy-butyramide;

(R)-3-Hydroxy-pentanoic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-2-(1-hydroxy-cyclobutyl)-acetamide; and pharmaceutically acceptable salts and esters thereof.

Particular compounds of formula (I) of present invention are those selected from the group consisting of:

N-{trans-4-[2-(4-Furo[3,2-c]pyridin-4-yl-piperazin-1-yl)-ethyl]-cyclohexyl}-acetamide;

N-{trans-4-[2-(4-Furo[3,2-c]pyridin-4-yl-piperazin-1-yl)-ethyl]-cyclohexyl}-propionamide;

N-{trans-4-[2-(4-Furo[3,2-c]pyridin-4-yl-piperazin-1-yl)-ethyl]-cyclohexyl}-3-hydroxy-propionamide;

N-{trans-4-[2-(4-Thieno[3,2-c]pyridin-4-yl-piperazin-1-yl)-ethyl]-cyclohexyl}-acetamide;

N-{trans-4-[2-(4-Thieno[3,2-c]pyridin-4-yl-piperazin-1-yl)-ethyl]-cyclohexyl}-propionamide;

3-Methoxy-N-{trans-4-[2-(4-thieno[3,2-c]pyridin-4-yl-piperazin-1-yl)-ethyl]-cyclohexyl}-propionamide;

2-(trans-4-Methoxy-cyclohexyl)-N-{trans-4-[2-(4-thieno[3,2-c]pyridin-4-yl-piperazin-1-yl)-ethyl]-cyclohexyl}-acetamide;

2-Methoxy-N-{trans-4-[2-(4-thieno[3,2-c]pyridin-4-yl-piperazin-1-yl)-ethyl]-cyclohexyl}-acetamide;

2-(Tetrahydro-pyran-4-yl)-N-{trans-4-[2-(4-thieno[3,2-c]pyridin-4-yl-piperazin-1-yl)-ethyl]-cyclohexyl}-acetamide;

Tetrahydro-pyran-4-carboxylic acid {trans-4-[2-(4-thieno[3,2-c]pyridin-4-yl-piperazin-1-yl)-ethyl]-cyclohexyl}-amide;

2-((1R,3R)-3-Methoxy-cyclopentyl)-N-{trans-4-[2-(4-thieno[3,2-c]pyridin-4-yl-piperazin-1-yl)-ethyl]-cyclohexyl}-acetamide;

2-((1S,3S)-3-Methoxy-cyclopentyl)-N-{trans-4-[2-(4-thieno[3,2-c]pyridin-4-yl-piperazin-1-yl)-ethyl]-cyclohexyl}-acetamide;

2-Hydroxy-N-{trans-4-[2-(4-thieno[3,2-c]pyridin-4-yl-piperazin-1-yl)-ethyl]-cyclohexyl}-acetamide;

2-(trans-4-Hydroxy-cyclohexyl)-N-{trans-4-[2-(4-thieno[3,2-c]pyridin-4-yl-piperazin-1-yl)-ethyl]-cyclohexyl}-acetamide;

N-{trans-4-[2-(4-Thieno[3,2-c]pyridin-4-yl-piperazin-1-yl)-ethyl]-cyclohexyl}-methanesulfonamide;
Ethanesulfonic acid {trans-4-[2-(4-thieno[3,2-c]pyridin-4-yl-piperazin-1-yl)-ethyl]-cyclohexyl}-amide;
trans-N-(4-{2-[4-(2,3-Dihydro-furo[3,2-c]pyridin-4-yl)-piperazin-1-yl]-ethyl}-cyclohexyl)-acetamide;
trans-N-(4-{2-[4-(2,3-Dihydrofuro[3,2-c]pyridin-4-yl)-piperazin-1-yl]-ethyl}-cyclohexyl)-2-(tetrahydro-2H-pyran-4-yl)-acetamide;
trans-N-(4-{2-[4-(2,3-Dihydrofuro[3,2-c]pyridin-4-yl)-piperazin-1-yl]-ethyl}-cyclohexyl)-3-methoxypropanamide;
trans-N-(4-{2-[4-(2,3-Dihydrofuro[3,2-c]pyridin-4-yl)-piperazin-1-yl]-ethyl}-cyclohexyl)-propionamide;
trans-N-(4-{2-[4-(2,3-Dihydrofuro[3,2-c]pyridin-4-yl)-piperazin-1-yl]-ethyl}-cyclohexyl)-2-(rac-1,4-dioxan-2-yl)-acetamide;
trans-N-(4-{2-[4-(2,3-Dihydrofuro[3,2-c]pyridin-4-yl)-piperazin-1-yl]-ethyl}-cyclohexyl)-methylsulfonyl-acetamide;
trans-N-(4-{2-[4-(2,3-Dihydrofuro[3,2-c]pyridin-4-yl)-piperazin-1-yl]-ethyl}-cyclohexyl)-hydroxyacetamide;
trans-N-(4-{2-[4-(2,3-Dihydrofuro[3,2-c]pyridin-4-yl)-piperazin-1-yl]-ethyl}-cyclohexyl)-rac-tetrahydrofuran-3-carboxamide;
trans-N-(4-{2-[4-(2,3-Dihydro-furo[3,2-c]pyridin-4-yl)-piperazin-1-yl]-ethyl}-cyclohexyl)-benzamide;
trans-N-(4-{2-[4-(2,3-Dihydro-furo[3,2-c]pyridin-4-yl)-piperazin-1-yl]-ethyl}-cyclohexyl)-4-fluoro-benzamide;
Ethanesulfonic acid trans-(4-{2-[4-(2,3-dihydro-furo[3,2-c]pyridin-4-yl)-piperazin-1-yl]-ethyl}-cyclohexyl)-amide;
trans-2-Cyclopropyl-N-(4-{2-[4-(2,3-dihydro-furo[3,2-c]pyridin-4-yl)-piperazin-1-yl]-ethyl}-cyclohexyl)-acetamide;
Cyclobutanecarboxylic acid trans-(4-{2-[4-(2,3-dihydro-furo[3,2-c]pyridin-4-yl)-piperazin-1-yl]-ethyl}-cyclohexyl)-amide;
trans-N-(4-{2-[4-(2,3-Dihydro-furo[3,2-c]pyridin-4-yl)-piperazin-1-yl]-ethyl}-cyclohexyl)-4-morpholin-4-yl-benzamide;
trans-2-Cyano-N-(4-{2-[4-(2,3-dihydro-furo[3,2-c]pyridin-4-yl)-piperazin-1-yl]-ethyl}-cyclohexyl)-acetamide;
trans-N-(4-{2-[4-(2,3-Dihydro-furo[3,2-c]pyridin-4-yl)-piperazin-1-yl]-ethyl}-cyclohexyl)-3,3,3-trifluoro-propionamide;
trans-N-(4-{2-[4-(2,3-Dihydro-furo[3,2-c]pyridin-4-yl)-piperazin-1-yl]-ethyl}-cyclohexyl)-2-(R)-[1,4]dioxan-2-yl-acetamide;
Quinoline-4-carboxylic acid trans-(4-{2-[4-(2,3-dihydro-furo[3,2-c]pyridin-4-yl)-piperazin-1-yl]-ethyl}-cyclohexyl)-amide;
Cyclopropanecarboxylic acid trans-(4-{2-[4-(2,3-dihydro-furo[3,2-c]pyridin-4-yl)-piperazin-1-yl]-ethyl}-cyclohexyl)-amide;
trans-N-(4-{2-[4-(2,3-Dihydro-furo[3,2-c]pyridin-4-yl)-piperazin-1-yl]-ethyl}-cyclohexyl)-2-trans-(4-methoxy-cyclohexyl)-acetamide;
trans-N-(4-{2-[4-(2,3-Dihydro-furo[3,2-c]pyridin-4-yl)-piperazin-1-yl]-ethyl}-cyclohexyl)-2-(S)-[1,4]dioxan-2-yl-acetamide;
trans-N-(4-{2-[4-(2,3-Dihydro-furo[3,2-c]pyridin-4-yl)-piperazin-1-yl]-ethyl}-cyclohexyl)-2-(S)-(tetrahydro-furan-2-yl)-acetamide;
trans-N-(4-{2-[4-(2,3-Dihydro-furo[3,2-c]pyridin-4-yl)-piperazin-1-yl]-ethyl}-cyclohexyl)-3-methyl-butyramide;
trans-N-(4-{2-[4-(2,3-Dihydro-furo[3,2-c]pyridin-4-yl)-piperazin-1-yl]-ethyl}-cyclohexyl)-3,3-dimethyl-butyramide;
trans-2-Cyclobutyl-N-(4-{2-[4-(2,3-dihydro-furo[3,2-c]pyridin-4-yl)-piperazin-1-yl]-ethyl}-cyclohexyl)-acetamide;
trans-N-(4-{2-[4-(2,3-Dihydro-furo[3,2-c]pyridin-4-yl)-piperazin-1-yl]-ethyl}-cyclohexyl)-isobutyramide;
trans-N-(4-{2-[4-(2,3-Dihydro-furo[3,2-c]pyridin-4-yl)-piperazin-1-yl]-ethyl}-cyclohexyl)-rac-2-methyl-butyramide;
trans-N-(4-{2-[4-(2,3-Dihydro-furo[3,2-c]pyridin-4-yl)-piperazin-1-yl]-ethyl}-cyclohexyl)-2-oxetan-3-yl-acetamide;
(E)-Pent-3-enoic acid trans-(4-{2-[4-(2,3-dihydro-furo[3,2-c]pyridin-4-yl)-piperazin-1-yl]-ethyl}-cyclohexyl)-amide;
But-2-ynoic acid trans-(4-{2-[4-(2,3-dihydro-furo[3,2-c]pyridin-4-yl)-piperazin-1-yl]-ethyl}-cyclohexyl)-amide;
trans-N-(4-{2-[4-(2,3-Dihydro-furo[3,2-c]pyridin-4-yl)-piperazin-1-yl]-ethyl}-cyclohexyl)-2-(3-methyl-isoxazol-5-yl)-acetamide;
trans-N-(4-{2-[4-(2,3-Dihydro-furo[3,2-c]pyridin-4-yl)-piperazin-1-yl]-ethyl}-cyclohexyl)-3-hydroxy-3-methyl-butyramide;
trans-N-(4-{2-[4-(2,3-Dihydro-furo[3,2-c]pyridin-4-yl)-piperazin-1-yl]-ethyl}-cyclohexyl)-2-((1S,3S)-3-methoxy-cyclopentyl)-acetamide;
trans-N-(4-{2-[4-(2,3-Dihydro-furo[3,2-c]pyridin-4-yl)-piperazin-1-yl]-ethyl}-cyclohexyl)-2-((S)-4-hydroxy-tetrahydro-furan-2-yl)-acetamide;
trans-N-(4-{2-[4-(2,3-Dihydro-furo[3,2-c]pyridin-4-yl)-piperazin-1-yl]-ethyl}-cyclohexyl)-butyramide;
4-Methyl-pentanoic acid trans-(4-{2-[4-(2,3-dihydro-furo[3,2-c]pyridin-4-yl)-piperazin-1-yl]-ethyl}-cyclohexyl)-amide;
Pentanoic acid trans-(4-{2-[4-(2,3-dihydro-furo[3,2-c]pyridin-4-yl)-piperazin-1-yl]-ethyl}-cyclohexyl)-amide;
trans-N-(4-{2-[4-(7-Methyl-furo[3,2-c]pyridin-4-yl)-piperazin-1-yl]-ethyl}-cyclohexyl)-acetamide;
trans-N-(4-{2-[4-(2,3-Dihydro-furo[3,2-c]pyridin-4-yl)-piperazin-1-yl]-ethyl}-cyclohexyl)-3,3-dimethoxy-propionamide;
5-Methanesulfonyl-thiophene-2-carboxylic acid trans-(4-{2-[4-(2,3-dihydro-furo[3,2-c]pyridin-4-yl)-piperazin-1-yl]-ethyl}-cyclohexyl)-amide;
Benzo[1,3]dioxole-5-carboxylic acid trans-(4-{2-[4-(2,3-dihydro-furo[3,2-c]pyridin-4-yl)-piperazin-1-yl]-ethyl}-cyclohexyl)-amide;
Quinoline-6-carboxylic acid trans-(4-{2-[4-(2,3-dihydro-furo[3,2-c]pyridin-4-yl)-piperazin-1-yl]-ethyl}-cyclohexyl)-amide;
trans-2-Benzo[d]isoxazol-3-yl-N-(4-{2-[4-(2,3-dihydro-furo[3,2-c]pyridin-4-yl)-piperazin-1-yl]-ethyl}-cyclohexyl)-acetamide;
Biphenyl-4-carboxylic acid trans-(4-{2-[4-(2,3-dihydro-furo[3,2-c]pyridin-4-yl)-piperazin-1-yl]-ethyl}-cyclohexyl)-amide; and
pharmaceutically acceptable salts and esters thereof.

Particular compounds of formula (I) of present invention are those selected from the group consisting of:

trans-N-(4-{2-[4-(2,3-Dihydro-furo[3,2-c]pyridin-4-yl)-piperazin-1-yl]-ethyl}-cyclohexyl)-acetamide;

trans-N-(4-{2-[4-(2,3-Dihydrofuro[3,2-c]pyridin-4-yl)-piperazin-1-yl]-ethyl}-cyclohexyl)-propionamide;

trans-N-(4-{2-[4-(2,3-Dihydrofuro[3,2-c]pyridin-4-yl)-piperazin-1-yl]-ethyl}-cyclohexyl)-2-(rac-1,4-dioxan-2-yl)-acetamide;

trans-N-(4-{2-[4-(2,3-Dihydrofuro[3,2-c]pyridin-4-yl)-piperazin-1-yl]-ethyl}-cyclohexyl)-methylsulfonyl-acetamide;

trans-N-(4-{2-[4-(2,3-Dihydrofuro[3,2-c]pyridin-4-yl)-piperazin-1-yl]-ethyl}-cyclohexyl)-hydroxyacetamide;

trans-N-(4-{2-[4-(2,3-Dihydrofuro[3,2-c]pyridin-4-yl)-piperazin-1-yl]-ethyl}-cyclohexyl)-rac-tetrahydrofuran-3-carboxamide;

trans-2-Cyclopropyl-N-(4-{2-[4-(2,3-dihydro-furo[3,2-c]pyridin-4-yl)-piperazin-1-yl]-ethyl}-cyclohexyl)-acetamide;

Cyclobutanecarboxylic acid trans-(4-{2-[4-(2,3-dihydro-furo[3,2-c]pyridin-4-yl)-piperazin-1-yl]-ethyl}-cyclohexyl)-amide;

trans-2-Cyano-N-(4-{2-[4-(2,3-Dihydro-furo[3,2-c]pyridin-4-yl)-piperazin-1-yl]-ethyl}-cyclohexyl)-acetamide;

trans-N-(4-{2-[4-(2,3-Dihydro-furo[3,2-c]pyridin-4-yl)-piperazin-1-yl]-ethyl}-cyclohexyl)-3,3,3-trifluoro-propionamide;

trans-N-(4-{2-[4-(2,3-Dihydro-furo[3,2-c]pyridin-4-yl)-piperazin-1-yl]-ethyl}-cyclohexyl)-2-(R)-[1,4]dioxan-2-yl-acetamide;

Cyclopropanecarboxylic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-isobutyramide; and pharmaceutically acceptable salts and esters thereof.

The invention further relates to a process for the manufacture of compounds of formula (I) as defined above. Compounds of formula (I) can be prepared following standard methods comprising:

a) the reaction of a compound of formula (V)

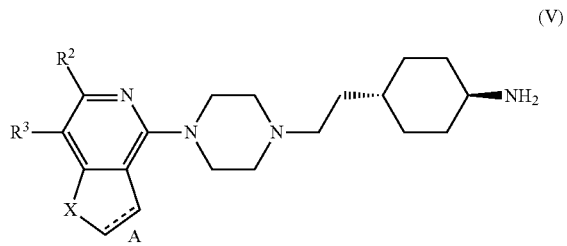

with a compound of formula $R^1C(O)OH$, $R^1C(O)OR$ or $R^1S(O)_2Cl$, wherein X, A, $R^1$, $R^2$ and $R^3$ are as defined above and R is $C_{1-7}$ alkyl; or b) the reaction of a compound of formula (II)

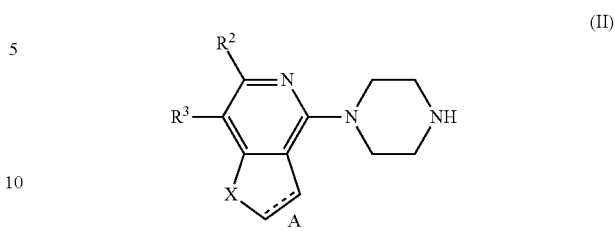

with a compound of formula (VI)

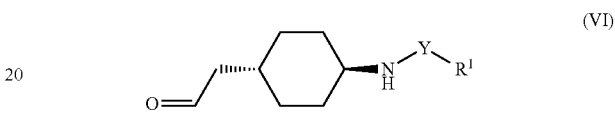

wherein X, Y, A, $R^1$, $R^2$ and $R^3$ are as defined above.

Particularly, compounds of formula (I) can be prepared following standard methods in accordance with Schemes 1 or 2.

According to Scheme 1, in a first step, a compound of formula (II) is reacted with an aldehyde of formula (III) under reductive amination conditions such as for example the use of sodium triacetoxyborohydride (Na(AcO)$_3$BH) in a solvent such as 1,2-dichloroethane in the presence of methanol (MeOH) or an acid such as acetic acid (AcOH) to give a compound of formula (IV). The amino moiety of aldehyde (III) is protected with an amino-protecting group such as a Boc moiety.

In a second step, compounds of formula (IV) are deprotected to give compounds of formula (V). In such cases where the amino-protecting group is a Boc functionality, compounds of formula (IV) can be reacted with an acid as for example HCl in an appropriate solvent mixture such as ethylacetate (AcOEt) and MeOH to give primary amines isolated as the HCl salts (V).

Compounds of formula (V) can be reacted in a third step with a number of different nucleophiles to obtain compounds of formula (I). For instance reaction of compounds of formula (V) with a carboxylic acid of general structure $R^1C(O)OH$ in the presence of a coupling agent such as 0-(benzotriazol-1-yl)-N,N,N',N'-tetramethyluronium tetrafluoroborate (TBTU) and a base such as Hunig's base (N,N-Diisopropylethylamine, DIPEA) in a solvent such as dimethylformamide (DMF) leads to compounds of formula (I'). In some instances carboxylic acids of general structure $R^1C(O)OH$ or their salts can be prepared by saponification of an ester of formula $R^1C(O)OR$, wherein R is $C_{1-7}$ alkyl, with a reagent such as a base like LiOH or mild reagents like potassium trimethylsilanolate (KOSiMe$_3$) in a solvent such as dichloromethane (DCM) followed by full evaporation of all solvent and direct use of the crude in the amide coupling step described above to obtain compounds of formula (I'). Yet in another instance, compounds of formula (V) can be reacted with an appropriate reagent of general structure $R^1S(O)_2Cl$ in the presence of a base such as triethylamine (Et$_3$N) in a solvent such as DCM to obtain compounds of formula (I").

Derivatization at the primary amine does not necessarily need to be carried out in a last step, but can occur already prior to the reductive amination step, thus avoiding the use of an amino-protecting group. As can be seen from Scheme 2, the reductive amination of a compound of formula (II) with an aldehyde of formula (VI') under conditions well known to the person skilled in the art, will directly lead to an amide of formula (I'). An example for appropriate conditions for this step is the use of Na(AcO)$_3$BH in a solvent such as 1,2-dichloroethane in the presence or not of MeOH or an acid such as AcOH. Methods to generate compounds of formula (VI') have been described (e.g. WO 2007/093540).

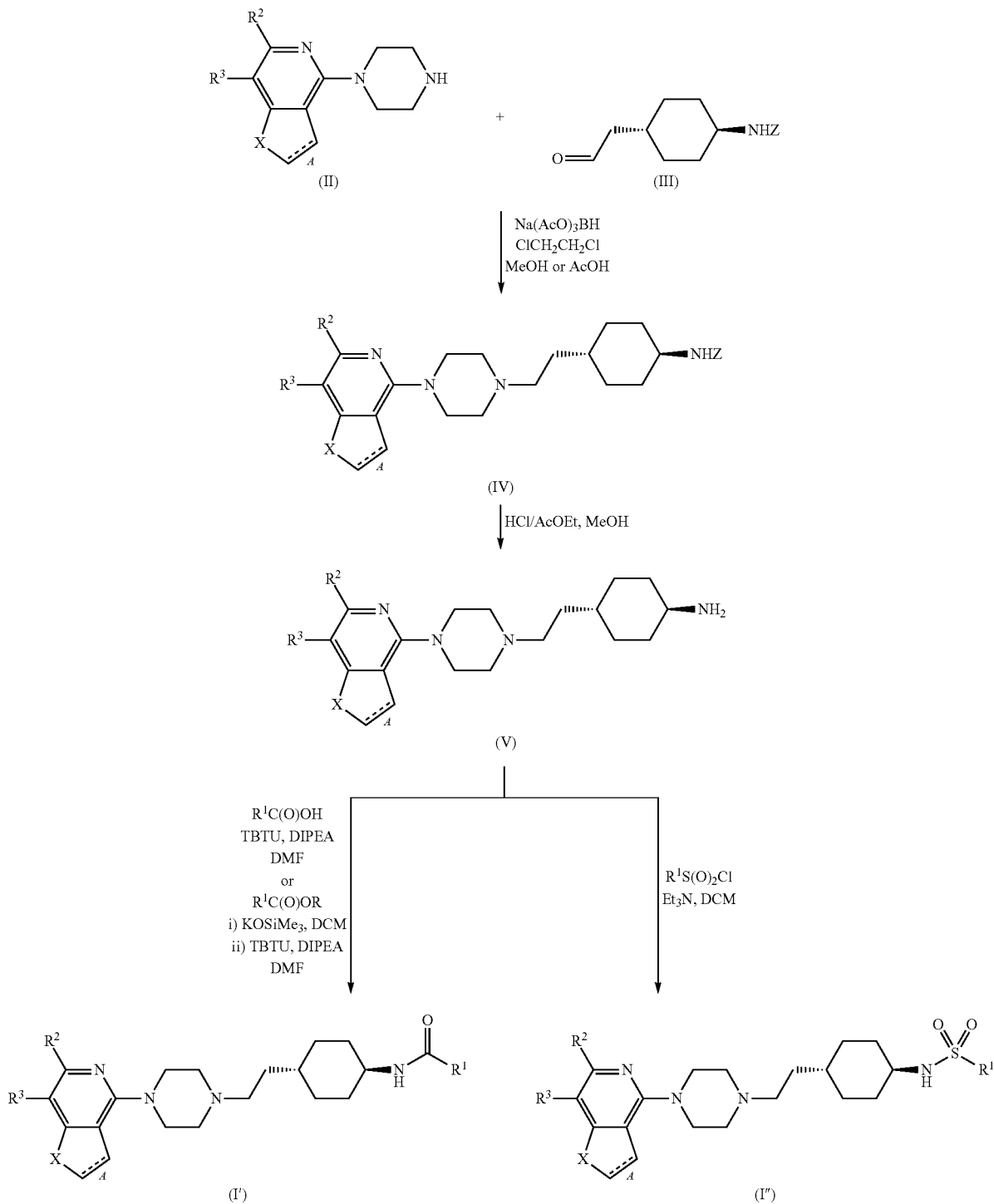

Scheme 1.

wherein X, A, R$^1$, R$^2$ and R$^3$ are as defined above, Z is an amino-protecting group and R is C$_{1-7}$ alkyl.

Scheme 2,

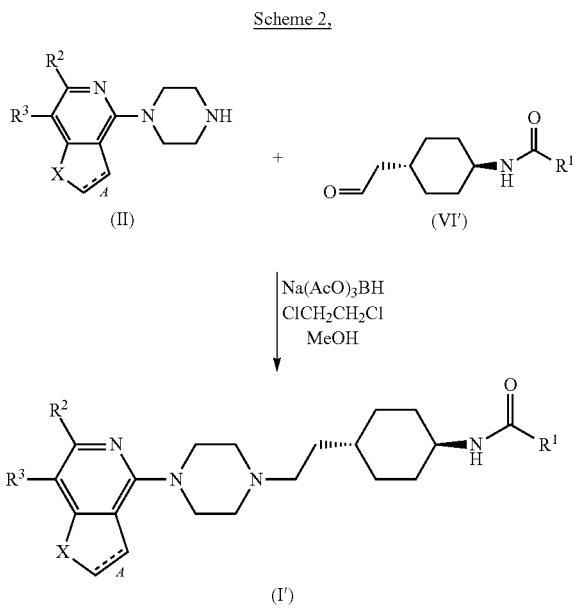

wherein X, A, $R^1$, $R^2$ and $R^3$ are as defined above.

In some occasions the starting materials (II) might need to be synthesized as they are not commercially available. For example compounds of formula (IIc) (Scheme 3) can be obtained from compounds of formula (IIa) by hydrogenation under conditions well known to the person skilled in the art. For instance a catalyst such as Pd/C can be used in presence of an acid such as AcOH in a solvent such as MeOH. In other occasions an alternative reducing agent (like $NaBH_4$) could be used particularly in cases where $R^2$ and/or $R^3$=halogen.

Scheme 3,

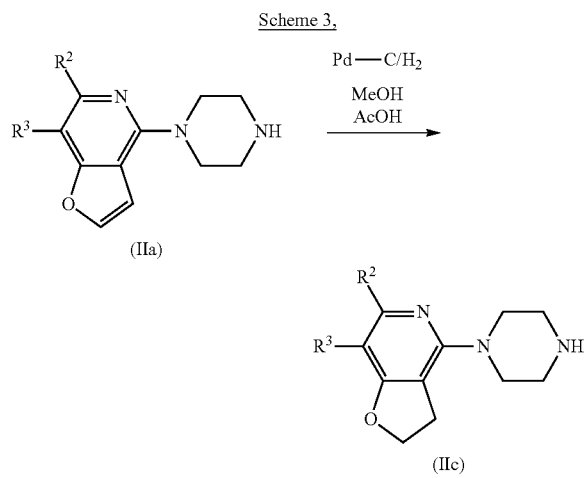

wherein X, A, $R^1$, $R^2$ and $R^3$ are as defined above.

The corresponding salts compounds of formula (I) with acids can be obtained by standard methods known to the person skilled in the art, e.g. by dissolving the compound of formula (I) in a suitable solvent such as e.g. dioxan or tetrahydrofuran (THF) and adding an appropriate amount of the corresponding acid. The products can usually be isolated by filtration or by chromatography.

The conversion of compounds of formula (I) into pharmaceutically acceptable esters can be carried out e.g. by treatment of a suitable hydroxy-group present in the molecule with a suitable carboxylic acid using e.g. a condensating reagent such as benzotriazol-1-yloxytris(dimethylamino) phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluoroborate (TPTU).

Insofar as their preparation is not described in the examples, the compounds of formula (I) as well as all intermediate products can be prepared according to analogous methods or according to the methods set forth above. Starting materials are commercially available, known in the art or can be prepared by methods known in the art or in analogy thereto.

The present invention also relates to compounds of formula (I) as defined above, when prepared by a process as described above.

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention can be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention can be administered in any convenient administrative form, e.g., tablets, powders, capsules, solutions, dispersions, suspensions, syrups, sprays, suppositories, gels, emulsions, patches, etc. Such compositions can comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R. et al., *Remington: The Science and Practice of Pharmacy* (2000) Lippincott, Williams & Wilkins, Philadelphia; and Rowe R. C, *Handbook of Pharmaceutical Excipients* (2005) Pharmaceutical Press, Chicago. The formulations can also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.1 to 1000 mg per person of a compound of formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution can be filtered, e.g., using a 0.2 μm filter, to remove impurities and contaminants.

As described above, the novel compounds of the present invention and their pharmaceutically acceptable salts and esters possess valuable pharmacological properties and have been found to be dual modulators of the 5-HT$_{2A}$ and D$_3$ receptors. The compounds of the present invention can therefore be used, either alone or in combination with other drugs, for the treatment or prevention of diseases which are modulated by ligands of the 5-HT$_{2A}$ or D$_3$ receptors. These diseases include, but are not limited to psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

The invention therefore also relates to pharmaceutical compositions comprising a compound as defined above and a pharmaceutically acceptable excipient.

The invention likewise embraces compounds as described above for use as therapeutically active substances, especially as therapeutically active substances for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

In another embodiment, the invention relates to a method for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions, which method comprises administering a compound as defined above to a human being or animal.

The invention also embraces the use of compounds as defined above for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions.

The invention also relates to the use of compounds as described above for the preparation of medicaments for the treatment or prevention of diseases which are related to the 5-HT$_{2A}$ or D$_3$ receptors, particularly for the treatment or prevention of psychotic disorders, depression, anxiety, drug addiction, attention deficit hyperactivity disorders, dementia and memory impairment, wherein psychotic disorders include schizophrenia, positive, negative and/or cognitive symptoms associated with schizophrenia, schizoaffective disorders, bipolar disease, mania, psychotic depression, and other psychoses involving paranoia and delusions. Such medicaments comprise a compound as described above.

Particularly, compounds of present invention can be used in the treatment or prevention of psychotic disorders including schizophrenia as well as positive, negative and/or cognitive symptoms associated with schizophrenia.

The invention will be more fully understood by reference to the following examples. They should not, however, be construed as limiting the scope of the invention.

INTERMEDIATES

Intermediate A trans-4-[2-(4-Furo[3,2-c]pyridin-4-yl-piperazin-1-yl)-ethyl]-cyclohexylamine trihydrochloride

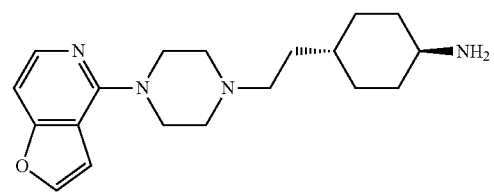 [SMILES: N[C@H]1CC[C@H](CCN2CCN(c3nccc4occc34)CC2)CC1]

Step A trans-[4-(2-oxo-ethyl)-cyclohexyl]-carbamic acid tert-butyl ester [CAS-Nr. 215790-29-7] (4.1 g, 17 mmol) was added to a solution under N$_2$ of commercially available 4-piperazine-1-yl-furo[3,2-c]pyridine [CAS-Nr. 81078-84-4] (3.1 g, 15 mmol) in 1,2-dichloroethane (40 ml) and MeOH (0.5 ml). The resulting yellow solution was stirred 8 h at room temperature before addition of Na(AcO)$_3$BH (4.9 g, 23 mmol). Stirring was continued at room temperature for 18 h. The reaction mixture was poured on sat. aq. NaHCO$_3$ sol. (130 ml) and the product was extracted with EtOAc (3×100 ml). The combined organic layers were washed with H$_2$O (130 ml) and brine (100 ml). After drying (MgSO$_4$) the solvent was evaporated and the product was purified by flash chromatography on silica gel (CH$_2$Cl$_2$/MeOH, 100:0 to 95:5) to yield trans-{4-[2-(4-furo[3,2-c]pyridin-4-yl-piperazin-1-yl)-ethyl]-cyclohexyl}-carbamic acid tert-butyl ester as white crystals (3.4 g, 52%), MS (ISP) m/z=429.4 [(M+H)$^+$].

Step B trans-{4-[2-(4-Furo[3,2-c]pyridin-4-yl-piperazin-1-yl)-ethyl]-cyclohexyl}-carbamic acid tert-butyl ester (2.9 g, 7 mmol) was treated with 1 N HCl in EtOAc (100 ml, 100 mmol) and MeOH (1.9 ml) and the resulting mixture was stirred over night at room temperature. A white precipitate was formed that was collected by filtration and washed with EtOAc. The solid was dried over night under high vacuum to yield trans-4-[2-(4-furo[3,2-c]pyridin-4-yl-piperazin-1-yl)-ethyl]-cyclohexylamine trihydrochloride as a white powder (2.9 g, 96%), MS (ISP) m/z=329.1 [(M+H)$^+$].

Intermediate B trans-4-[2-(4-Thieno[3,2-c]pyridin-4-yl-piperazin-1-yl)-ethyl]-cyclohexylamine trihydrochloride

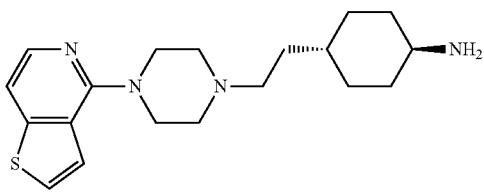

Step A trans-[4-(2-oxo-ethyl)-cyclohexyl]-carbamic acid tert-butyl ester [CAS-Nr. 215790-29-7] (1.0 g, 4 mmol) was added to a solution under N$_2$ of commercially available 4-piperazine-1-yl-thieno[3,2-c]pyridine [CAS-Nr. 106261-27-2] (0.85 g, 4 mmol) in 1,2-dichloroethane (45 ml) and AcOH (0.22 ml, 4 mmol). The resulting reaction mixture was stirred 8 h at room temperature before addition of Na(AcO)$_3$BH (1.2 g, 6 mmol). Stirring was continued over night at room temperature. Sat. aq. NaHCO$_3$ sol. was added and the product was extracted with EtOAc (2×). The combined organic layers were washed with H$_2$O and brine. After drying (MgSO$_4$) the solvent was evaporated and the product was purified by flash chromatography on silica gel (CH$_2$Cl$_2$/MeOH, 100:0 to 90:10) to yield trans-{4-[2-(4-thieno[3,2-c]pyridin-4-yl-piperazin-1-yl)-ethyl]-cyclohexyl}-carbamic acid tert-butyl ester as a light yellow solid (1.2 g, 72%), MS (ISP) m/z=445.3 [(M+H)$^+$].

Step B

{trans-4-[2-(4-Thieno[3,2-c]pyridin-4-yl-piperazin-1-yl)-ethyl]-cyclohexyl}-carbamic acid tert-butyl ester (1.2 g, 3 mmol) was treated with 1 N HCl in EtOAc (40 ml, 40 mmol) and MeOH (0.74 ml) and the resulting mixture was stirred 4 h at room temperature. A white precipitate was formed that was collected by filtration and washed with EtOAc. The solid was dried over night under high vacuum to yield trans-4-[2-(4-thieno[3,2-c]pyridin-4-yl-piperazin-1-yl)-ethyl]-cyclo-hexylamine trihydrochloride as a white powder (1.2 g, 94%), MS (ISP) m/z=345.1 [(M+H)$^+$].

Intermediate C trans-4-{2-[4-(2,3-Dihydrofuro[3,2-c]pyridin-4-yl)-piperazin-1-yl]-ethyl}-cyclohexanamine trihydrochloride

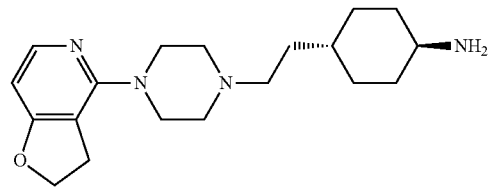 [SMILES: N[C@H]1CC[C@H](CCN2CCN(c3nccc4c3CCO4)CC2)CC1]

Step A

A mixture of commercially available 4-(piperazin-1-yl)-furo[3,2-c]pyridine [CAS-No. 81078-84-4] (1 g, 4.92 mmol), Pd/C 5% (0.46 g, 4.32 mmol), acetic acid (2.3 ml) in MeOH (6.9 ml) was stirred in a hydrogen atmosphere at room temperature for 48 h. After removal of the catalyst by filtration the mixture was evaporated, the residue was dissolved in dichloromethane/MeOH/NH$_4$OH 80:10:1, washed with 2N sodium carbonate solution, dried (MgSO$_4$) and evaporated. The crude material (0.68 g) was purified by chromatography on silica gel (dichloromethane/MeOH/NH$_4$OH 80:10:1) to yield 4-(piperazin-1-yl)-2,3-dihydrofuro[3,2-c]pyridine as a white solid (0.39 g, 39%), MS (ISP) m/z=206.2 [(M+H)$^+$], mp 89.5° C.

Step B

To a solution of 4-(piperazin-1-yl)-2,3-dihydrofuro[3,2-c]pyridine (0.38 g, 1.85 mmol) in dichloromethane (11 ml) and MeOH (0.3 ml) was added at room temperature commercially available trans-tert-butyl-4-(2-oxoethyl)-cyclohexylcarbamate (596 mg, 2.22 mmol) and triethylamine (375 mg, 516 µl, 3.7 mmol) and the solution was allowed to stir for 30 min. Sodium triacetoxyboron hydride (706 mg, 3.33 mmol) was added step wise and the mixture was allowed to stir for 16 h at room temperature. The solution was added to ice/2N sodium carbonate solution (50 ml), extracted with dichloromethane (2×30 ml). The combined organic layers were dried (MgSO$_4$) and evaporated. The crude material (0.95 g) was purified by flash chromatography on silica gel (20% to 100% dichloromethane/dichloromethane-MeOH 9:1) to yield trans-tert-butyl-(4-{2-[4-(2,3-dihydrofuro[3,2-c]pyridin-4-yl)-piperazin-1-yl]-ethyl}-cyclohexylcarbamate as a white solid (0.49 g, 61.5%), MS (ISP) m/z=431.5 [(M+H)$^+$], mp 89.5° C.

Step C

To a mixture of trans-tert-butyl-(4-{2-[4-(2,3-dihydrofuro[3,2-c]pyridin-4-yl)-piperazin-1-yl]-ethyl}-cyclohexylcarbamate (0.49 g, 1.14 mmol) in dichloromethane (8 ml) was added at room temperature hydrochloric acid solution (4M in dioxane, 4.27 ml, 17.1 mmol) and the mixture was allowed to stir for 3 h, the solvent was evaporated, diethyl ether (20 ml) was added and the mixture was allowed to stir for 30 min at room temperature. The precipitate was collected by filtration, washed with diethyl ether and dried to yield the title compound as a white solid (0.5 g, 100%), MS (ISP) m/z=331.3 [(M+H)⁺], mp 287.5° C.

Intermediate D trans-4-{2-[4-(6-Methyl-furo[3,2-c]pyridin-4-yl)-piperazin-1-yl]-ethyl}-cyclohexylamine trihydrochloride

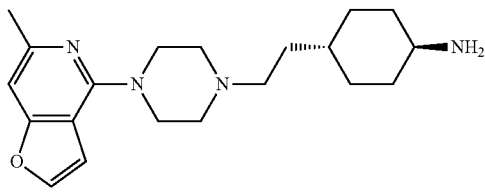 [SMILES: Cc1cc2occc2c(N2CCN(CC[C@H]3CC[C@H](N)CC3)CC2)n1]

The title compound, light yellow solid (1.39 g, 89%), MS (ISP) m/z=343.4 [(M+H)⁺], mp 323.5° C., was prepared in accordance with the general method of intermediate C, steps B and C, from 6-methyl-4-(piperazin-1-yl)-furo[3,2-c]pyridine [CAS-No. 81078-82-2] (0.75 g, 3.45 mmol) and commercially available trans-tert-butyl-4-(2-oxoethyl)-cyclohexyl-carbamate (1.0 g, 4.14 mmol).

Intermediate E trans-4-{2-[4-(6-Methyl-2,3-dihydro-furo[3,2-c]pyridin-4-yl)-piperazin-1-yl]-ethyl}-cyclohexylamine trihydrochloride

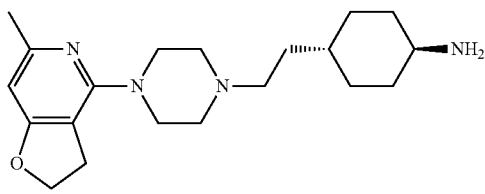 [SMILES: Cc1cc2c(c(N3CCN(CC[C@H]4CC[C@H](N)CC4)CC3)n1)CCO2]

Step A

Hydrogenation of 6-methyl-4-(piperazin-1-yl)-furo[3,2-c]pyridine [CAS-No. 81078-82-2] (0.86 g, 3.96 mmol) on 10% palladium on carbon (170 mg, 1.6 mmol) according to general method of intermediate C, step A yielded 6-methyl-4-(piperazin-1-yl)-2,3-dihydro-furo[3,2-c]pyridine as white solid (0.86 g, 99%), MS (ISP) m/z=220.3 [(M+H)⁺], mp 98° C.

Step B

The title compound, white solid (1.35 g, 76%), MS (ISP) m/z=345.2 [(M+H)⁺], mp 293° C., was prepared in accordance with the general method of intermediate C, steps B and C, from 6-methyl-4-(piperazin-1-yl)-2,3-dihydro-furo[3,2-c]pyridine (step A) (0.86 g, 3.92 mmol) and commercially available trans-tert-butyl-4-(2-oxoethyl)-cyclohexyl-carbamate (1.14 g, 4.71 mmol).

Intermediate F trans-4-{2-[4-(7-Methyl-furo[3,2-c]pyridin-4-yl)-piperazin-1-yl]-ethyl}-cyclohexylamine trihydrochloride

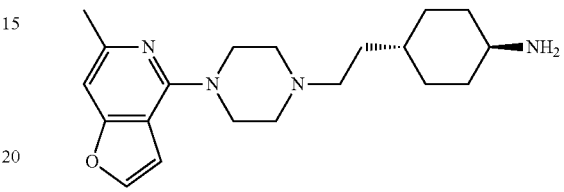

Step A

A stirred mixture of commercially available 4-chloro-7-methyl-furo[3,2-c]pyridine (2.5 g, 14.9 mmol), tert-butyl piperazine-1-carboxylate (3.33 g, 17.9 mmol), sodium tert.-butoxide (2.01 g, 20.9 mmol), palladium(II) acetate (335 mg, 1.49 mmol) and 2-(di-tert.-butylphosphino) biphenyl (445 mg, 1.49 mmol) in toluene (33.0 ml) was heated for 16 h at 100° C. The mixture was cooled and water (10 ml) was added. The mixture was extracted with ethylacetate (2×20 ml). The combined organic layers were washed with brine (20 ml), dried (MgSO4) and evaporated. The crude product (5.9 g) was further purified by flash chromatography on silica gel (10% to 100% ethyl acetate in heptane) to yield tert-butyl 4-(7-methyl-furo[3,2-c]pyridin-4-yl)-piperazine-1-carboxylate as a yellow solid (2.35 g, 50%), MS (ISP) m/z=318.3 [(M+H)⁺], mp 108.5° C.

Step B

A stirred solution of tert-butyl 4-(7-methyl-furo[3,2-c]pyridin-4-yl)-piperazine-1-carboxylate (step A) (2.34 g, 7.37 mmol) in dichloromethane (4.1 ml) was cooled to 0° C., trifluoroacetic acid (8.41 g, 5.68 ml, 73.7 mmol) was added drop wise and the reaction mixture was allowed to stir for 10 min at 0° C. and for 30 min at room temperature. The solution was poured onto ice and 2N sodium carbonate solution (50 ml) and extracted with dichloromethane (2×25 ml). The combined organic layers were washed with brine (30 mL), dried (MgSO4) and evaporated. The crude product (1.59 g) was further purified by flash chromatography on silica gel (100% dichloromethane/MeOH/NH4OH 80:10:1) to yield 7-methyl-4-(piperazin-1-yl)-furo[3,2-c]pyridine as a yellow solid (1.27 g, 79%), MS (ISP) m/z=218.4 [(M+H)⁺], mp 111.5° C.

Step C

The title compound, light yellow solid (1.12 g, 91%), MS (ISP) m/z=343.4 [(M+H)⁺], mp 314.5° C., was prepared in accordance with the general method of intermediate C, steps B and C, from 7-methyl-4-(piperazin-1-yl)-furo[3,2-c]pyridine (step B) (0.59 g, 2.72 mmol) and commercially available trans-tert-butyl-4-(2-oxoethyl)-cyclohexyl-carbamate (925 mg, 3.26 mmol).

Intermediate G trans-4-{2-[4-(7-Methyl-2,3-dihydro-furo[3,2-c]pyridin-4-yl)-piperazin-1-yl]-ethyl}-cyclohexylamine trihydrochloride

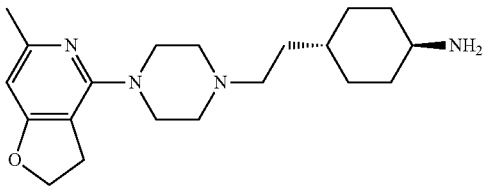 [SMILES: Cc1cc2c(c(N3CCN(CC[C@H]4CC[C@H](N)CC4)CC3)n1)CCO2]

Step A

Hydrogenation of 7-methyl-4-(piperazin-1-yl)-furo[3,2-c]pyridine (intermediate F, step B) (0.68 g, 3.13 mmol) on 10% palladium on carbon (136 mg, 1.28 mmol) according to general method of intermediate C, step A yielded 7-methyl-4-(piperazin-1-yl)-2,3-dihydro-furo[3,2-c]pyridine as white solid (0.64 g, 93%), MS (ISP) m/z=220.3 [(M+H)$^+$], mp 114° C.

Step B

The title compound, white solid (0.55 g, 42%), MS (ISP) m/z=345.3 [(M+H)$^+$], mp 293° C., was prepared in accordance with the general method of intermediate C, steps B and C, from 7-methyl-4-(piperazin-1-yl)-2,3-dihydro-furo[3,2-c]pyridine (step A) (0.64 g, 2.92 mmol) and commercially available trans-tert-butyl-4-(2-oxoethyl)-cyclohexyl-carbamate (0.85 g, 3.52 mmol).

EXAMPLES

Example 1

N-{trans-4-[2-(4-Furo[3,2-c]pyridin-4-yl-piperazin-1-yl)-ethyl]-cyclohexyl}-acetamide

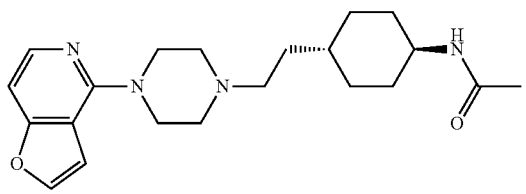

To a solution under N$_2$ of commercially available 4-piperazine-1-yl-furo[3,2-c]pyridine [CAS-Nr. 81078-84-4] (125 mg, 0.62 mmol) in 1,2-dichloroethane (1.25 ml) were added trans-N-[4-(2-oxo-ethyl)-cyclohexyl]-acetamide [CAS-Nr. 946599-01-5, WO 2007/093540] (124 mg, 0.68 mmol) and 3 drops of MeOH. The resulting yellow solution was stirred 18 h at room temperature before addition of Na(AcO)$_3$BH (196 mg, 0.92 mmol). After stirring 18 h at room temperature the reaction mixture was partitioned between sat. aq. NaHCO$_3$ sol. (50 ml) and EtOAc (50 ml). The aqueous layer was extracted with more EtOAc (2×25 ml). The combined organic layers were washed with H$_2$O (40 ml) and brine (40 ml) and dried over MgSO$_4$. After evaporation of the solvent, the crude product (yellow crystals) was purified by flash chromatography on silica gel (CH$_2$Cl$_2$/MeOH, 100:0 to 95:5) to yield the title compound as light yellow crystals (95 mg, 42%), MS (ISP) m/z=371.2 [(M+H)$^+$].

Example 2

N-{trans-4-[2-(4-Furo[3,2-c]pyridin-4-yl-piperazin-1-yl)-ethyl]-cyclohexyl}-2-(trans-3-methoxy-cyclopentyl)-acetamide

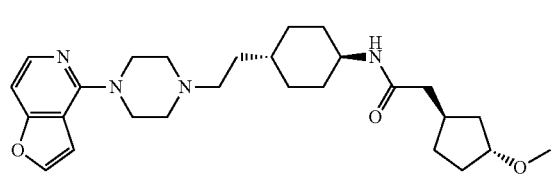 [SMILES: CO[C@@H]1CC[C@@H](CC(=O)N[C@H]2CC[C@H](CCN3CCN(c4nccc5occc45)CC3)CC2)C1]

A mixture of racemic trans-(3-methoxy-cyclopentyl)-acetic acid methyl ester [WO 2009/019174] (70 mg, 0.41 mmol) and KOSiMe$_3$ (88 mg, 0.69 mmol) in CH$_2$Cl$_2$ (1.5 ml) was stirred at room temperature over night. The solvent was evaporated and DMF (1.5 ml) was added followed by trans-4-[2-(4-furo[3,2-c]pyridin-4-yl-piperazin-1-yl)-ethyl]-cyclohexylamine trihydrochloride (intermediate A) (150 mg, 0.34 mmol), DIPEA (177 mg, 1.37 mmol) and TBTU (143 mg, 0.44 mmol). After stirring 4 h at room temperature, sat. aq. NaHCO$_3$ sol. was added and the product was extracted with CH$_2$Cl$_2$. The organic layer was dried (Na$_2$SO$_4$), the solvent was evaporated and the crude product was purified by flash chromatography on silica gel (CH$_2$Cl$_2$/MeOH/25% NH$_3$ $_{aq}$ 140:10:1) to yield the title compound as a white solid (125 mg, 78%), MS (ISP) m/z=469.3 [(M+H)$^+$].

Example 3

N-{trans-4-[2-(4-Furo[3,2-c]pyridin-4-yl-piperazin-1-yl)-ethyl]-cyclohexyl}-2-(trans-4-hydroxy-cyclohexyl)-acetamide

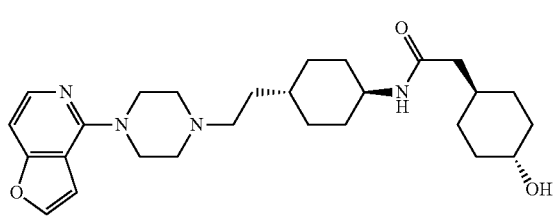

The title compound, white solid (159 mg, quant.), MS (ISP) m/z=469.3 [(M+H)$^+$], was prepared in analogy to example 2 from trans-4-[2-(4-furo[3,2-c]pyridin-4-yl-piperazin-1-yl)-ethyl]-cyclohexylamine trihydrochloride (intermediate A) (150 mg, 0.34 mmol) and trans-(4-hydroxy-cyclohexyl)-acetic acid methyl ester [CAS-Nr. 1124174-16-8, WO 2010/031735] (71 mg, 0.41 mmol). The purification was performed by precipitation from Et$_2$O.

Example 4

N-{trans-4-[2-(4-Furo[3,2-c]pyridin-4-yl-piperazin-1-yl)-ethyl]-cyclohexyl}-propionamide

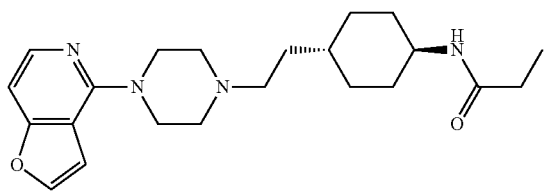 [SMILES: CCC(=O)N[C@H]1CC[C@H](CCN2CCN(c3nccc4occc34)CC2)CC1]

To a solution in DMF (1.5 ml) of trans-4-[2-(4-furo[3,2-c]pyridin-4-yl-piperazin-1-yl)-ethyl]-cyclohexylamine trihydrochloride (intermediate A) (150 mg, 0.34 mmol) were added propionic acid (27 mg, 0.36 mmol), DIPEA (177 mg, 1.37 mmol) and TBTU (115 mg, 0.36 mmol). The reaction mixture was stirred over night at room temperature then sat. aq. NaHCO$_3$ sol. was added and the product was extracted with EtOAc. After drying (Na$_2$SO$_4$) the solvent was evaporated and the product was purified by flash chromatography on silica gel (CH$_2$Cl$_2$/MeOH/25% NH$_{3\ aq}$ 140:10:1) to yield the title compound as a white solid (123 mg, 93%), MS (ISP) m/z=385.3 [(M+H)$^+$].

Example 5

N-{trans-4-[2-(4-Furo[3,2-c]pyridin-4-yl-piperazin-1-yl)-ethyl]-cyclohexyl}-3-methoxy-propionamide

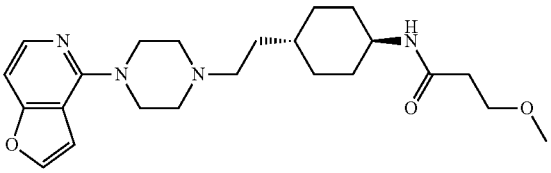

The title compound, white solid (122 mg, 86%), MS (ISP) m/z=415.3 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and 3-methoxy-propionic acid (37 mg, 0.36 mmol).

Example 6

N-{trans-4-[2-(4-Furo[3,2-c]pyridin-4-yl-piperazin-1-yl)-ethyl]-cyclohexyl}-3-hydroxy-propionamide

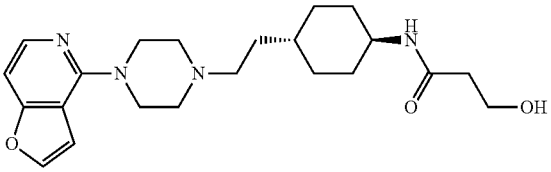 [SMILES: O=C(CCO)N[C@H]1CC[C@H](CCN2CCN(c3nccc4occc34)CC2)CC1]

The title compound, white solid (10 mg, 7%), MS (ISP) m/z=401.4 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and 3-hydroxy-propionic acid (32 mg, 0.36 mmol).

Example 7

N-{trans-4-[2-(4-Furo[3,2-c]pyridin-4-yl-piperazin-1-yl)-ethyl]-cyclohexyl}-2-hydroxy-acetamide

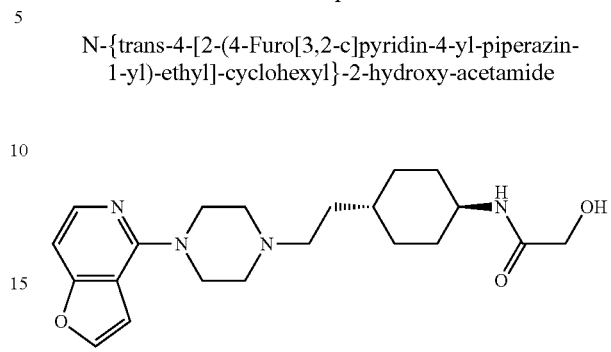

The title compound, white solid (98 mg, 75%), MS (ISP) m/z=387.2 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and hydroxy-acetic acid (27 mg, 0.36 mmol).

Example 8

N-{trans-4-[2-(4-Furo[3,2-c]pyridin-4-yl-piperazin-1-yl)-ethyl]-cyclohexyl}-2-methoxy-acetamide

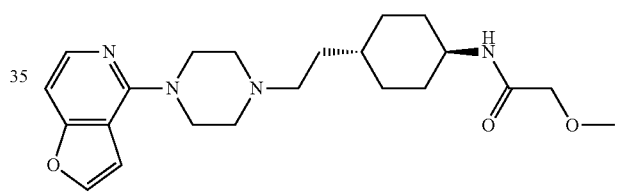

The title compound, white solid (120 mg, 87%), MS (ISP) m/z=401.3 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and methoxy-acetic acid (32 mg, 0.36 mmol).

Example 9

N-{trans-4-[2-(4-Furo[3,2-c]pyridin-4-yl-piperazin-1-yl)-ethyl]-cyclohexyl}-2-(trans-4-methoxy-cyclohexyl)-acetamide

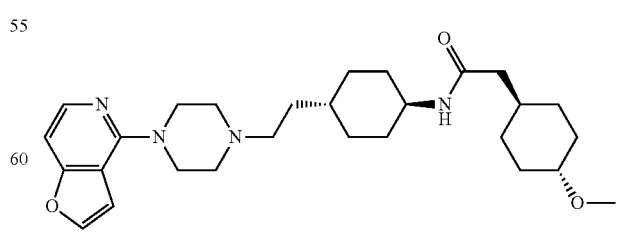

The title compound, white solid (138 mg, 83%), MS (ISP) m/z=483.3 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and (trans-4-methoxy-cyclohexyl)-acetic acid [CAS-Nr. 879877-61-9, US 2010/075985] (62 mg, 0.36 mmol).

Example 10

N-{trans-4-[2-(4-Furo[3,2-c]pyridin-4-yl-piperazin-1-yl)-ethyl]-cyclohexyl}-2-(tetrahydro-pyran-4-yl)-acetamide

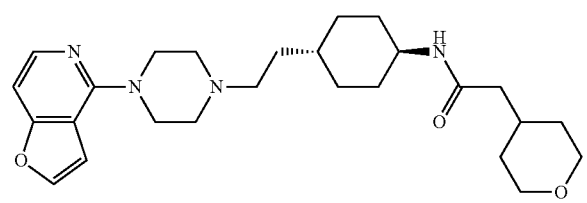

The title compound, white solid (116 mg, 75%), MS (ISP) m/z=455.3 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and (tetrahydro-pyran-4-yl)-acetic acid (52 mg, 0.36 mmol).

Example 11

Tetrahydro-pyran-4-carboxylic acid {trans-4-[2-(4-furo[3,2-c]pyridin-4-yl-piperazin-1-yl)-ethyl]-cyclohexyl}-amide

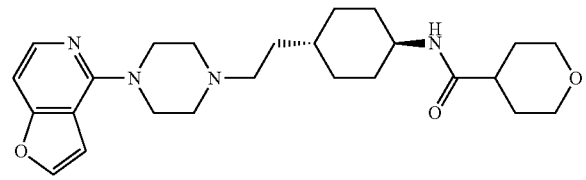

The title compound, white solid (123 mg, 82%), MS (ISP) m/z=441.4 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and tetrahydro-pyran-4-carboxylic acid (47 mg, 0.36 mmol).

Example 12

2-Ethoxy-N-{trans-4-[2-(4-furo[3,2-c]pyridin-4-yl-piperazin-1-yl)-ethyl]-cyclohexyl}-acetamide

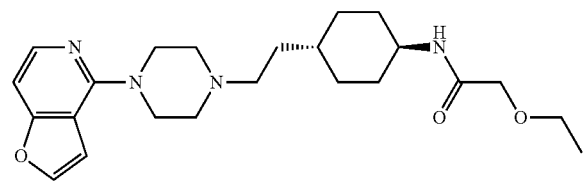 [SMILES: CCOCC(=O)N[C@H]1CC[C@H](CCN2CCN(c3nccc4occc34)CC2)CC1]

The title compound, white crystals (86 mg, 60%), MS (ISP) m/z=415.3 [(M+H)$^+$], was prepared in analogy to example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and ethoxyacetic acid (43 mg, 0.41 mmol).

Example 13

Cyclopropanecarboxylic acid {trans-4-[2-(4-furo[3,2-c]pyridin-4-yl-piperazin-1-yl)-ethyl]-cyclohexyl}-amide

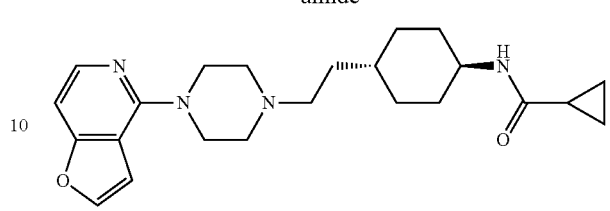

The title compound, white crystals (118 mg, 87%), MS (ISP) m/z=397.2 [(M+H)$^+$], was prepared in analogy to example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and cyclopropanecarboxylic acid (41 mg, 0.47 mmol).

Example 14

N-{trans-4-[2-(4-Furo[3,2-c]pyridin-4-yl-piperazin-1-yl)-ethyl}-cyclohexyl]-methanesulfonamide

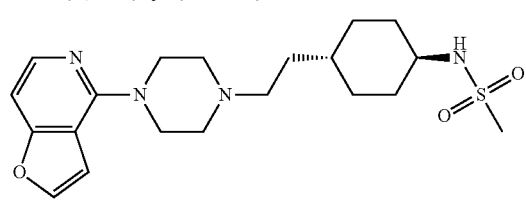

trans-4-[2-(4-Furo[3,2-c]pyridin-4-yl-piperazin-1-yl)-ethyl]-cyclohexylamine trihydrochloride (intermediate A) (150 mg, 0.34 mmol) was dissolved in CH$_2$Cl$_2$ (1.5 ml) and the solution was cooled to 0° C. Et$_3$N (139 mg, 1.37 mmol) and methanesulfonyl chloride (78 mg, 0.68 mmol) were added and the reaction mixture was stirred over night at room temperature. H$_2$O was added and the product was extracted with CH$_2$Cl$_2$. The organic layer was dried (Na$_2$SO$_4$) and the solvent was evaporated. Purification by flash chromatography over silica gel (CH$_2$Cl$_2$/MeOH/25% NH$_{3\ aq}$ 140:10:1) yielded the title compound as a white solid (78 mg, 56%), MS (ISP) m/z=407.2 [(M+H)$^+$].

Example 15

N-{trans-4-[2-(4-Thieno[3,2-c]pyridin-4-yl-piperazin-1-yl)-ethyl]-cyclohexyl}-acetamide

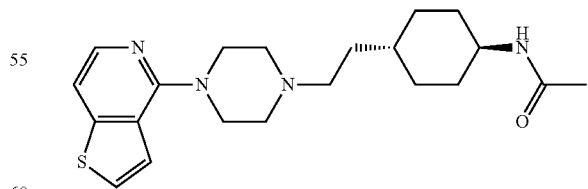

The title compound, light brown solid (114 mg, 43%), MS (ISP) m/z=387.1 [(M+H)$^+$], was prepared in analogy to example 1 from commercially available 4-piperazine-1-yl-thieno[3,2-c]pyridine [CAS-Nr. 106261-27-2] (150 mg, 0.68 mmol) and trans-N-[4-(2-oxo-ethyl)-cyclohexyl]-acetamide [CAS-Nr. 946599-01-5, WO 2007/093540] (125 mg, 0.68 mmol). Purification was performed by flash chromatography over silica gel (CH$_2$Cl$_2$/MeOH/25% NH$_{3\ aq}$ 140:10:1).

Example 16

Ethanesulfonic acid {trans-4-[2-(4-furo[3,2-c]pyridin-4-yl-piperazin-1-yl)-ethyl]-cyclohexyl}-amide

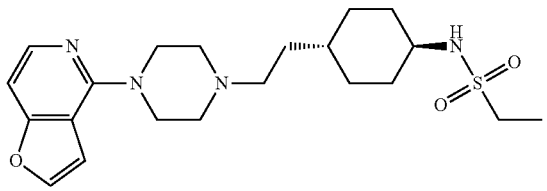

The title compound, light brown foam (77 mg, 54%), MS (ISP) m/z=421.2 [(M+H)$^+$], was prepared in analogy to example 14 starting from trans-4-[2-(4-furo[3,2-c]pyridin-4-yl-piperazin-1-yl)-ethyl]-cyclohexylamine trihydrochloride (intermediate A) (150 mg, 0.34 mmol) and ethanesulfonyl chloride (88 mg, 0.68 mmol).

Example 17

N'-(trans-4{[4-(furo[3,2-c]pyridin-4-yl)-piperazin-1-yl]-ethyl}cyclohexyl)-N,N-dimethylsulfamide

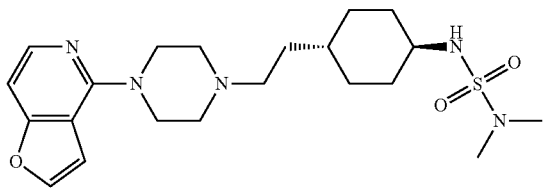 [SMILES: CCS(=O)(=O)N[C@H]1CC[C@H](CCN2CCN(c3nccc4occc34)CC2)CC1]

trans-4-[2-(4-Furo[3,2-c]pyridin-4-yl-piperazin-1-yl)-ethyl]-cyclohexylamine trihydrochloride (intermediate A) (150 mg, 0.34 mmol) was dissolved in CH$_2$Cl$_2$ (1.5 ml) and the solution was cooled to 0° C. Et$_3$N (139 mg, 1.37 mmol) and dimethylsulfamoylchloride (98 mg, 0.68 mmol) were added and the reaction mixture was stirred over night at room temperature. H$_2$O was added and the product was extracted with CH$_2$Cl$_2$. The organic layer was dried (Na$_2$SO$_4$) and the solvent was evaporated. Purification by flash chromatography over silica gel (CH$_2$Cl$_2$/MeOH/25% NH$_{3\ aq}$ 140:10:1) yielded the title compound as a white solid (89 mg, 60%), MS (ISP) m/z=436.3 [(M+H)$^+$].

Example 18

N-{trans-4-[2-(4-Thieno[3,2-c]pyridin-4-yl-piperazin-1-yl)-ethyl]-cyclohexyl}-propionamide

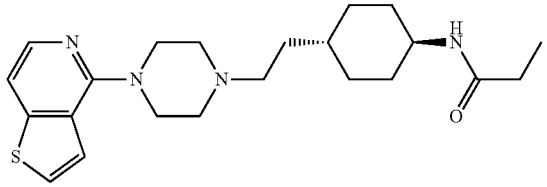 [SMILES: CCC(=O)N[C@H]1CC[C@H](CCN2CCN(c3nccc4sccc34)CC2)CC1]

The title compound was prepared in analogy to example 4 starting from trans-4-[2-(4-thieno[3,2-c]pyridin-4-yl-piperazin-1-yl)-ethyl]-cyclohexylamine trihydrochloride (intermediate B) (100 mg, 0.22 mmol) and propionic acid (17 mg, 0.23 mmol). Purification by flash chromatography on silica gel (CH2Cl2/MeOH 95:5). White crystals (31 mg, 35%), MS (ISP) m/z=401.3 [(M+H)$^+$].

Example 19

3-Methoxy-N-{trans-4-[2-(4-thieno[3,2-c]pyridin-4-yl-piperazin-1-yl)-ethyl]-cyclohexyl}-propionamide

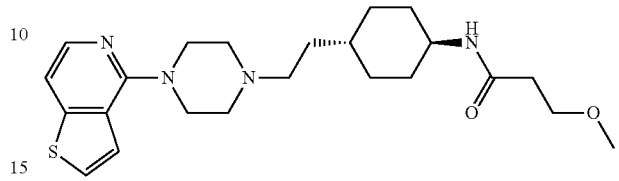

The title compound was prepared in analogy to example 4 starting from trans-4-[2-(4-thieno[3,2-c]pyridin-4-yl-piperazin-1-yl)-ethyl]-cyclohexylamine trihydrochloride (intermediate B) (100 mg, 0.22 mmol) and 3-methoxypropionic acid (24 mg, 0.23 mmol). Purification by flash chromatography on silica gel (CH2Cl2/MeOH 95:5). White crystals (61 mg, 64%), MS (ISP) m/z=431.3 [(M+H)$^+$].

Example 20

2-(trans-4-Methoxy-cyclohexyl)-N-{trans-4-[2-(4-thieno[3,2-c]pyridin-4-yl-piperazin-1-yl)-ethyl]-cyclohexyl}-acetamide

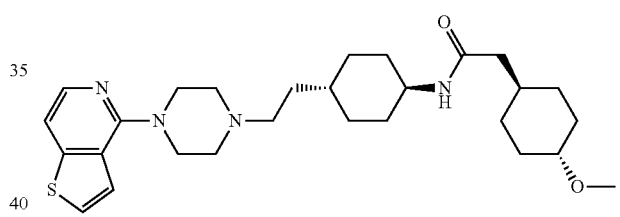

The title compound was prepared in analogy to example 4 starting from trans-4-[2-(4-thieno[3,2-c]pyridin-4-yl-piperazin-1-yl)-ethyl]-cyclohexylamine trihydrochloride (intermediate B) (100 mg, 0.22 mmol) and (trans-4-methoxy-cyclohexyl)-acetic acid [CAS-Nr. 879877-61-9, US 2010/075985] (40 mg, 0.23 mmol). Purification by flash chromatography on silica gel (CH$_2$Cl$_2$/MeOH 95:5). White crystals (68 mg, 62%), MS (ISP) m/z=499.3 [(M+H)$^+$].

Example 21

2-(trans-3-Methoxy-cyclopentyl)-N-{trans-4-[2-(4-thieno[3,2-c]pyridin-4-yl-piperazin-1-yl)-ethyl]-cyclohexyl}-acetamide

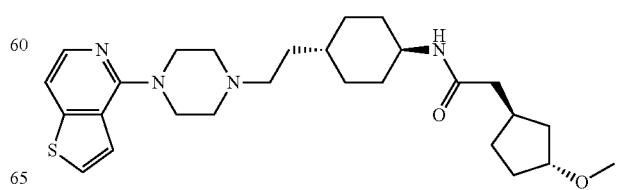

The title compound was prepared in analogy to example 2 starting from trans-4-[2-(4-thieno[3,2-c]pyridin-4-yl-piperazin-1-yl)-ethyl]-cyclohexylamine trihydrochloride (intermediate B) (100 mg, 0.22 mmol) and racemic trans-(3-methoxy-cyclopentyl)-acetic acid methyl ester [WO 2009/019174] (46 mg, 0.27 mmol). Purification by flash chromatography on silica gel (CH$_2$Cl$_2$/MeOH 95:5). White crystals (61 mg, 57%), MS (ISP) m/z=485.4 [(M+H)$^+$].

Example 22

2-Methoxy-N-{trans-4-[2-(4-thieno[3,2-c]pyridin-4-yl-piperazin-1-yl)-ethyl]-cyclohexyl}-acetamide

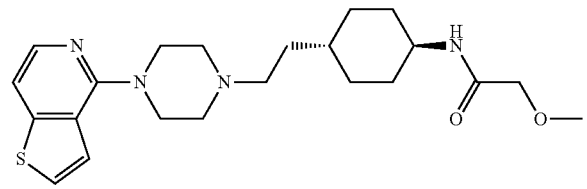

The title compound was prepared in analogy to example 4 starting from trans-4-[2-(4-thieno[3,2-c]pyridin-4-yl-piperazin-1-yl)-ethyl]-cyclohexylamine trihydrochloride (intermediate B) (150 mg, 0.33 mmol) and methoxyacetic acid (31 mg, 0.34 mmol). Purification by flash chromatography on silica gel (CH$_2$Cl$_2$/MeOH 95:5). White solid (66 mg, 48%), MS (ISP) m/z=417.1 [(M+H)$^+$].

Example 23

2-(Tetrahydro-pyran-4-yl)-N-{trans-4-[2-(4-thieno[3,2-c]pyridin-4-yl-piperazin-1-yl)-ethyl]-cyclohexyl}-acetamide

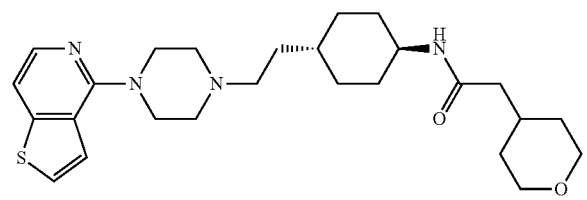 [SMILES: O=C(CC1CCOCC1)N[C@H]1CC[C@H](CCN2CCN(c3nccc4sccc34)CC2)CC1]

The title compound was prepared in analogy to example 4 starting from trans-4-[2-(4-thieno[3,2-c]pyridin-4-yl-piperazin-1-yl)-ethyl]-cyclohexylamine trihydrochloride (intermediate B) (150 mg, 0.33 mmol) and tetrahydropyran-4-yl-acetic acid (50 mg, 0.35 mmol). Purification by flash chromatography on silica gel (CH$_2$Cl$_2$/MeOH 95:5). Off-white crystals (108 mg, 69%), MS (ISP) m/z=471.2 [(M+H)$^+$].

Example 24

Tetrahydro-pyran-4-carboxylic acid {trans-4-[2-(4-thieno[3,2-c]pyridin-4-yl-piperazin-1-yl)-ethyl]-cyclohexyl}-amide

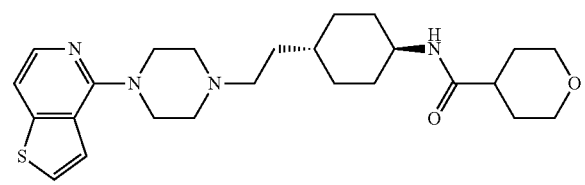 [SMILES: O=C(N[C@H]1CC[C@H](CCN2CCN(c3nccc4sccc34)CC2)CC1)C1CCOCC1]

The title compound was prepared in analogy to example 4 starting from trans-4-[2-(4-thieno[3,2-c]pyridin-4-yl-piperazin-1-yl)-ethyl]-cyclohexylamine trihydrochloride (intermediate B) (150 mg, 0.33 mmol) and tetrahydropyran-4-ylcarboxylic acid (45 mg, 0.34 mmol). Purification by flash chromatography on silica gel (CH$_2$Cl$_2$/MeOH 95:5). White crystals (51 mg, 34%), MS (ISP) m/z=457.3 [(M+H)$^+$].

Example 25

2-((1R,3R)-3-Methoxy-cyclopentyl)-N-{trans-4-[2-(4-thieno[3,2-c]pyridin-4-yl-piperazin-1-yl)-ethyl]-cyclohexyl}-acetamide

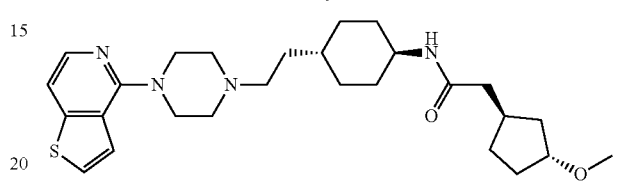

and

Example 26

2-((1S,3S)-3-Methoxy-cyclopentyl)-N-{trans-4-[2-(4-thieno[3,2-c]pyridin-4-yl-piperazin-1-yl)-ethyl]-cyclohexyl}-acetamide

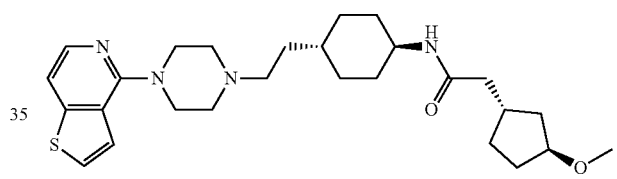

Racemic 2-(trans-3-methoxy-cyclopentyl)-N-{trans-4-[2-(4-thieno[3,2-c]pyridin-4-yl-piperazin-1-yl)-ethyl]-cyclohexyl}-acetamide (example 21) (50 mg, 0.10 mmol) was separated by HPLC into its enantiomers. Chiralpak AD (5×50 cm) column, 20% iPrOH in heptane. (+)-Enantiomer (18 mg, 36%) Rt=94 min, MS (ISP) m/z=485.4 [(M+H)$^+$]. (−)-Enantiomer (17 mg, 34%) Rt=115 min, MS (ISP) m/z=485.4 [(M+H)$^+$].

Example 27

2-Hydroxy-N-{trans-4-[2-(4-thieno[3,2-c]pyridin-4-yl-piperazin-1-yl)-ethyl]-cyclohexyl}-acetamide

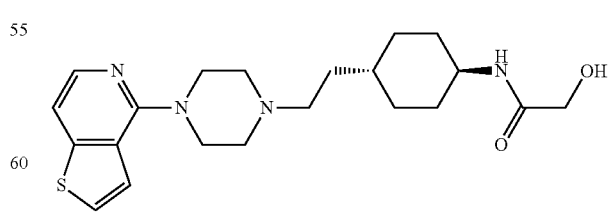

The title compound was prepared in analogy to example 4 starting from trans-4-[2-(4-thieno[3,2-c]pyridin-4-yl-piperazin-1-yl)-ethyl]-cyclohexylamine trihydrochloride (intermediate B) (150 mg, 0.33 mmol) and glycolic acid (26 mg, 0.34 mmol). Purification by flash chromatography on silica gel (CH$_2$Cl$_2$/MeOH 95:5). White solid (67 mg, 50%), MS (ISP) m/z=403.3 [(M+H)$^+$].

Example 28

2-(trans-4-Hydroxy-cyclohexyl)-N-{trans-4-[2-(4-thieno[3,2-c]pyridin-4-yl-piperazin-1-yl)-ethyl]-cyclohexyl}-acetamide

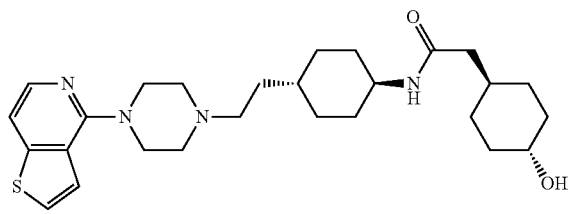 [SMILES: O=C(C[C@H]1CC[C@H](O)CC1)N[C@H]1CC[C@H](CCN2CCN(c3nccc4sccc34)CC2)CC1]

The title compound was prepared in analogy to example 2 starting from trans-4-[2-(4-thieno[3,2-c]pyridin-4-yl-piperazin-1-yl)-ethyl]-cyclohexylamine trihydrochloride (intermediate B) (1150 mg, 0.33 mmol) and trans-(4-hydroxy-cyclohexyl)-acetic acid methyl ester [CAS-Nr. 1124174-16-8, WO 2010/031735] (68 mg, 0.39 mmol). Purification by flash chromatography on silica gel (CH2Cl2/MeOH 95:5). White crystals (83 mg, 52%), MS (ISP) m/z=485.4 [(M+H)$^+$].

Example 29

Quinoline-4-carboxylic acid {trans-4-[2-(4-furo[3,2-c]pyridin-4-yl-piperazin-1-yl)-ethyl]-cyclohexyl}-amide

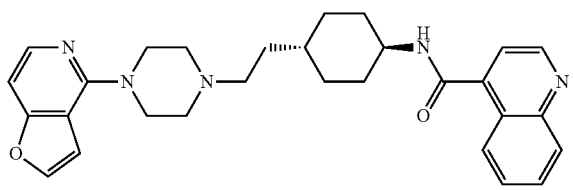

The title compound, white crystals (70 mg, 42%), MS (ISP) m/z=484.4 [(M+H)$^+$], was prepared following the method of example 4 starting from trans-4-[2-(4-furo[3,2-c]pyridin-4-yl-piperazin-1-yl)-ethyl]-cyclohexylamine trihydrochloride (intermediate A) (150 mg, 0.34 mmol) and quinoline-4-carboxylic acid (71 mg, 0.41 mmol). Purification by flash chromatography on silica gel (CH$_2$Cl$_2$/MeOH 95:5).

Example 30

N-{trans-4-[2-(4-Thieno[3,2-c]pyridin-4-yl-piperazin-1-yl)-ethyl]-cyclohexyl}-methanesulfonamide

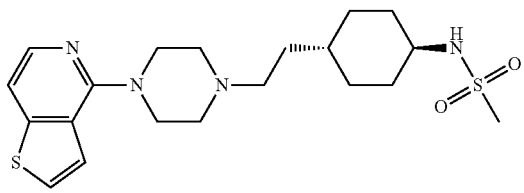

The title compound, off white solid (26 mg, 18%), MS (ISP) m/z=423.1 [(M+H)$^+$], was prepared following the procedure for example 14 starting from trans-4-[2-(4-thieno[3,2-c]pyridin-4-yl-piperazin-1-yl)-ethyl]-cyclohexylamine trihydrochloride (intermediate B (150 mg, 0.34 mmol) and methanesulfonyl chloride (77 mg, 0.68 mmol).

Example 31

Ethanesulfonic acid {trans-4-[2-(4-thieno[3,2-c]pyridin-4-yl-piperazin-1-yl)-ethyl]-cyclohexyl}-amide

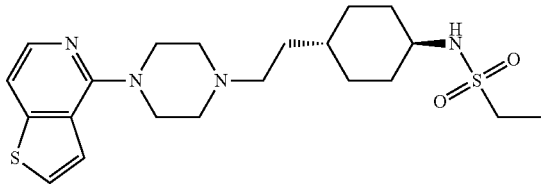

The title compound, off white solid (41 mg, 28%), MS (ISP) m/z=437.2 [(M+H)$^+$], was prepared following the procedure for example 14 starting from trans-4-[2-(4-thieno[3,2-c]pyridin-4-yl-piperazin-1-yl)-ethyl]-cyclohexylamine trihydrochloride (intermediate B (150 mg, 0.34 mmol) and ethanesulfonyl chloride (87 mg, 0.68 mmol).

Example 32 trans-N-(4-{2-[4-(2,3-Dihydro-furo[3,2-c]pyridin-4-yl)-piperazin-1-yl]-ethyl}-cyclo hexyl)-acetamide

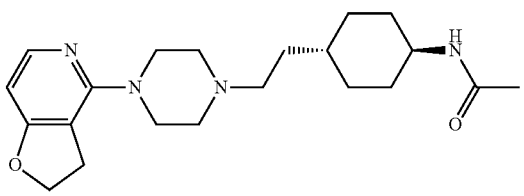 [SMILES: CC(=O)N[C@H]1CC[C@H](CCN2CCN(c3nccc4c3CCO4)CC2)CC1]

To a stirred mixture of trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) in DMF (1.8 ml) was added N,N-diisopropylethylamine (210 mg, 278 µl, 1.63 mmol), acetic acid (18.0 mg, 17.2 µl, 300 µmol) and TBTU (128 mg, 400 µmol). The mixture was allowed to stir at room temperature for 4 h. The mixture was added to ice/water (5 ml) and 1N NaOH (5 ml) and extracted with dichloromethane/MeOH (9:1, 20 ml). The organic phase was washed with brine (20 ml), dried (MgSO$_4$) and evaporated. The crude material (0.15 g) was triturated with dichloromethane (2 ml) and diethyl ether (5 ml) for ½ h, the precipitate was collected by filtration, washed with diethyl ether and dried to yield the title compound as off-white solid (92 mg, 99%), MS (ISP) m/z=373.2 [(M+H)$^+$], mp 260° C.

Example 33 trans-N-(4-{2-[4-(2,3-Dihydrofuro[3,2-c]pyridin-4-yl)-piperazin-1-yl]-ethyl}-cyclohexyl)-tetrahydro-2H-pyran-4-carboxamide

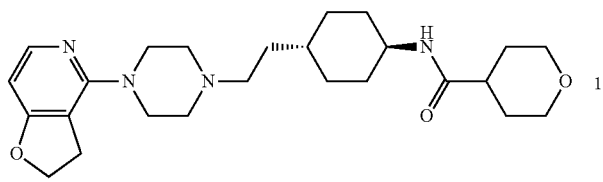

The title compound, off-white solid (101 mg, 91%), MS (ISP) m/z=443.5 [(M+H)⁺], mp 263° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and tetrahydropyran-4-yl-carboxylic acid.

Example 34 trans-N-(4-{2-[4-(2,3-Dihydrofuro[3,2-c]pyridin-4-yl)-piperazin-1-yl]-ethyl}-cyclohexyl)-2-(tetrahydro-2H-pyran-4-yl)-acetamide

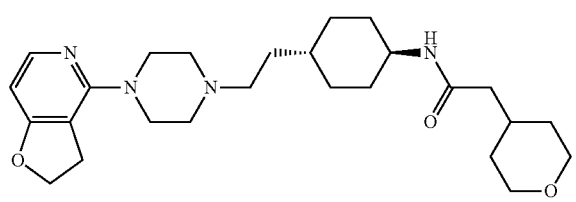

The title compound, off-white solid (105 mg, 92%), MS (ISP) m/z=457.4 [(M+H)⁺], mp 233° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and tetrahydropyran-4-yl-acetic acid.

Example 35 trans-N-(4-{2-[4-(2,3-Dihydrofuro[3,2-c]pyridin-4-yl)-piperazin-1-yl]-ethyl}-cyclohexyl)-3-methoxypropanamide

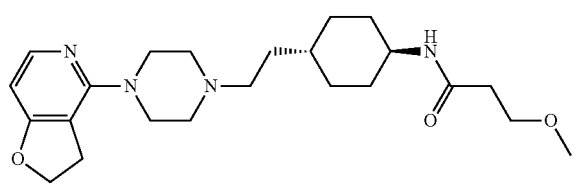

The title compound, off-white solid (65 mg, 62%), MS (ISP) m/z=417.4 [(M+H)⁺], mp 246.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 3-methoxypropionic acid.

Example 36 trans-N-(4-{2-[4-(2,3-Dihydrofuro[3,2-c]pyridin-4-yl)-piperazin-1-yl]-ethyl}-cyclohexyl)-propionamide

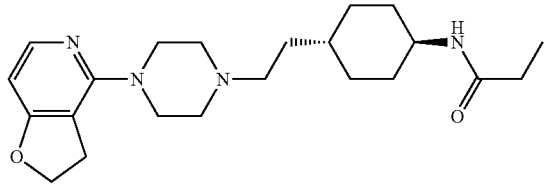

The title compound, white solid (95 mg, 82%), MS (ISP) m/z=387.4 [(M+H)⁺], mp 192.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (132 mg, 0.3 mmol) and propionic acid.

Example 37 trans-N-(4-{2-[4-(2,3-Dihydrofuro[3,2-c]pyridin-4-yl)-piperazin-1-yl]-ethyl}-cyclohexyl)-2-(rac-1,4-dioxan-2-yl)-acetamide

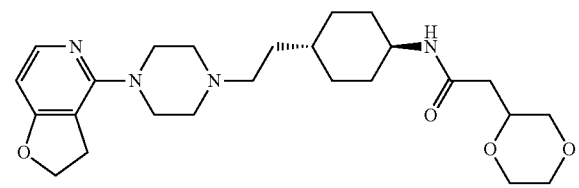

The title compound, white solid (107 mg, 78%), MS (ISP) m/z=459.4 [(M+H)⁺], mp 186° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (132 mg, 0.3 mmol) and rac-(1,4-dioxan-2-yl)-acetic acid.

Example 38 trans-N-(4-{2-[4-(2,3-Dihydrofuro[3,2-c]pyridin-4-yl)-piperazin-1-yl]-ethyl}-cyclohexyl)-2-methoxyacetamide

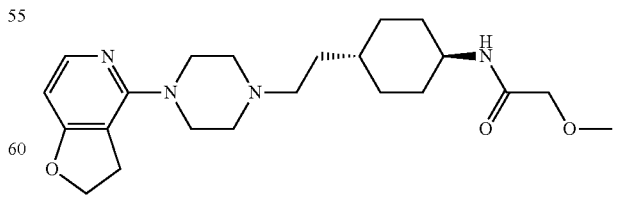

The title compound, white solid (86 mg, 71%), MS (ISP) m/z=403.4 [(M+H)⁺], mp 169.5° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (132 mg, 0.3 mmol) and methoxyacetic acid.

Example 39 trans-N-(4-{2-[4-(2,3-Dihydrofuro[3,2-c]pyridin-4-yl)-piperazin-1-yl]-ethyl}-cyclohexyl)-methylsulfonyl-acetamide

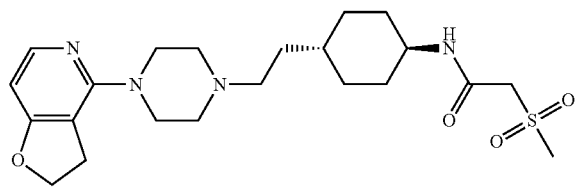 [SMILES: CS(=O)(=O)CC(=O)N[C@H]1CC[C@H](CCN2CCN(c3nccc4c3CCO4)CC2)CC1]

The title compound, off-white solid (106 mg, 78%), MS (ISP) m/z=451.3 [(M+H)$^+$], mp 260.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (132 mg, 0.3 mmol) and 2-methylsulfonyl-acetic acid.

Example 40 trans-N-(4-{2-[4-(2,3-Dihydrofuro[3,2-c]pyridin-4-yl)-piperazin-1-yl]-ethyl}-cyclohexyl)-hydroxyacetamide

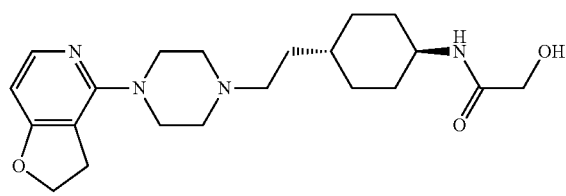 [SMILES: O=C(CO)N[C@H]1CC[C@H](CCN2CCN(c3nccc4c3CCO4)CC2)CC1]

The title compound, white solid (110 mg, 94%), MS (ISP) m/z=389.3 [(M+H)$^+$], mp 237° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (132 mg, 0.3 mmol) and hydroxyacetic acid.

Example 41 trans-N-(4-{2-[4-(2,3-Dihydrofuro[3,2-c]pyridin-4-yl)-piperazin-1-yl]-ethyl}-cyclohexyl)-3-hydroxypropanamide

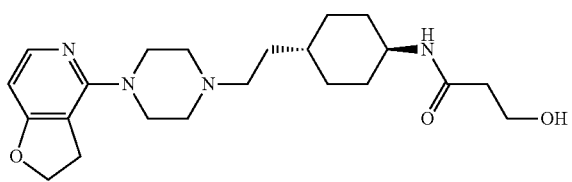

The title compound, white solid (80 mg, 66%), MS (ISP) m/z=403.4 [(M+H)$^+$], mp 173° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (132 mg, 0.3 mmol) and 3-hydroxy-propionic acid

Example 42 trans-N-(4-{2-[4-(2,3-Dihydrofuro[3,2-c]pyridin-4-yl)-piperazin-1-yl]-ethyl}-cyclohexyl)-rac-tetrahydrofuran-3-carboxamide

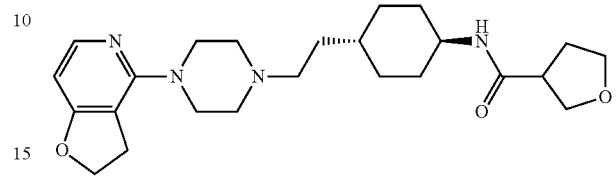

The title compound, white solid (101 mg, 79%), MS (ISP) m/z=429.3 [(M+H)$^+$], mp 208.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (132 mg, 0.3 mmol) and rac-tetrahydrofuran-3-carboxylic acid.

Example 43 trans-N-(4-{2-[4-(2,3-Dihydrofuro[3,2-c]pyridin-4-yl)-piperazin-1-yl]-ethyl}-cyclohexyl)-rac-tetrahydrofuran-2-carboxamide

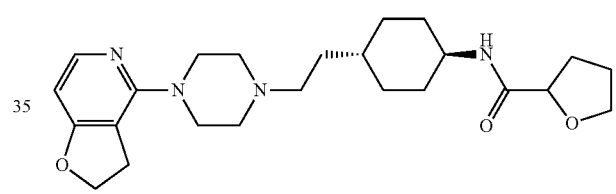

The title compound, white solid (100 mg, 78%), MS (ISP) m/z=429.3 [(M+H)$^+$], mp 176.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (132 mg, 0.3 mmol) and rac-tetrahydrofuran-2-carboxylic acid.

Example 44 trans-N-(4-{2-[4-(2,3-Dihydro-furo[3,2-c]pyridin-4-yl)-piperazin-1-yl]-ethyl}-cyclohexyl)-benzamide

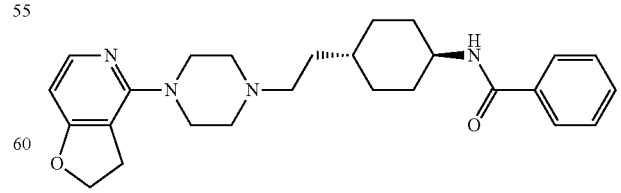

The title compound, white solid (100 mg, 92%), MS (ISP) m/z=435.3 [(M+H)$^+$], mp 207.5° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (110 mg, 0.25 mmol) and benzoic acid.

Example 45 trans-N-(4-{2-[4-(2,3-Dihydro-furo[3,2-c]pyridin-4-yl)-piperazin-1-yl]-ethyl}-cyclohexyl)-4-fluoro-benzamide

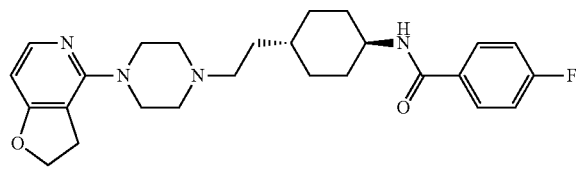 [SMILES: O=C(N[C@H]1CC[C@H](CCN2CCN(c3nccc4c3CCO4)CC2)CC1)c1ccc(F)cc1]

The title compound, white solid (100 mg, 88%), MS (ISP) m/z=453.3 [(M+H)$^+$], mp 209.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-fluorobenzoic acid.

Example 46 trans-4-Chloro-N-(4-{2-[4-(2,3-dihydro-furo[3,2-c]pyridin-4-yl)-piperazin-1-yl]-ethyl}-cyclohexyl)-benzamide

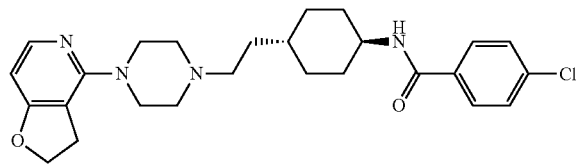 [SMILES: O=C(N[C@H]1CC[C@H](CCN2CCN(c3nccc4c3CCO4)CC2)CC1)c1ccc(Cl)cc1]

The title compound, off-white solid (103 mg, 88%), MS (ISP) m/z=469.3 [(M+H)$^+$], mp 226.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-chlorobenzoic acid.

Example 47 trans-N-(4-{2-[4-(2,3-Dihydro-furo[3,2-c]pyridin-4-yl)-piperazin-1-yl]-ethyl}-cyclohexyl)-4-trifluoromethyl-benzamide

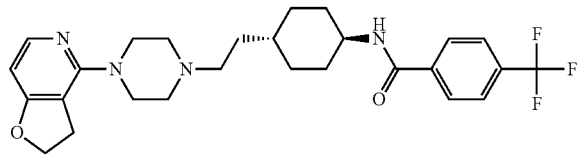 [SMILES: O=C(N[C@H]1CC[C@H](CCN2CCN(c3nccc4c3CCO4)CC2)CC1)c1ccc(C(F)(F)F)cc1]

The title compound, off-white solid (111 mg, 88%), MS (ISP) m/z=503.3 [(M+H)$^+$], mp 227° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-trifluoromethyl-benzoic acid.

Example 48 trans-N-(4-{2-[4-(2,3-Dihydro-furo[3,2-c]pyridin-4-yl)-piperazin-1-yl]-ethyl}-cyclohexyl)-methanesulfonamide

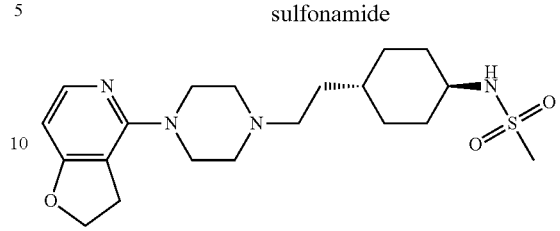

To a stirred mixture of trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) in dichloromethane (1.6 ml) was added at room temperature triethylamine (139 mg, 192 µl, 1.38 mmol) and methanesulfonyl chloride (43.0 mg, 29.2 µl, 375 µmol). The mixture was allowed to stir at room temperature for 4 h, poured into ice/water (5 ml) and 1N sodium hydroxide solution (5 ml) and extracted with dichloromethane (2×20 ml). The combined organic layers were washed with brine (20 ml), dried (MgSO$_4$) and evaporated. The crude material (0.1 g) was triturated with dichloromethane (1 ml) and heptane (5 mL) for 30 min. The precipitate was collected by filtration, washed with heptane and dried to yield the title compound as a white solid (90 mg, 88%), MS (ISP) m/z=409.4 [(M+H)$^+$], mp 220° C.

Example 49

Ethanesulfonic acid trans-(4-{2-[4-(2,3-dihydro-furo[3,2-c]pyridin-4-yl)-piperazin-1-yl]-ethyl}-cyclohexyl)-amide

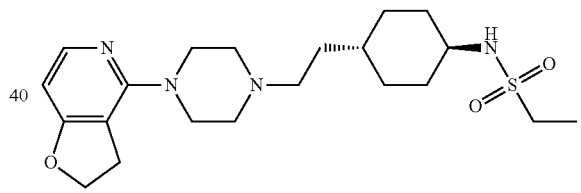

The title compound, white solid (92 mg, 87%), MS (ISP) m/z=423.3 [(M+H)$^+$], mp 224° C., was prepared in accordance with the general method of example 48 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and ethanesulfonyl chloride.

Example 50 trans-N-(4-{2-[4-(2,3-Dihydro-furo[3,2-c]pyridin-4-yl)-piperazin-1-yl]-ethyl}-cyclohexyl)-4-fluoro-benzenesulfonamide

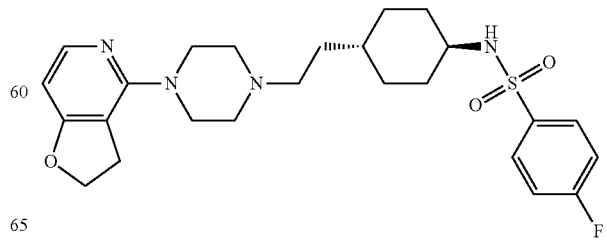

The title compound, light yellow solid (109 mg, 89%), MS (ISP) m/z=489.4 [(M+H)⁺], mp 221° C., was prepared in accordance with the general method of example 48 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-fluoro-benzene-1-sulfonyl chloride.

Example 51 trans-2-Cyclopropyl-N-(4-{2-[4-(2,3-dihydro-furo[3,2-c]pyridin-4-yl)-piperazin-1-yl]-ethyl}-cyclohexyl)-acetamide

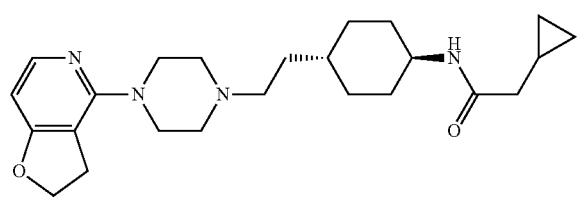 [SMILES: O=C(CC1CC1)N[C@H]1CC[C@H](CCN2CCN(c3nccc4c3CCO4)CC2)CC1]

The title compound, white solid (86 mg, 83%), MS (ISP) m/z=413.5 [(M+H)⁺], mp 193° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and cyclopropyl-acetic acid.

Example 52

Cyclobutanecarboxylic acid trans-(4-{2-[4-(2,3-dihydro-furo[3,2-c]pyridin-4-yl)-piperazin-1-yl]-ethyl}-cyclohexyl)-amide

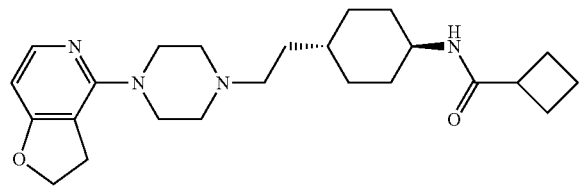 [SMILES: O=C(N[C@H]1CC[C@H](CCN2CCN(c3nccc4c3CCO4)CC2)CC1)C1CCC1]

The title compound, white solid (77 mg, 75%), MS (ISP) m/z=413.5 [(M+H)⁺], mp 202° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and cyclobutanecarboxylic acid.

Example 53 rac-Tetrahydro-pyran-3-carboxylic acid trans-(4-{2-[4-(2,3-dihydro-furo[3,2-c]pyridin-4-yl)-piperazin-1-yl]-ethyl}-cyclohexyl)-amide

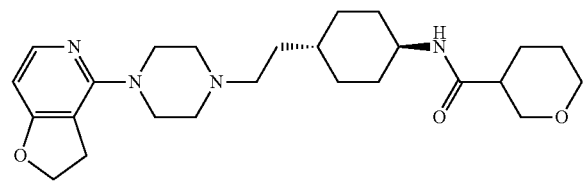 [SMILES: O=C(N[C@H]1CC[C@H](CCN2CCN(c3nccc4c3CCO4)CC2)CC1)C1CCCOC1]

The title compound, white solid (91 mg, 82%), MS (ISP) m/z=443.5 [(M+H)⁺], mp 216° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and rac-tetrahydro-pyran-3-carboxylic acid.

Example 54 trans-4-Hydroxy-4-methyl-cyclohexanecarboxylic acid trans-(4-{2-[4-(2,3-dihydro-furo[3,2-c]pyridin-4-yl)-piperazin-1-yl]-ethyl}-cyclohexyl)-amide

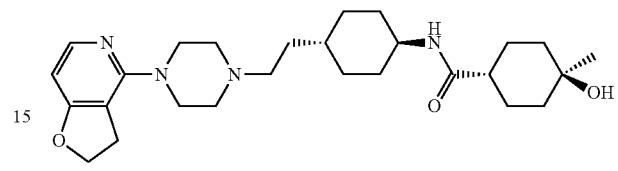

The title compound, light brown solid (56 mg, 48%), MS (ISP) m/z=471.5 [(M+H)⁺], mp 171° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and trans-4-hydroxy-4-methyl-cyclohexanecarboxylic acid.

Example 55 cis-4-Hydroxy-4-methyl-cyclohexanecarboxylic acid trans-(4-{2-[4-(2,3-dihydro-furo[3,2-c]pyridin-4-yl)-piperazin-1-yl]-ethyl}-cyclohexyl)-amide

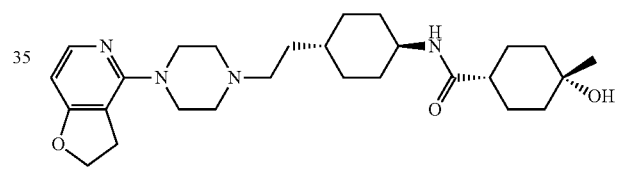

The title compound, off-white solid (79 mg, 67%), MS (ISP) m/z=471.5 [(M+H)⁺], mp 216.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and cis-4-hydroxy-4-methyl-cyclohexanecarboxylic acid.

Example 56 trans-N-(4-{2-[4-(2,3-Dihydro-furo[3,2-c]pyridin-4-yl)-piperazin-1-yl]-ethyl}-cyclohexyl)-4-piperidin-1-yl-benzamide

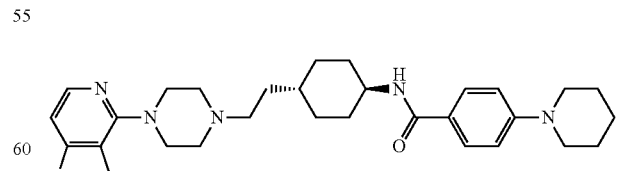

The title compound, off-white solid (100 mg, 77%), MS (ISP) m/z=518.5 [(M+H)⁺], mp 214.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-piperidin-1-yl-benzoic acid.

Example 57 trans-N-(4-{2-[4-(2,3-Dihydro-furo[3,2-c]pyridin-4-yl)-piperazin-1-yl]-ethyl}-cyclohexyl)-4-morpholin-4-yl-benzamide

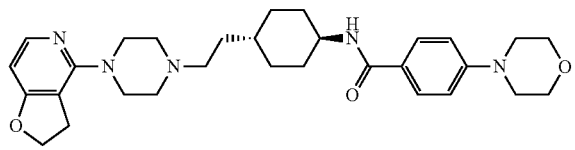 [SMILES: O=C(N[C@H]1CC[C@H](CCN2CCN(c3nccc4c3CCO4)CC2)CC1)c1ccc(N2CCOCC2)cc1]

The title compound, off-white solid (104 mg, 80%), MS (ISP) m/z=520.5 [(M+H)⁺], mp 228.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-morpholin-4-yl-benzoic acid.

Example 58

1-Hydroxy-cyclopropanecarboxylic acid trans-(4-{2-[4-(2,3-dihydro-furo[3,2-c]pyridin-4-yl)-piperazin-1-yl]-ethyl}-cyclohexyl)-amide

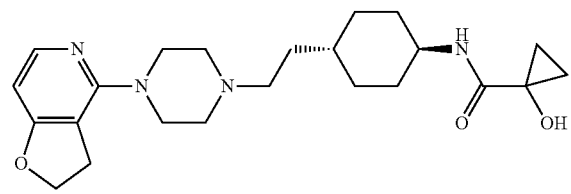 [SMILES: O=C(N[C@H]1CC[C@H](CCN2CCN(c3nccc4c3CCO4)CC2)CC1)C1(O)CC1]

The title compound, off-white solid (41 mg, 40%), MS (ISP) m/z=415.4 [(M+H)⁺], mp 174.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 1-hydroxy-cyclopropanecarboxylic acid.

Example 59 trans-2-Cyano-N-(4-{2-[4-(2,3-dihydro-furo[3,2-c]pyridin-4-yl)-piperazin-1-yl]-ethyl}-cyclohexyl)-acetamide

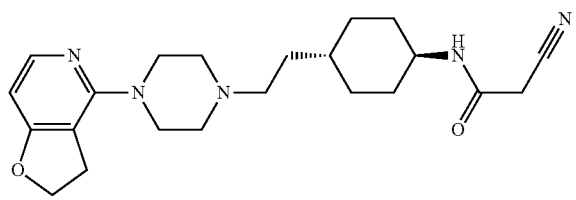 [SMILES: N#CCC(=O)N[C@H]1CC[C@H](CCN2CCN(c3nccc4c3CCO4)CC2)CC1]

The title compound, off-white solid (86 mg, 87%), MS (ISP) m/z=398.3 [(M+H)⁺], mp 188° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and cyano-acetic acid.

Example 60 trans-N-(4-{2-[4-(2,3-Dihydro-furo[3,2-c]pyridin-4-yl)-piperazin-1-yl]-ethyl}-cyclohexyl)-3,3,3-trifluoro-propionamide

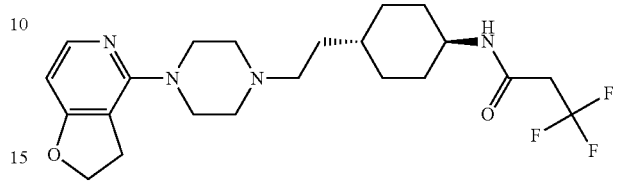

The title compound, white solid (89 mg, 81%), MS (ISP) m/z=441.3 [(M+H)⁺], mp 195.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 3,3,3-trifluoro-propionic acid.

Example 61 trans-N-(4-{2-[4-(2,3-Dihydro-furo[3,2-c]pyridin-4-yl)-piperazin-1-yl]-ethyl}-cyclohexyl)-2-(R)-[1,4]dioxan-2-yl-acetamide

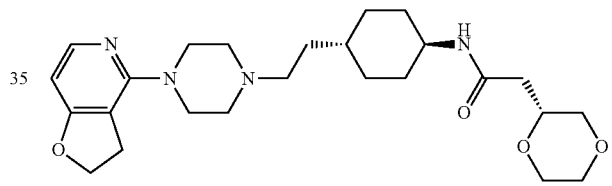

The title compound, white solid (92 mg, 80%), MS (ISP) m/z=459.5 [(M+H)⁺], mp 193.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and (R)-[1,4]dioxan-2-yl-acetic acid.

Example 62

Quinoline-4-carboxylic acid trans-(4-{2-[4-(2,3-dihydro-furo[3,2-c]pyridin-4-yl)-piperazin-1-yl]-ethyl}-cyclohexyl)-amide

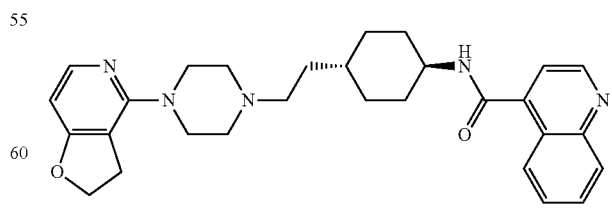

The title compound, white solid (104 mg, 86%), MS (ISP) m/z=486.5 [(M+H)⁺], mp 210° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (110 mg, 0.25 mmol) and quinoline-4-carboxylic acid.

Example 63

Cyclopropanecarboxylic acid trans-(4-{2-[4-(2,3-dihydro-furo[3,2-c]pyridin-4-yl)-piperazin-1-yl]-ethyl}-cyclohexyl)-amide

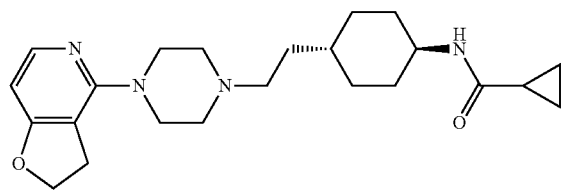 [SMILES: O=C(N[C@H]1CC[C@H](CCN2CCN(c3nccc4c3CCO4)CC2)CC1)C1CC1]

The title compound, white solid (86 mg, 86%), MS (ISP) m/z=399.3 [(M+H)$^+$], mp 213° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and cyclopropanecarboxylic acid.

Example 64 trans-N-(4-{2-[4-(2,3-Dihydro-furo[3,2-c]pyridin-4-yl)-piperazin-1-yl]-ethyl}-cyclohexyl)-2-rac-(tetrahydro-furan-2-yl)-acetamide

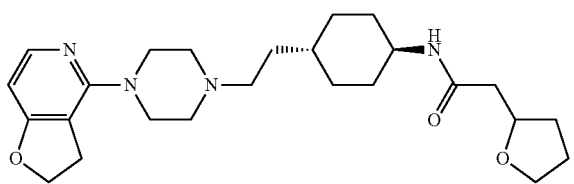 [SMILES: O=C(CC1CCCO1)N[C@H]1CC[C@H](CCN2CCN(c3nccc4c3CCO4)CC2)CC1]

The title compound, white solid (85 mg, 77%), MS (ISP) m/z=443.5 [(M+H)$^+$], mp 181.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and rac-(tetrahydro-furan-2-yl)-acetic acid.

Example 65 trans-N-(4-{2-[4-(2,3-Dihydro-furo[3,2-c]pyridin-4-yl)-piperazin-1-yl]-ethyl}-cyclohexyl)-2-trans-(4-methoxy-cyclohexyl)-acetamide

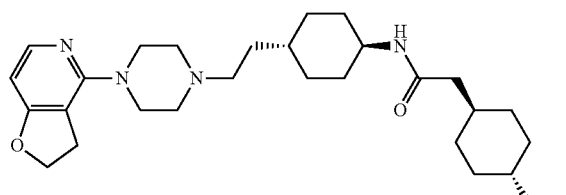

The title compound, white solid (106 mg, 88%), MS (ISP) m/z=485.6 [(M+H)$^+$], mp 192.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and trans-(4-methoxy-cyclohexyl)-acetic acid.

Example 66

N'-trans-(4-{2-[4-(2,3-dihydro-furo[3,2-c]pyridin-4-yl)-piperazin-1-yl]-ethyl}-cyclohexyl)-N,N-dimethyl-sulfamide

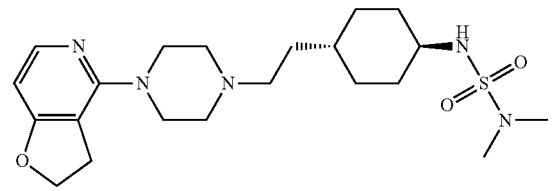 [SMILES: CN(C)S(=O)(=O)N[C@H]1CC[C@H](CCN2CCN(c3nccc4c3CCO4)CC2)CC1]

The title compound, light yellow solid (32 mg, 29%), MS (ISP) m/z=438.4 [(M+H)$^+$], mp 139.5° C., was prepared in accordance with the general method of example 48 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and N,N-dimethylsulfamoyl chloride.

Example 67 trans-N-(4-{2-[4-(2,3-Dihydro-furo[3,2-c]pyridin-4-yl)-piperazin-1-yl]-ethyl}-cyclohexyl)-2-(S)-[1,4]dioxan-2-yl-acetamide

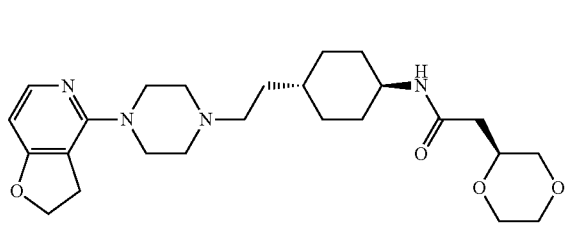 [SMILES: O=C(C[C@H]1COCCO1)N[C@H]1CC[C@H](CCN2CCN(c3nccc4c3CCO4)CC2)CC1]

The title compound, white solid (107 mg, 93%), MS (ISP) m/z=459.5 [(M+H)$^+$], mp 192° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and (S)-[1,4]dioxan-2-yl-acetic acid.

Example 68 trans-N-(4-{2-[4-(2,3-Dihydro-furo[3,2-c]pyridin-4-yl)-piperazin-1-yl]-ethyl}-cyclohexyl)-2-(R)-(tetrahydro-furan-2-yl)-acetamide

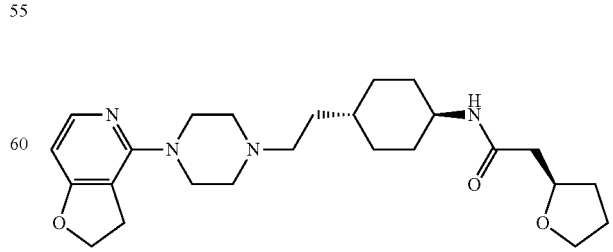

The title compound, white solid (87 mg, 79%), MS (ISP) m/z=443.5 [(M+H)$^+$], mp 183° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and (R)-(tetrahydro-furan-2-yl)-acetic acid.

Example 69 trans-N-(4-{2-[4-(2,3-Dihydro-furo[3,2-c]pyridin-4-yl)-piperazin-1-yl]-ethyl}-cyclohexyl)-2-(S)-(tetrahydro-furan-2-yl)-acetamide

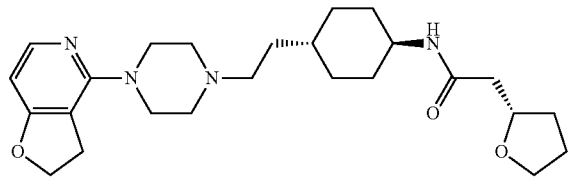

The title compound, white solid (91 mg, 82%), MS (ISP) m/z=443.6 [(M+H)⁺], mp 183.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and (S)-(tetrahydro-furan-2-yl)-acetic acid.

Example 70 trans-N-(4-{2-[4-(2,3-Dihydro-furo[3,2-c]pyridin-4-yl)-piperazin-1-yl]-ethyl}-cyclohexyl)-2,2-dimethyl-propionamide

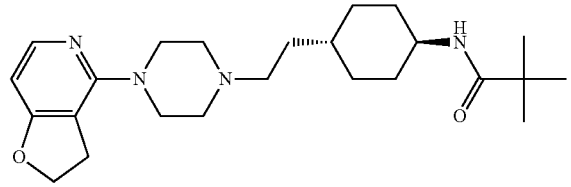

The title compound, white solid (70 mg, 68%), MS (ISP) m/z=415.4 [(M+H)⁺], mp 185° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 2,2-dimethyl-propionic acid.

Example 71 trans-N-(4-{2-[4-(2,3-Dihydro-furo[3,2-c]pyridin-4-yl)-piperazin-1-yl]-ethyl}-cyclohexyl)-3-methyl-butyramide

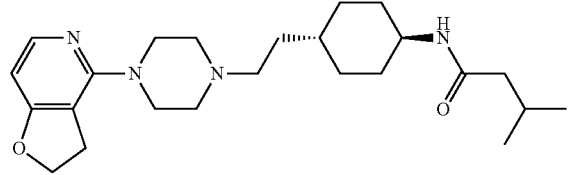

The title compound, white solid (84 mg, 81%), MS (ISP) m/z=415.4 [(M+H)⁺], mp 202.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 3-methyl-butyric acid.

Example 72 trans-N-(4-{2-[4-(2,3-Dihydro-furo[3,2-c]pyridin-4-yl)-piperazin-1-yl]-ethyl}-cyclohexyl)-3,3-dimethyl-butyramide

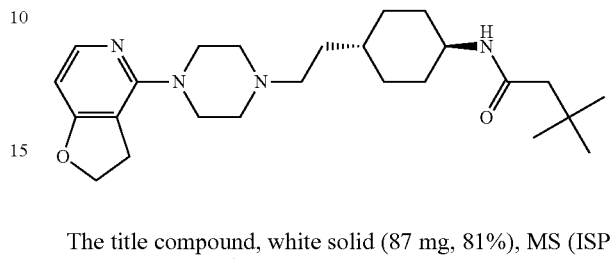

The title compound, white solid (87 mg, 81%), MS (ISP) m/z=429.4 [(M+H)⁺], mp 192.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 3,3-dimethyl-butyric acid.

Example 73 trans-2-Cyclobutyl-N-(4-{2-[4-(2,3-dihydro-furo[3,2-c]pyridin-4-yl)-piperazin-1-yl]-ethyl}-cyclohexyl)-acetamide

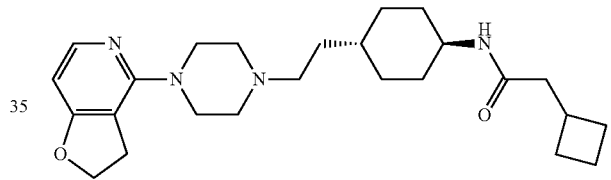

The title compound, white solid (81 mg, 76%), MS (ISP) m/z=427.5 [(M+H)⁺], mp 193° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and cyclobutane-acetic acid.

Example 74 trans-2,2-Difluoro-cyclopropanecarboxylic acid (4-{2-[4-(2,3-dihydro-furo[3,2-c]pyridin-4-yl)-piperazin-1-yl]-ethyl}-cyclohexyl)-amide

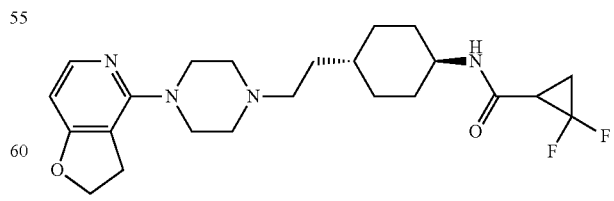

The title compound, white solid (92 mg, 85%), MS (ISP) m/z=435.4 [(M+H)⁺], mp 184.5° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (110 mg, 0.25 mmol) and 2,2-difluorocyclopropane-carboxylic acid.

Example 75 trans-N-(4-{2-[4-(2,3-Dihydro-furo[3,2-c]pyridin-4-yl)-piperazin-1-yl]-ethyl}-cyclohexyl)-isobutyramide

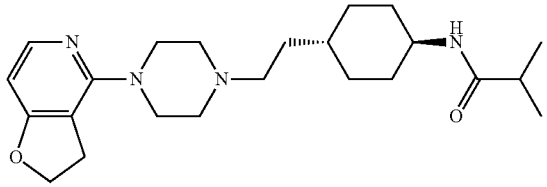 [SMILES: CC(C)C(=O)N[C@H]1CC[C@H](CCN2CCN(c3nccc4c3CCO4)CC2)CC1]

The title compound, white solid (62 mg, 62%), MS (ISP) m/z=401.5 [(M+H)+], mp 219° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and isobutyric acid.

Example 76 trans-N-(4-{2-[4-(2,3-Dihydro-furo[3,2-c]pyridin-4-yl)-piperazin-1-yl]-ethyl}-cyclohexyl)-rac-2-methyl-butyramide

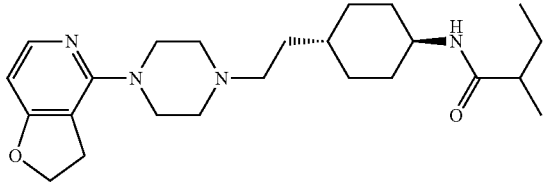 [SMILES: CCC(C)C(=O)N[C@H]1CC[C@H](CCN2CCN(c3nccc4c3CCO4)CC2)CC1]

The title compound, white solid (51 mg, 49%), MS (ISP) m/z=415.5 [(M+H)+], mp 205.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and rac-2-methylbutanoic acid

Example 77 trans-N-(4-{2-[4-(2,3-Dihydro-furo[3,2-c]pyridin-4-yl)-piperazin-1-yl]-ethyl}-cyclohexyl)-2-oxetan-3-yl-acetamide

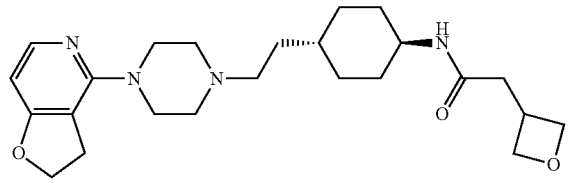 [SMILES: O=C(CC1COC1)N[C@H]1CC[C@H](CCN2CCN(c3nccc4c3CCO4)CC2)CC1]

The title compound, white solid (99 mg, 92%), MS (ISP) m/z=429.4 [(M+H)+], mp 195° C., was prepared in accordance with the general method of example 2 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and methyl 2-(oxetan-3-yl)acetate.

Example 78 trans-3-(4-{2-[4-(2,3-Dihydro-furo[3,2-c]pyridin-4-yl)-piperazin-1-yl]-ethyl}-cyclohexyl)-1,1-dimethyl-urea

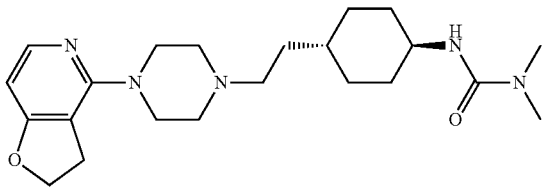 [SMILES: CN(C)C(=O)N[C@H]1CC[C@H](CCN2CCN(c3nccc4c3CCO4)CC2)CC1]

The title compound, white solid (90 mg, 90%), MS (ISP) m/z=402.5 [(M+H)+], mp 260° C., was prepared in accordance with the general method of example 48 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and dimethylcarbamic chloride.

Example 79 trans-N-(4-{2-[4-(2,3-Dihydro-furo[3,2-c]pyridin-4-yl)-piperazin-1-yl]-ethyl}-cyclohexyl)-2,2,2-trifluoro-acetamide

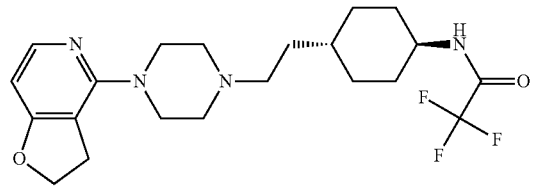 [SMILES: O=C(N[C@H]1CC[C@H](CCN2CCN(c3nccc4c3CCO4)CC2)CC1)C(F)(F)F]

The title compound, white solid (6.5 mg, 6%), MS (ISP) m/z=427.3 [(M+H)+], mp 213° C., was prepared in accordance with the general method of example 48 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and trifluoro acetic acid anhydride.

Example 80

3-Methyl-but-2-enoic acid trans-(4-{2-[4-(2,3-dihydro-furo[3,2-c]pyridin-4-yl)-piperazin-1-yl]-ethyl}-cyclohexyl)-amide

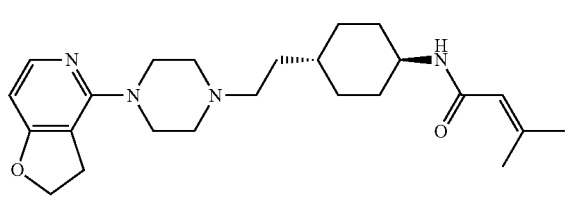 [SMILES: CC(C)=CC(=O)N[C@H]1CC[C@H](CCN2CCN(c3nccc4c3CCO4)CC2)CC1]

The title compound, off-white solid (78 mg, 76%), MS (ISP) m/z=413.5 [(M+H)+], mp 164.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 3-methyl-but-2-enoic acid.

Example 81

(E)-Pent-3-enoic acid trans-(4-{2-[4-(2,3-dihydro-furo[3,2-c]pyridin-4-yl)-piperazin-1-yl]-ethyl}-cyclohexyl)-amide

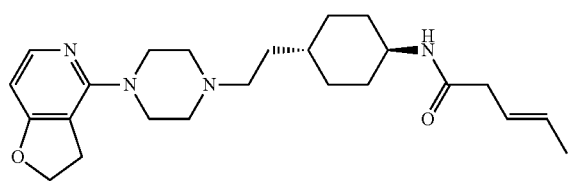

The title compound, white solid (95 mg, 92%), MS (ISP) m/z=413.5 [(M+H)+], mp 175.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and (E)-pent-3-enoic acid.

Example 82

But-2-ynoic acid trans-(4-{2-[4-(2,3-dihydro-furo[3,2-c]pyridin-4-yl)-piperazin-1-yl]-ethyl}-cyclohexyl)-amide

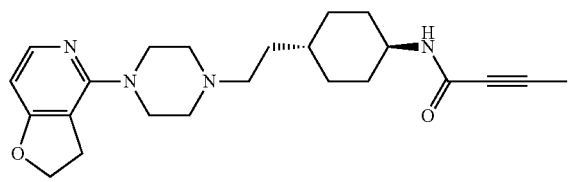 [SMILES: CC#CC(=O)N[C@H]1CC[C@H](CCN2CCN(c3nccc4c3CCO4)CC2)CC1]

The title compound, white solid (93 mg, 94%), MS (ISP) m/z=397.4 [(M+H)+], mp 193° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and but-2-ynoic acid.

Example 83 trans-N-(4-{2-[4-(2,3-Dihydro-furo[3,2-c]pyridin-4-yl)-piperazin-1-yl]-ethyl}-cyclohexyl)-formamide

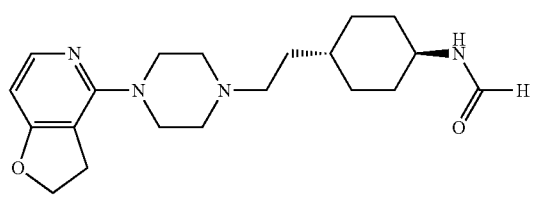 [SMILES: O=CN[C@H]1CC[C@H](CCN2CCN(c3nccc4c3CCO4)CC2)CC1]

The title compound, off-white solid (17 mg, 30%), MS (ISP) m/z=359.4 [(M+H)+], mp 170.5° C., was prepared in accordance with the general method of example 32 from trans-4-{2-[4-(2,3-dihydrofuro[3,2-c]pyridin-4-yl)-piper-azin-1-yl]-ethyl}-cyclohexanamine trihydrochloride (intermediate C) (70.4 mg, 0.16 mmol) and formic acid.

Example 84 trans-N-(4-{2-[4-(2,3-Dihydro-furo[3,2-c]pyridin-4-yl)-piperazin-1-yl]-ethyl}-cyclohexyl)-2-(3-methyl-isoxazol-5-yl)-acetamide

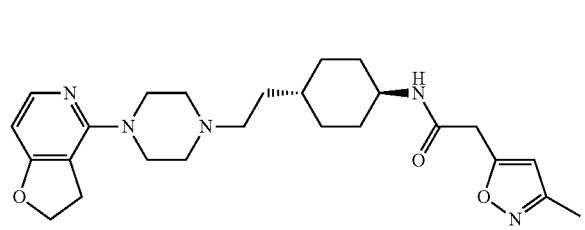 [SMILES: Cc1cc(CC(=O)N[C@H]2CC[C@H](CCN3CCN(c4nccc5c4CCO5)CC3)CC2)on1]

The title compound, white solid (68 mg, 75%), MS (ISP) m/z=454.4 [(M+H)+], mp 172.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and 2-(3-methylisoxazol-5-yl)-acetic acid.

Example 85

3-Methyl-isoxazole-5-carboxylic acid trans-(4-{2-[4-(2,3-dihydro-furo[3,2-c]pyridin-4-yl)-piperazin-1-yl]-ethyl}-cyclohexyl)-amide

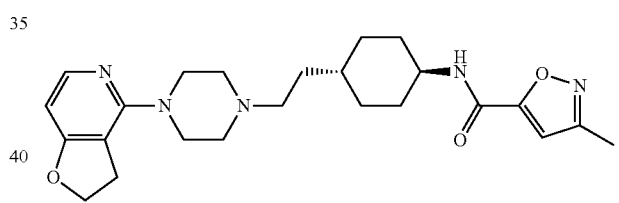

The title compound, off-white solid (62 mg, 71%), MS (ISP) m/z=440.4 [(M+H)+], mp 218° C., was prepared in accordance with the general method of example 32 from trans-4-{2-[4-(2,3-dihydrofuro[3,2-c]pyridin-4-yl)-piper-azin-1-yl]-ethyl}-cyclohexanamine trihydrochloride (intermediate C) (88 mg, 0.2 mmol) and 3-methylisoxazole-5-carboxylic acid.

Example 86 trans-N-(4-{2-[4-(2,3-Dihydro-furo[3,2-c]pyridin-4-yl)-piperazin-1-yl]-ethyl}-cyclohexyl)-N',N'-dimethyl-succinamide

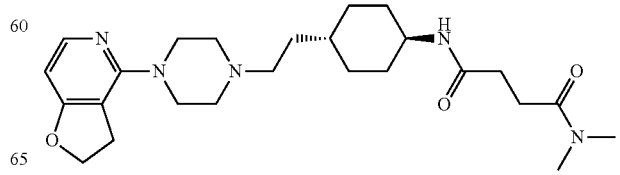

The title compound, white solid (48 mg, 52%), MS (ISP) m/z=458.6 [(M+H)⁺], mp 188° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and 4-(dimethylamino)-4-oxobutanoic acid.

Example 87 trans-N-(4-{2-[4-(2,3-Dihydro-furo[3,2-c]pyridin-4-yl)-piperazin-1-yl]-ethyl}-cyclohexyl)-3-hydroxy-3-methyl-butyramide

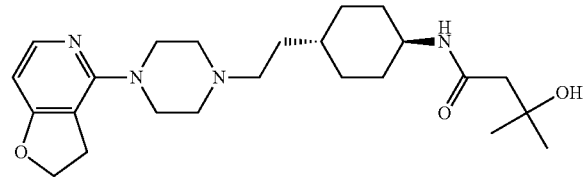 [SMILES: CC(C)(O)CC(=O)N[C@H]1CC[C@H](CCN2CCN(c3nccc4c3CCO4)CC2)CC1]

The title compound, off-white solid (68 mg, 79%), MS (ISP) m/z=431.6 [(M+H)⁺], mp 208° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and 3-hydroxy-3-methyl-butanoic acid.

Example 88 trans-(R)—N-(4-{2-[4-(2,3-Dihydro-furo[3,2-c]pyridin-4-yl)-piperazin-1-yl]-ethyl}-cyclohexyl)-4,4,4-trifluoro-3-hydroxy-butyramide

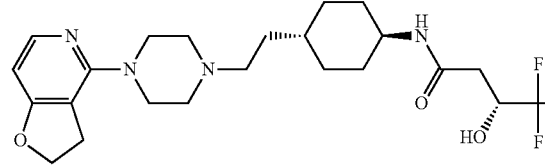

The title compound, white solid (72 mg, 77%), MS (ISP) m/z=471.5 [(M+H)⁺], mp 207° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and (R)-4,4,4-trifluoro-3-hydroxybutanoic acid.

Example 89

(S)-3-Hydroxy-pentanoic acid trans-(4-{2-[4-(2,3-dihydro-furo[3,2-c]pyridin-4-yl)-piperazin-1-yl]-ethyl}-cyclohexyl)-amide

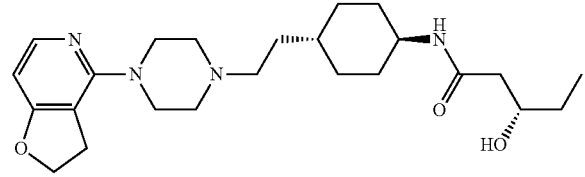 [SMILES: CC[C@H](O)CC(=O)N[C@H]1CC[C@H](CCN2CCN(c3nccc4c3CCO4)CC2)CC1]

The title compound, white solid (66 mg, 77%), MS (ISP) m/z=431.4 [(M+H)⁺], was prepared in accordance with the general method of example 2 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and (S)-methyl 3-hydroxy-pentanoate.

Example 90 trans-N-(4-{2-[4-(2,3-Dihydro-furo[3,2-c]pyridin-4-yl)-piperazin-1-yl]-ethyl}-cyclohexyl)-2-((1S,3S)-3-methoxy-cyclopentyl)-acetamide

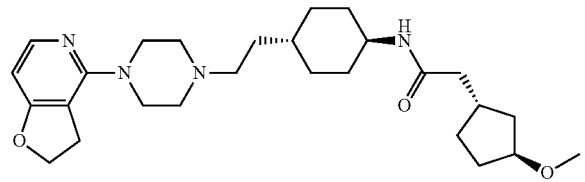 [SMILES: CO[C@H]1CC[C@H](CC(=O)N[C@H]2CC[C@H](CCN3CCN(c4nccc5c4CCO5)CC3)CC2)C1]

The title compound, white solid (80 mg, 85%), MS (ISP) m/z=471.6 [(M+H)⁺], mp 241° C., was prepared in accordance with the general method of example 2 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and methyl 2-((1S,3S)-3-methoxy-cyclopentyl)-acetate.

Example 91 trans-N-(4-{2-[4-(2,3-Dihydro-furo[3,2-c]pyridin-4-yl)-piperazin-1-yl]-ethyl}-cyclohexyl)-2-((S)-4-hydroxy-tetrahydro-furan-2-yl)-acetamide

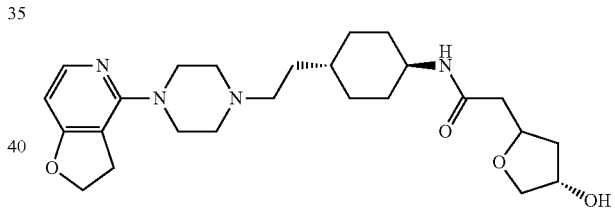

The title compound, off-white solid (14 mg, 15%), MS (ISP) m/z=459.5 [(M+H)⁺], mp 155° C., was prepared in accordance with the general method of example 2 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and ethyl 2#45)-4-hydroxy-tetrahydro-furan-2-yl)-acetate.

Example 92 trans-N-(4-{2-[4-(2,3-Dihydro-furo[3,2-c]pyridin-4-yl)-piperazin-1-yl]-ethyl}-cyclohexyl)-butyramide

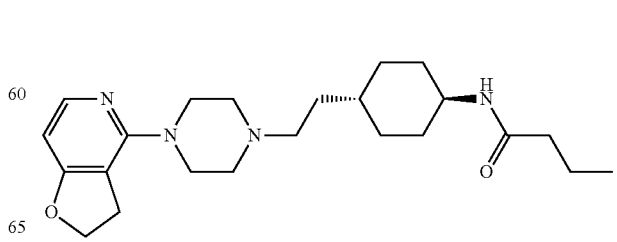

The title compound, white solid (54 mg, 67%), MS (ISP) m/z=401.5 [(M+H)+], mp 191° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and butyric acid.

Example 93

4-Methyl-pentanoic acid trans-(4-{2-[4-(2,3-dihydro-furo[3,2-c]pyridin-4-yl)-piperazin-1-yl]-ethyl}-cyclohexyl)-amide

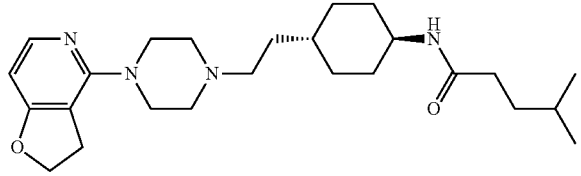 [SMILES: CCCCC(=O)N[C@H]1CC[C@H](CCN2CCN(c3nccc4c3CCO4)CC2)CC1]

The title compound, white solid (72 mg, 84%), MS (ISP) m/z=429.5 [(M+H)+], mp 182.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and 4-methyl-pentanoic acid.

Example 94

Pentanoic acid trans-(4-{2-[4-(2,3-dihydro-furo[3,2-c]pyridin-4-yl)-piperazin-1-yl]-ethyl}-cyclohexyl)-amide

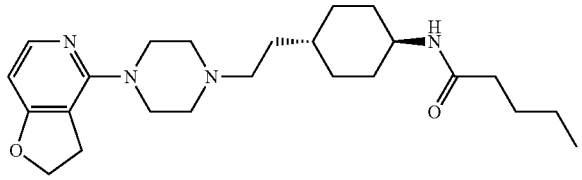

The title compound, white solid (54 mg, 65%), MS (ISP) m/z=415.5 [(M+H)+], mp 180.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and pentanoic acid.

Example 95 trans-N-(4-{2-[4-(2,3-Dihydro-furo[3,2-c]pyridin-4-yl)-piperazin-1-yl]-ethyl}-cyclohexyl)-4,4,4-trifluoro-butyramide

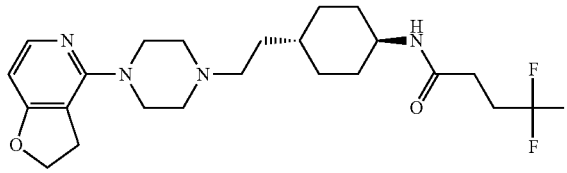

The title compound, white solid (53 mg, 58%), MS (ISP) m/z=455.4 [(M+H)+], mp 195.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (88 mg, 0.2 mmol) and 4,4,4-trifluoro-butanoic acid.

Example 96 trans-N-(4-{2-[4-(6-Methyl-furo[3,2-c]pyridin-4-yl)-piperazin-1-yl]-ethyl}-cyclohexyl)-acetamide

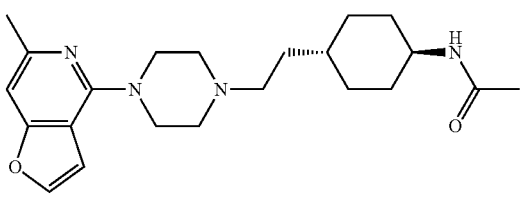 [SMILES: CC(=O)N[C@H]1CC[C@H](CCN2CCN(c3nc(C)cc4occc34)CC2)CC1]

The title compound, white solid (101 mg, 88%), MS (ISP) m/z=385.4 [(M+H)+], mp 207.5° C., was prepared in accordance with the general method of example 32 from trans-4-{2-[4-(6-methyl-furo[3,2-c]pyridin-4-yl)-piperazin-1-yl]-ethyl}-cyclohexylamine trihydrochloride (intermediate D) (136 mg, 0.3 mmol) and acetic acid.

Example 97 trans-Tetrahydro-pyran-4-carboxylic acid (4-{2-[4-(6-methyl-furo[3,2-c]pyridin-4-yl)-piperazin-1-yl]-ethyl}-cyclohexyl)-amide

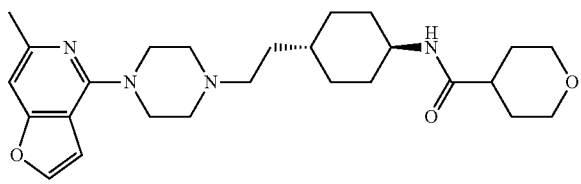 [SMILES: Cc1cc2occc2c(N2CCN(CC[C@H]3CC[C@H](NC(=O)C4CCOCC4)CC3)CC2)n1]

The title compound, off-white solid (128 mg, 94%), MS (ISP) m/z=455.4 [(M+H)+], mp 219° C., was prepared in accordance with the general method of example 32 from trans-4-{2-[4-(6-methyl-furo[3,2-c]pyridin-4-yl)-piperazin-1-yl]-ethyl}-cyclohexylamine trihydrochloride (intermediate D) (136 mg, 0.3 mmol) and tetrahydropyran-4-yl-carboxylic acid.

Example 98 trans-N-(4-{2-[4-(6-Methyl-furo[3,2-c]pyridin-4-yl)-piperazin-1-yl]-ethyl}-cyclohexyl)-2-(tetrahydro-pyran-4-yl)-acetamide

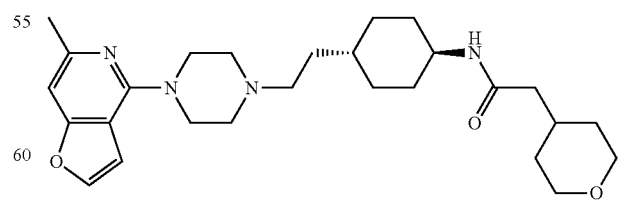

The title compound, off-white solid (131 mg, 93%), MS (ISP) m/z=469.5 [(M+H)+], mp 212.5° C., was prepared in accordance with the general method of example 32 from trans-4-{2-[4-(6-methyl-furo[3,2-c]pyridin-4-yl)-piperazin- 1-yl]-ethyl}-cyclohexylamine trihydrochloride (intermediate D) (136 mg, 0.3 mmol) and tetrahydropyran-4-yl-acetic acid.

Example 99 trans-3-Methoxy-N-(4-{2-[4-(6-methyl-furo[3,2-c]pyridin-4-yl)-piperazin-1-yl]-ethyl}-cyclohexyl)-propionamide

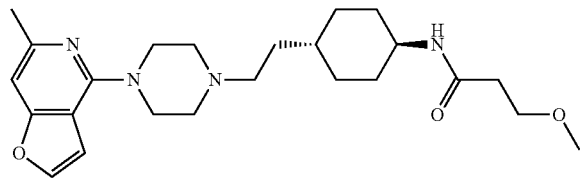 [SMILES: COCCC(=O)N[C@H]1CC[C@H](CCN2CCN(c3nc(C)cc4occc34)CC2)CC1]

The title compound, white solid (100 mg, 78%), MS (ISP) m/z=429.4 [(M+H)⁺], mp 158° C., was prepared in accordance with the general method of example 32 from trans-4-{2-[4-(6-methyl-furo[3,2-c]pyridin-4-yl)-piperazin-1-yl]-ethyl}-cyclohexylamine trihydrochloride (intermediate D) (136 mg, 0.3 mmol) and 3-methoxypropionic acid.

Example 100 trans-N-(4-{2-[4-(6-Methyl-2,3-dihydro-furo[3,2-c]pyridin-4-yl)-piperazin-1-yl]-ethyl}-cyclohexyl)-acetamide

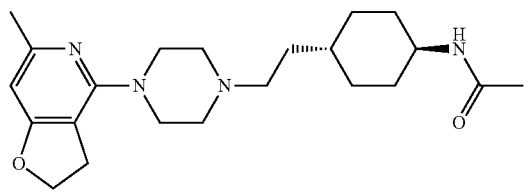 [SMILES: CC(=O)N[C@H]1CC[C@H](CCN2CCN(c3nc(C)cc4c3CCO4)CC2)CC1]

The title compound, white solid (96 mg, 83%), MS (ISP) m/z=387.4 [(M+H)⁺], mp 217.5° C., was prepared in accordance with the general method of example 32 from trans-4-{2-[4-(6-methyl-2,3-dihydro-furo[3,2-c]pyridin-4-yl)-piperazin-1-yl]-ethyl}-cyclohexylamine trihydrochloride (intermediate E) (136 mg, 0.3 mmol) and acetic acid.

Example 101

Tetrahydro-pyran-4-carboxylic acid trans-(4-{2-[4-(6-methyl-2,3-dihydro-furo[3,2-c]pyridin-4-yl)-piperazin-1-yl]-ethyl}-cyclohexyl)-amide

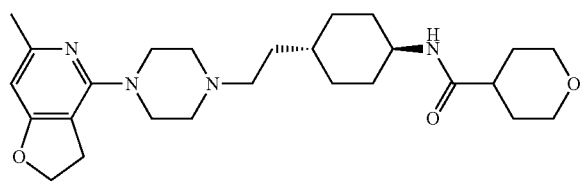

The title compound, white solid (124 mg, 91%), MS (ISP) m/z=457.5 [(M+H)⁺], mp 234.5° C., was prepared in accordance with the general method of example 32 from trans-4-{2-[4-(6-methyl-2,3-dihydro-furo[3,2-c]pyridin-4-yl)-piperazin-1-yl]-ethyl}-cyclohexylamine trihydrochloride (intermediate E) (136 mg, 0.3 mmol) and tetrahydropyran-4-yl-carboxylic acid.

Example 102 trans-N-(4-{2-[4-(6-Methyl-2,3-dihydro-furo[3,2-c]pyridin-4-yl)-piperazin-1-yl]-ethyl}-cyclohexyl)-2-(tetrahydro-pyran-4-yl)-acetamide

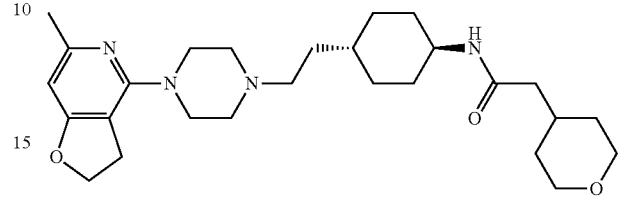

The title compound, white solid (126 mg, 89%), MS (ISP) m/z=471.6 [(M+H)⁺], mp 218.5° C., was prepared in accordance with the general method of example 32 from trans-4-{2-[4-(6-methyl-2,3-dihydro-furo[3,2-c]pyridin-4-yl)-piperazin-1-yl]-ethyl}-cyclohexylamine trihydrochloride (intermediate E) (136 mg, 0.3 mmol) and tetrahydropyran-4-yl-acetic acid.

Example 103 trans-3-Methoxy-N-(4-{2-[4-(6-methyl-2,3-dihydro-furo[3,2-c]pyridin-4-yl)-piperazin-1-yl]-ethyl}-cyclohexyl)-propionamide

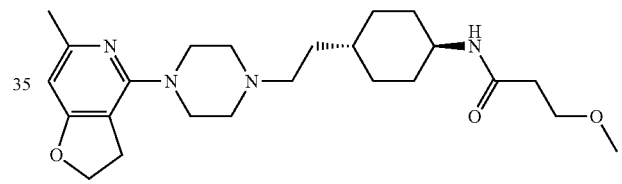

The title compound, white solid (97 mg, 75%), MS (ISP) m/z=431.5 [(M+H)⁺], mp 178.5° C., was prepared in accordance with the general method of example 32 from trans-4-{2-[4-(6-methyl-2,3-dihydro-furo[3,2-c]pyridin-4-yl)-piperazin-1-yl]-ethyl}-cyclohexylamine trihydrochloride (intermediate E) (136 mg, 0.3 mmol) and 3-methoxypropionic acid.

Example 104 trans-N-(4-{2-[4-(7-Methyl-furo[3,2-c]pyridin-4-yl)-piperazin-1-yl]-ethyl}-cyclohexyl)-acetamide

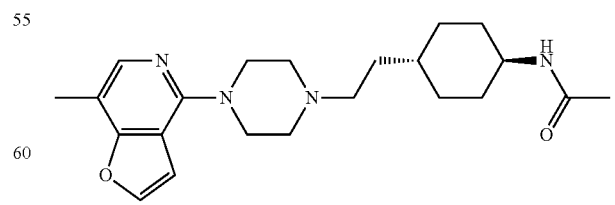

The title compound, white solid (106 mg, 92%), MS (ISP) m/z=385.4 [(M+H)⁺], mp 208° C., was prepared in accordance with the general method of example 32 from trans-4-{2-[4-(7-methyl-furo[3,2-c]pyridin-4-yl)-piperazin-1-yl]- ethyl}-cyclohexylamine trihydrochloride (intermediate F) (136 mg, 0.3 mmol) and acetic acid.

Example 105 trans-Tetrahydro-pyran-4-carboxylic acid (4-{2-[4-(7-methyl-furo[3,2-c]pyridin-4-yl)-piperazin-1-yl]-ethyl}-cyclohexyl)-amide

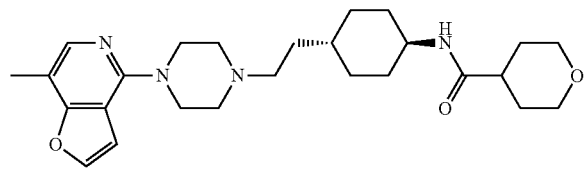 [SMILES: Cc1cnc(N2CCN(CC[C@H]3CC[C@H](NC(=O)C4CCOCC4)CC3)CC2)c2ccoc12]

The title compound, white solid (121 mg, 89%), MS (ISP) m/z=455.4 [(M+H)$^+$], mp 228° C., was prepared in accordance with the general method of example 32 from trans-4-{2-[4-(7-methyl-furo[3,2-c]pyridin-4-yl)-piperazin-1-yl]-ethyl}-cyclohexylamine trihydrochloride (intermediate F) (136 mg, 0.3 mmol) and tetrahydropyran-4-yl-carboxylic acid.

Example 106 trans-N-(4-{2-[4-(7-Methyl-furo[3,2-c]pyridin-4-yl)-piperazin-1-yl]-ethyl}-cyclohexyl)-2-(tetrahydro-pyran-4-yl)-acetamide

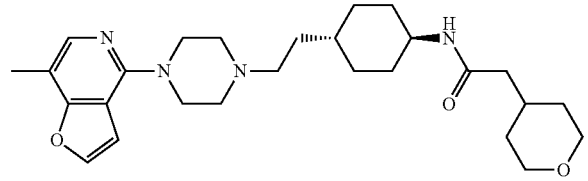 [SMILES: Cc1cnc(N2CCN(CC[C@H]3CC[C@H](NC(=O)CC4CCOCC4)CC3)CC2)c2ccoc12]

The title compound, white solid (115 mg, 82%), MS (ISP) m/z=469.5 [(M+H)$^+$], mp 205.5° C., was prepared in accordance with the general method of example 32 from trans-4-{2-[4-(7-methyl-furo[3,2-c]pyridin-4-yl)-piperazin-1-yl]-ethyl}-cyclohexylamine trihydrochloride (intermediate F) (136 mg, 0.3 mmol) and tetrahydropyran-4-yl-acetic acid.

Example 107 trans-3-Methoxy-N-(4-{2-[4-(7-methyl-furo[3,2-c]pyridin-4-yl)-piperazin-1-yl]-ethyl}-cyclohexyl)-propionamide

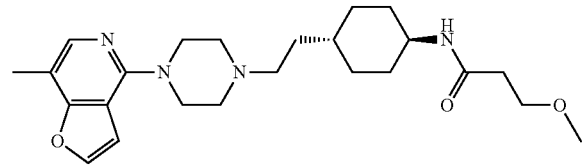

The title compound, white solid (79 mg, 61%), MS (ISP) m/z=429.4 [(M+H)$^+$], mp 177° C., was prepared in accordance with the general method of example 32 from trans-4-{2-[4-(7-methyl-furo[3,2-c]pyridin-4-yl)-piperazin-1-yl]-ethyl}-cyclohexylamine trihydrochloride (intermediate F) (136 mg, 0.3 mmol) and 3-methoxypropionic acid.

Example 108 trans-N-(4-{2-[4-(7-Methyl-2,3-dihydro-furo[3,2-c]pyridin-4-yl)-piperazin-1-yl]-ethyl}-cyclohexyl)-acetamide

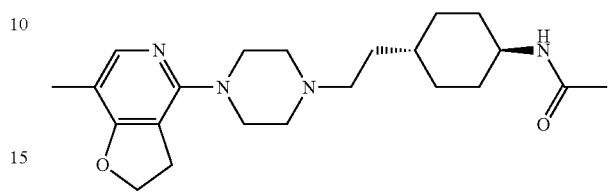

The title compound, off-white solid (47 mg, 81%), MS (ISP) m/z=387.4 [(M+H)$^+$], mp 196.5° C., was prepared in accordance with the general method of example 32 from trans-4-{2-[4-(7-methyl-2,3-dihydro-furo[3,2-c]pyridin-4-yl)-piperazin-1-yl]-ethyl}-cyclohexylamine trihydrochloride (intermediate G) (68.1 mg, 0.15 mmol) and acetic acid.

Example 109

Tetrahydro-pyran-4-carboxylic acid trans-(4-{2-[4-(7-methyl-2,3-dihydro-furo[3,2-c]pyridin-4-yl)-piperazin-1-yl]-ethyl}-cyclohexyl)-amide

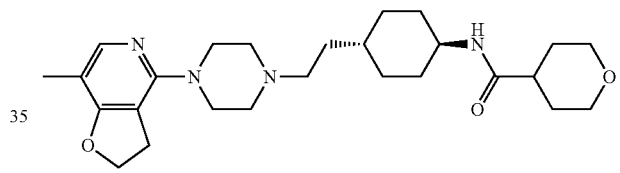

The title compound, white solid (60 mg, 88%), MS (ISP) m/z=457.5 [(M+H)$^+$], mp 223.5° C., was prepared in accordance with the general method of example 32 from trans-4-{2-[4-(7-methyl-2,3-dihydro-furo[3,2-c]pyridin-4-yl)-piperazin-1-yl]-ethyl}-cyclohexylamine trihydrochloride (intermediate G) (68.1 mg, 0.15 mmol) and tetrahydropyran-4-yl-carboxylic acid.

Example 110 trans-N-(4-{2-[4-(7-Methyl-2,3-dihydro-furo[3,2-c]pyridin-4-yl)-piperazin-1-yl]-ethyl}-cyclohexyl)-2-(tetrahydro-pyran-4-yl)-acetamide

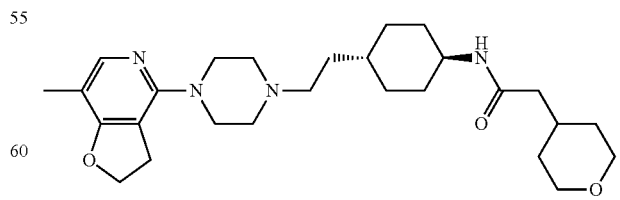

The title compound, white solid (52 mg, 74%), MS (ISP) m/z=471.6 [(M+H)$^+$], mp 199° C., was prepared in accordance with the general method of example 32 from trans-4-{2-[4-(7-methyl-2,3-dihydro-furo[3,2-c]pyridin-4-yl)-piper-

Example 111 trans-3-Methoxy-N-(4-{2-[4-(7-methyl-2,3-dihydro-furo[3,2-c]pyridin-4-yl)-piperazin-1-yl]-ethyl}-cyclohexyl)-propionamide

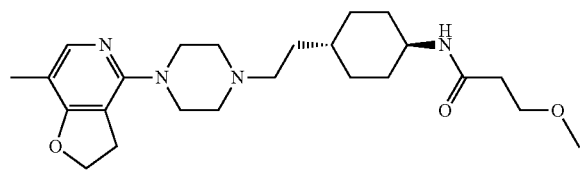

The title compound, off-white solid (53 mg, 82%), MS (ISP) m/z=431.6 [(M+H)⁺], mp 163.5° C., was prepared in accordance with the general method of example 32 from trans-4-{2-[4-(7-methyl-2,3-dihydro-furo[3,2-c]pyridin-4-yl)-piperazin-1-yl]-ethyl}-cyclohexylamine trihydrochloride (intermediate G) (68.1 mg, 0.15 mmol) and 3-methoxypropionic acid.

Example 112 trans-(RS)—N-(4-{2-[4-(2,3-Dihydro-furo[3,2-c]pyridin-4-yl)-piperazin-1-yl]-ethyl}-cyclohexyl)-3,3,3-trifluoro-2-hydroxy-propionamide

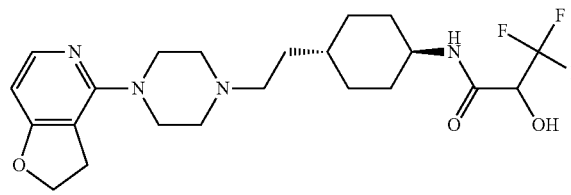

The title compound, light yellow solid (80 mg, 70%), MS (ISP) m/z=457.4 [(M+H)⁺], mp 204° C., was prepared in accordance with the general method of example 32 from trans-4-{2-[4-(6-methyl-2,3-dihydro-furo[3,2-c]pyridin-4-yl)-piperazin-1-yl]-ethyl}-cyclohexylamine trihydrochloride (intermediate E) (110 mg, 0.25 mmol) and (RS)-3,3,3-trifluoro-2-hydroxypropanoic acid.

Example 113 trans-N-(4-{2-[4-(2,3-Dihydro-furo[3,2-c]pyridin-4-yl)-piperazin-1-yl]-ethyl}-cyclohexyl)-3,3-dimethoxy-propionamide

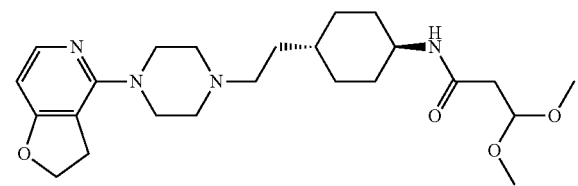 [SMILES: COC(CC(=O)N[C@H]1CC[C@H](CCN2CCN(c3nccc4c3CCO4)CC2)CC1)OC]

The title compound, white solid (101 mg, 91%), MS (ISP) m/z=447.4 [(M+H)⁺], mp 220° C., was prepared in accordance with the general method of example 2 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and methyl 3,3-dimethoxy-propanoate.

Example 114 trans-N-(4-{2-[4-(2,3-Dihydro-furo[3,2-c]pyridin-4-yl)-piperazin-1-yl]-ethyl}-cyclohexyl)-4,4-dimethoxy-butyramide

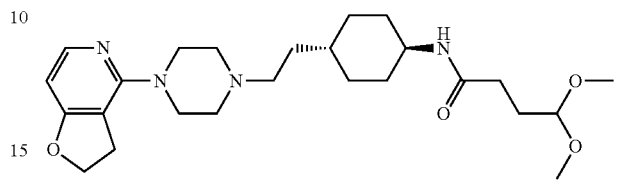

The title compound, white solid (114 mg, 99%), MS (ISP) m/z=461.5 [(M+H)⁺], mp 205.5° C., was prepared in accordance with the general method of example 2 from trans-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and methyl 4,4-dimethoxy-butanoate.

Example 115

5-Methanesulfonyl-thiophene-2-carboxylic acid trans-(4-{2-[4-(2,3-dihydro-furo[3,2-c]pyridin-4-yl)-piperazin-1-yl]-ethyl}-cyclohexyl)-amide

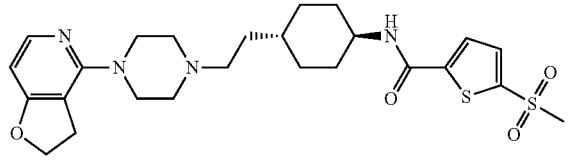 [SMILES: CS(=O)(=O)c1ccc(C(=O)N[C@H]2CC[C@H](CCN3CCN(c4nccc5c4CCO5)CC3)CC2)s1]

The title compound, off-white solid (98 mg, 76%), MS (ISP) m/z=519.2 [(M+H)⁺], mp 229° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 5-methanesulfonyl-thiophene-2-carboxylic acid.

Example 116 trans-N-(4-{2-[4-(2,3-Dihydro-furo[3,2-c]pyridin-4-yl)-piperazin-1-yl]-ethyl}-cyclohexyl)-6-methyl-nicotinamide

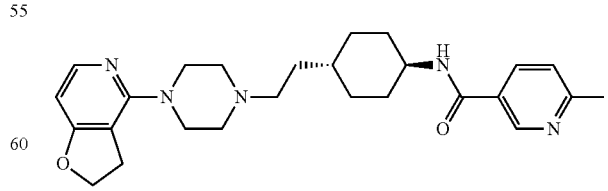

The title compound, white solid (100 mg, 89%), MS (ISP) m/z=450.4 [(M+H)⁺], mp 201° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (110 mg, 0.25 mmol) and 6-methyl-nicotinic acid.

Example 117 trans-4-Cyano-N-(4-{2-[4-(2,3-dihydro-furo[3,2-c]pyridin-4-yl)-piperazin-1-yl]-ethyl}-cyclohexyl)-benzamide

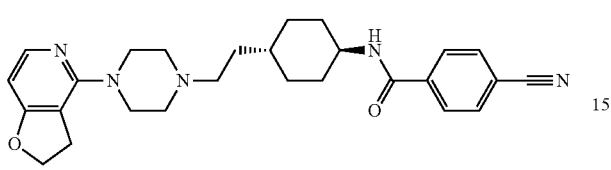

The title compound, off-white solid (110 mg, 96%), MS (ISP) m/z=460.5 [(M+H)$^+$], mp 243.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-cyano-benzoic acid.

Example 118 trans-N-(4-{2-[4-(2,3-Dihydro-furo[3,2-c]pyridin-4-yl)-piperazin-1-yl]-ethyl}-cyclohexyl)-4-(4-methyl-piperazin-1-yl)-benzamide

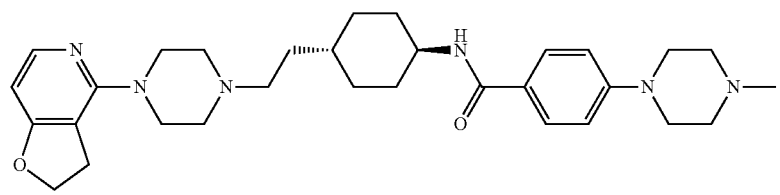 [SMILES: CN1CCN(c2ccc(C(=O)N[C@H]3CC[C@H](CCN4CCN(c5nccc6c5CCO6)CC4)CC3)cc2)CC1]

The title compound, white solid (95 mg, 71%), MS (ISP) m/z=533.3 [(M+H)$^+$], mp 236° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-(4-methyl-piperazin-1-yl)-benzoic acid.

Example 119 trans-N-(4-{2-[4-(2,3-Dihydro-furo[3,2-c]pyridin-4-yl)-piperazin-1-yl]-ethyl}-cyclohexyl)-6-morpholin-4-yl-nicotinamide

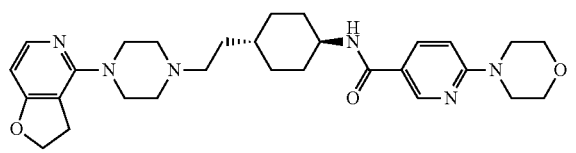

The title compound, white solid (108 mg, 83%), MS (ISP) m/z=521.5 [(M+H)$^+$], mp 222° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 6-morpholin-4-yl-nicotinic acid.

Example 120 trans-N-(4-{2-[4-(2,3-Dihydro-furo[3,2-c]pyridin-4-yl)-piperazin-1-yl]-ethyl}-cyclohexyl)-4-pyridin-3-yl-benzamide

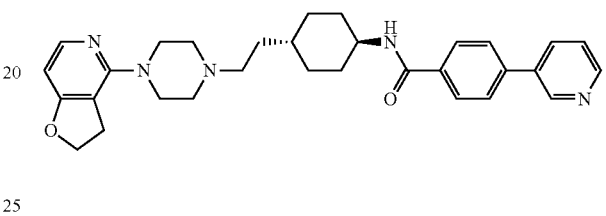

The title compound, white solid (110 mg, 86%), MS (ISP) m/z=512.5 [(M+H)$^+$], mp 218° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-pyridin-3-yl-benzoic acid.

Example 121

Benzo[1,3]dioxole-5-carboxylic acid trans-(4-{2-[4-(2,3-dihydro-furo[3,2-c]pyridin-4-yl)-piperazin-1-yl]-ethyl}-cyclohexyl)-amide

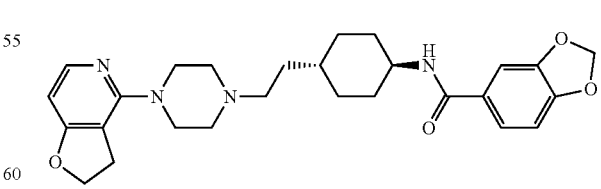

The title compound, white solid (107 mg, 89%), MS (ISP) m/z=479.3 [(M+H)$^+$], mp 243.5° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (110 mg, 0.25 mmol) and benzo[1,3]dioxole-5-carboxylic acid.

Example 122 trans-2-Benzo[1,3]dioxol-5-yl-N-(4-{2-[4-(2,3-dihydro-furo[3,2-c]pyridin-4-yl)-piperazin-1-yl]-ethyl}-cyclohexyl)-acetamide

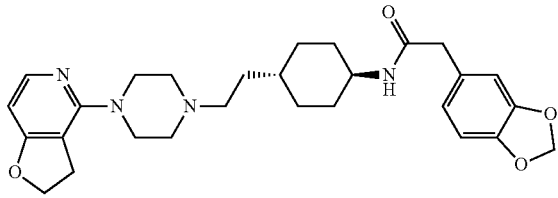 [SMILES: O=C(Cc1ccc2c(c1)OCO2)N[C@H]1CC[C@H](CCN2CCN(c3nccc4c3CCO4)CC2)CC1]

The title compound, white solid (110 mg, 89%), MS (ISP) m/z=493.4 [(M+H)$^+$], mp 212° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 2-(benzo[1,3]dioxol-5-yl)-acetic acid.

Example 123

1-Hydroxy-cyclobutanecarboxylic acid trans-(4-{2-[4-(2,3-dihydro-furo[3,2-c]pyridin-4-yl)-piperazin-1-yl]-ethyl}-cyclohexyl)-amide

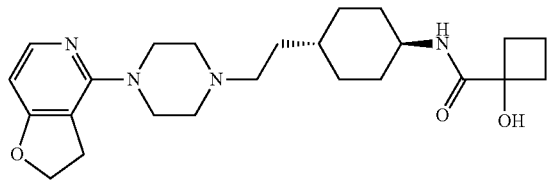 [SMILES: O=C(N[C@H]1CC[C@H](CCN2CCN(c3nccc4c3CCO4)CC2)CC1)C1(O)CCC1]

The title compound, white solid (81 mg, 76%), MS (ISP) m/z=429.4 [(M+H)$^+$], mp 177.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 1-hydroxy-cyclobutane-carboxylic acid.

Example 124 trans-N-(4-{2-[4-(2,3-Dihydro-furo[3,2-c]pyridin-4-yl)-piperazin-1-yl]-ethyl}-cyclohexyl)-2-hydroxy-2-methyl-propionamide

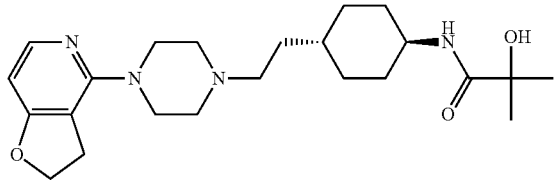 [SMILES: CC(C)(O)C(=O)N[C@H]1CC[C@H](CCN2CCN(c3nccc4c3CCO4)CC2)CC1]

The title compound, white solid (101 mg, 97%), MS (ISP) m/z=517.4 [(M+H)$^+$], mp 201° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 2-hydroxy-2-methyl-propionic acid.

Example 125 trans-N-(4-{2-[4-(2,3-Dihydro-furo[3,2-c]pyridin-4-yl)-piperazin-1-yl]-ethyl}-cyclohexyl)-4-(1,1-dioxo-1λ6-thiomorpholin-4-yl)-benzamide

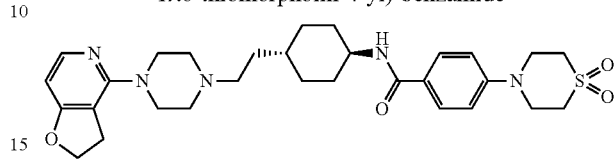

The title compound, white solid (129 mg, 91%), MS (ISP) m/z=568.4 [(M+H)$^+$], mp 261.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-(1,1-dioxo-1λ6-thiomorpholin-4-yl)-benzoic acid.

Example 126 trans-N-(4-{2-[4-(2,3-Dihydro-furo[3,2-c]pyridin-4-yl)-piperazin-1-yl]-ethyl}-cyclohexyl)-4-pyrazol-1-yl-benzamide

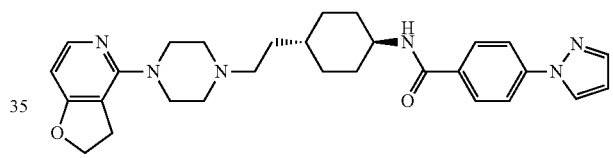

The title compound, white solid (109 mg, 87%), MS (ISP) m/z=501.3 [(M+H)$^+$], mp 229° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-pyrazol-1-yl-benzoic acid.

Example 127 trans-N-(4-{2-[4-(2,3-Dihydro-furo[3,2-c]pyridin-4-yl)-piperazin-1-yl]-ethyl}-cyclohexyl)-3-(5-methyl-[1,2,4]oxadiazol-3-yl)-benzamide

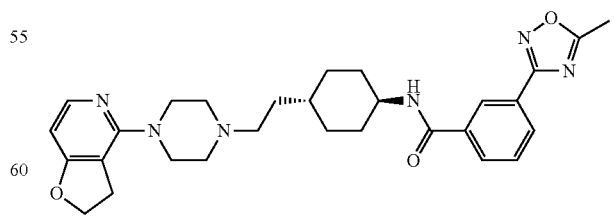

The title compound, white solid (125 mg, 97%), MS (ISP) m/z=517.4 [(M+H)$^+$], mp 218° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (110 mg, 0.25 mmol) and 3-(5-methyl-[1,2,4]oxadiazol-3-yl)-benzoic acid.

Example 128

Quinoline-6-carboxylic acid trans-(4-{2-[4-(2,3-dihydro-furo[3,2-c]pyridin-4-yl)-piperazin-1-yl]-ethyl}-cyclohexyl)-amide

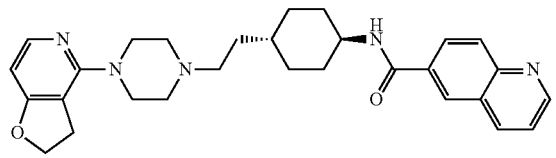 [SMILES: O=C(N[C@H]1CC[C@H](CCN2CCN(c3nccc4c3CCO4)CC2)CC1)c1ccc2ncccc2c1]

The title compound, off-white solid (120 mg, 99%), MS (ISP) m/z=486.4 [(M+H)+], mp 227° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and quinoline-6-carboxylic acid.

Example 129 trans-2-Benzo[d]isoxazol-3-yl-N-(4-{2-[4-(2,3-dihydro-furo[3,2-c]pyridin-4-yl)-piperazin-1-yl]-ethyl}-cyclohexyl)-acetamide

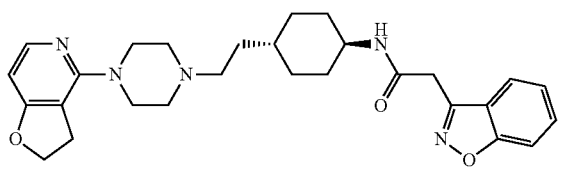 [SMILES: O=C(Cc1noc2ccccc12)N[C@H]1CC[C@H](CCN2CCN(c3nccc4c3CCO4)CC2)CC1]

The title compound, white solid (114 mg, 93%), MS (ISP) m/z=490.4 [(M+H)+], mp 217.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 2-benzo[d]isoxazol-3-yl-acetic acid.

Example 130

5-Morpholin-4-yl-pyrazine-2-carboxylic acid trans-(4-{2-[4-(2,3-dihydro-furo[3,2-c]pyridin-4-yl)-piperazin-1-yl]-ethyl}-cyclohexyl)-amide

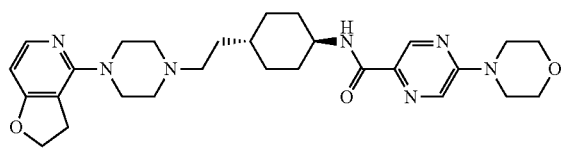 [SMILES: O=C(N[C@H]1CC[C@H](CCN2CCN(c3nccc4c3CCO4)CC2)CC1)c1cnc(N2CCOCC2)cn1]

The title compound, white solid (107 mg, 82%), MS (ISP) m/z=522.5 [(M+H)+], mp 192.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 5-morpholin-4-yl-pyrazine-2-carboxylic acid.

Example 131 trans-4-tert-Butyl-N-(4-{2-[4-(2,3-dihydro-furo[3,2-c]pyridin-4-yl)-piperazin-1-yl]-ethyl}-cyclohexyl)-benzamide

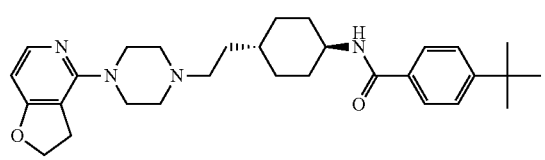

The title compound, white solid (80 mg, 65%), MS (ISP) m/z=491.5 [(M+H)+], mp 186.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-tert-butyl-benzoic acid.

Example 132 trans-2,4-Dichloro-N-(4-{2-[4-(2,3-dihydro-furo[3,2-c]pyridin-4-yl)-piperazin-1-yl]-ethyl}-cyclohexyl)-benzamide

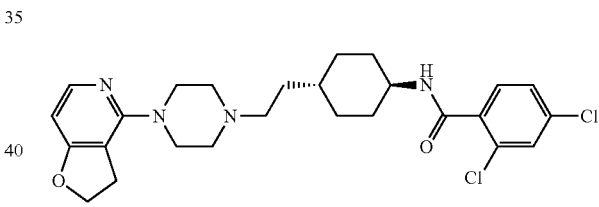

The title compound, white solid (92 mg, 73%), MS (ISP) m/z=503.2 [(M+H)+], mp 203.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 2,4-dichloro-benzoic acid.

Example 133 trans-N-(4-{2-[4-(2,3-Dihydro-furo[3,2-c]pyridin-4-yl)-piperazin-1-yl]-ethyl}-cyclohexyl)-4-pyrrol-1-yl-benzamide

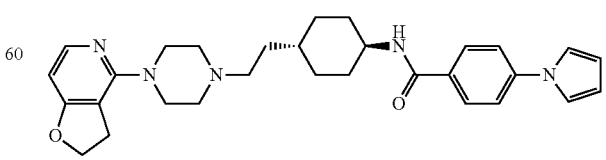

The title compound, white solid (72 mg, 58%), MS (ISP) m/z=500.4 [(M+H)+], mp 234° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-pyrrol-1-yl-benzoic acid.

Example 134

Biphenyl-4-carboxylic acid trans-(4-{2-[4-(2,3-dihydro-furo[3,2-c]pyridin-4-yl)-piperazin-1-yl]-ethyl}-cyclohexyl)-amide

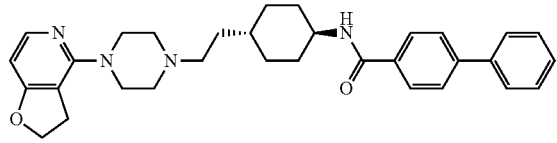 [SMILES: O=C(N[C@H]1CC[C@H](CCN2CCN(c3nccc4c3CCO4)CC2)CC1)c1ccc(-c2ccccc2)cc1]

The title compound, white solid (93 mg, 73%), MS (ISP) m/z=511.6 [(M+H)+], mp 232° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and biphenyl-4-carboxylic acid.

Example 135 trans-(R)—N-(4-{2-[4-(2,3-Dihydro-furo[3,2-c]pyridin-4-yl)-piperazin-1-yl]-ethyl}-cyclohexyl)-2-methoxy-propionamide

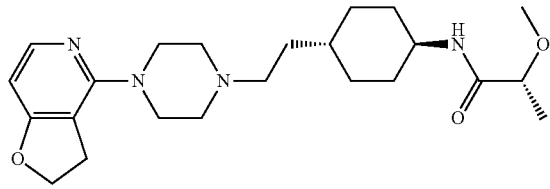 [SMILES: CO[C@H](C)C(=O)N[C@H]1CC[C@H](CCN2CCN(c3nccc4c3CCO4)CC2)CC1]

The title compound, off-white solid (65 mg, 62%), MS (ISP) m/z=417.4 [(M+H)+], mp 159° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and (R)-2-methoxy-propanoic acid.

Example 136 trans-4-tert-Butoxy-N-(4-{2-[4-(2,3-dihydro-furo[3,2-c]pyridin-4-yl)-piperazin-1-yl]-ethyl}-cyclohexyl)-benzamide

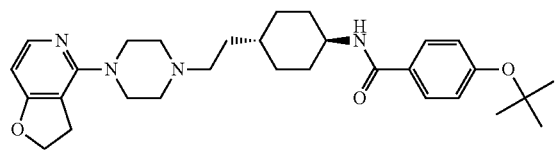 [SMILES: CC(C)(C)Oc1ccc(C(=O)N[C@H]2CC[C@H](CCN3CCN(c4nccc5c4CCO5)CC3)CC2)cc1]

The title compound, white solid (82 mg, 65%), MS (ISP) m/z=507.3 [(M+H)+], mp 200° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and 4-tert-butoxy-benzoic acid.

Example 137 trans-(S)—N-(4-{2-[4-(2,3-Dihydro-furo[3,2-c]pyridin-4-yl)-piperazin-1-yl]-ethyl}-cyclohexyl)-2-methoxy-propionamide

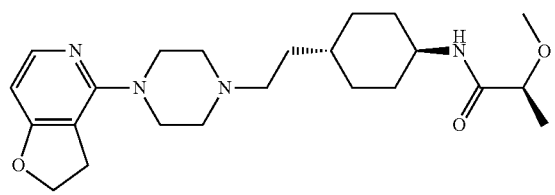 [SMILES: CO[C@@H](C)C(=O)N[C@H]1CC[C@H](CCN2CCN(c3nccc4c3CCO4)CC2)CC1]

The title compound, white solid (63 mg, 61%), MS (ISP) m/z=417.4 [(M+H)+], mp 158.5° C., was prepared in accordance with the general method of example 32 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and (S)-2-methoxy-propanoic acid.

Example 138 trans-N-(4-{2-[4-(2,3-Dihydro-furo[3,2-c]pyridin-4-yl)-piperazin-1-yl]-ethyl}-cyclohexyl)-benzene-sulfonamide

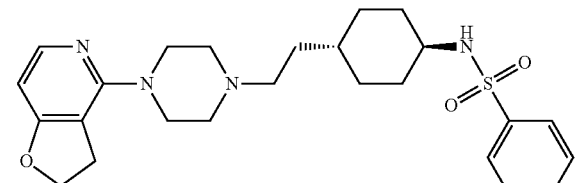

The title compound, light yellow solid (75 mg, 64%), MS (ISP) m/z=471.4 [(M+H)+], mp 168.5° C., was prepared in accordance with the general method of example 48 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and benzene-sulfonyl chloride.

Example 139 trans-N-(4-{2-[4-(2,3-Dihydro-furo[3,2-c]pyridin-4-yl)-piperazin-1-yl]-ethyl}-cyclohexyl)-3-methoxy-butyramide

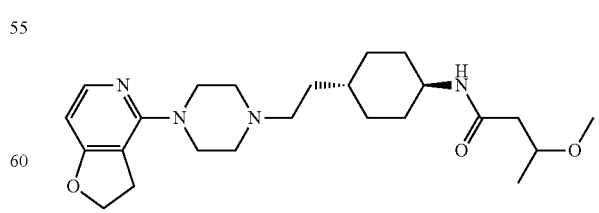

The title compound, white solid (54 mg, 50%), MS (ISP) m/z=431.5 [(M+H)+], mp 167° C., was prepared in accordance with the general method of example 32 from trans-4-{2-[4-(2,3-dihydrofuro[3,2-c]pyridin-4-yl)-piperazin-1-yl]- ethyl}-cyclohexanamine trihydrochloride (intermediate C) (110 mg, 0.25 mmol) and (RS)-3-methoxybutanoic acid.

Example 140

(R)-3-Hydroxy-pentanoic acid trans-(4-{2-[4-(2,3-dihydro-furo[3,2-c]pyridin-4-yl)-piperazin-1-yl]-ethyl}-cyclohexyl)-amide

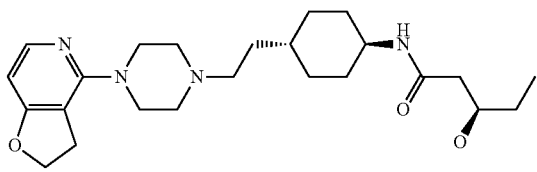 [SMILES: CC[C@@H](O)CC(=O)N[C@H]1CC[C@H](CCN2CCN(c3nccc4c3CCO4)CC2)CC1]

The title compound, white solid (58 mg, 54%), MS (ISP) m/z=431.5 [(M+H)$^+$], mp 161° C., was prepared in accordance with the general method of example 2 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and methyl (R)-3-hydroxy-pentanoate.

Example 141 trans-N-(4-{2-[4-(2,3-Dihydro-furo[3,2-c]pyridin-4-yl)-piperazin-1-yl]-ethyl}-cyclohexyl)-2-(1-hydroxy-cyclobutyl)-acetamide

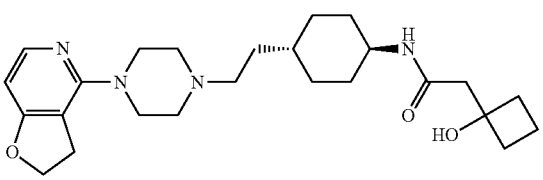 [SMILES: O=C(CC1(O)CCC1)N[C@H]1CC[C@H](CCN2CCN(c3nccc4c3CCO4)CC2)CC1]

The title compound, white solid (58 mg, 52%), MS (ISP) m/z=443.5 [(M+H)$^+$], mp 155° C., was prepared in accordance with the general method of example 2 from trans-4-{2-[4-(2,3-dihydrofuro[3,2-c]pyridin-4-yl)-piperazin-1-yl]-ethyl}-cyclohexanamine trihydrochloride (intermediate C) (110 mg, 0.25 mmol) and ethyl 2-(1-hydroxy-cyclobutyl)-acetate.

Biochemical Assay

The ability of the compounds to bind to the 5-HT$_{2A}$, D$_3$ and D$_2$ receptors was determined using radioligand binding to cloned receptors selectively expressed in HEK-293 EBNA cells.

Membrane Preparation

HEK293 EBNA cells were transiently transfected with expression plasmids encoding for the human D$_2$ or D$_3$ or for the human 5-HT$_{2A}$ receptor, respectively. The cells were harvested 48 h post-transfection, washed three times with cold PBS and stored at −80° C. prior to use. The pellet was suspended in cold 50 mM Tris-HCl buffer comprising 10 mM EDTA (pH 7.4) and was homogenized with a Polytron (Kinematica AG, Basel, Switzerland) for 20-30 sec at 12.000 rpm. After centrifugation at 48.000×g for 30 min at 4° C., the pellet was resuspended in cold 10 mM Tris-HCl buffer comprising 0.1 mM EDTA (pH 7.4), homogenized, and centrifuged as above. This pellet was further resuspended in a smaller volume of ice cold 10 mM Tris-HCl buffer comprising 0.1 mM EDTA (pH 7.4) and homogenized with a Polytron for 20-30 sec at 12.000 rpm. The protein content of this homogenate was determined with the Bio-Rad (Bradford) Protein Assay (Biorad Laboratories GmbH, München, Germany) according to the instructions of the manufacturer using gamma globulin as the standard. This homogenate was stored at −80° C. in aliquots and thawed immediately prior to use.

Radioligand Binding Assay

Aliquots of membrane preparations were thawed at RT, resuspended in assay buffer (D$_2$, D$_3$: 50 mM Tris-HCl, 120 mM NaCl, 5 mM MgCl$_2$, 1 mM EDTA, 5 mM KCl, 1.5 mM CaCl$_2$, pH=7.4; 5-HT$_{2A}$: 50 mM Tris-HCl, 10 mM MgCl$_2$, 1 mM EGTA, pH=7.4), homogenized with a Polytron for 20-30 sec at 12.000 rpm and adjusted to a final concentration of approximately 7.5 µg protein/well (D$_2$, D$_3$) and 15 µg protein/well (5-HT$_{2A}$), respectively.

The binding affinity (K$_i$) of the compounds was determined using radioligand binding. Membranes were incubated in a total volume of 200 µl with a fixed concentration of radioligand (final concentration approximately 0.7 nM [$^3$H]-spiperone for D$_2$, 0.5 nM [$^3$H]-spiperone for D$_3$, and 1.1 nM [$^3$H]-ketanserin for 5-HT$_{2A}$) and ten concentrations of test compound in ranging between 10 µM-0.1 nM for 1 h at RT. At the end of the incubation, the reaction mixtures were filtered on to unifilter 96-well white microplates with bonded GF/C filters (Packard BioScience, Zürich, Switzerland; preincubated for 1 h in 0.1% polyethylenimine (PEI) in assay buffer) with a Filtermate 196 harvester (Packard BioScience) and washed 3 times with cold assay buffer. The nonspecific binding was determined with equally composed reaction mixtures in the presence of 10 µM unlabelled spiperone. Per well 45 µl of Microscint 40 (Perkin Elmer, Schwerzenbach, Switzerland) was added, plates for sealed, shaken for 20 min and counted for 3 min on a Topcount Microplate Scintillation Counter (Can berra Packard SA, Zürich, Switzerland) with quenching correction.

Data Calculation

The CPM value for each duplicate of a concentration of competing compound was averaged (y1), then the % specific binding was calculated according to the equation (((y1−nonspecific)/(total binding−non-specific))×100). Graphs were plotted with the % specific binding using XLfit, a curve fitting program that iteratively plots the data using Levenberg-Marquardt algorithm. The single site competition analysis equation used was y=A+((B−A)/(1+((x/C)D))), where y is the % specific binding, A is the minimum y, B is the maximum y, C is the IC$_{50}$, x is the log 10 of the concentration of the competing compound and D is the slope of the curve (the Hill Coefficient). From these curves the IC$_{50}$ (inhibition concentration at which 50% specific binding of the radioligand was displaced) and Hill coefficient were determined. The affinity constant (K) was calculated using the Cheng-Prusoff equation K$_i$=(IC$_{50}$/1+([L]/K$_d$), where [L] is the concentration of radioligand and K$_d$ is the dissociation constant of the radioligand at the receptor as determined by the saturation isotherm.

The compounds of the present invention are selective dual modulators of the 5-HT$_{2A}$ and D$_3$ receptors as is shown in table 1 below. Examples were tested in the above assay and found to have K$_i$ 5-HT$_{2A}$ values of about 0.1 nM to about 1 µM and K$_i$ D$_3$ values of about 0.1 nM to about 1 µM. Particular compounds of formula (I) were found to have K$_i$ 5-HT$_{2A}$ values of about 1 nM to about 100 nM and K$_i$ D$_3$ values of about 1 nM to about 200 nM. Most particular compounds of formula (I) were found to have $K_i$ 5-$HT_{2A}$ values of about 1 nM to about 25 nM and $K_i$ $D_3$ values of about 1 nM to about 20 nM.

Particular compounds of formula (I) were found to bind more selectively to 5-$HT_{2A}$ receptor than $D_2$ receptor by a factor of 5 or more, more particularly 10 or more, most particularly 25 or more. Particular compounds of formula (I) were found to bind more selectively to $D_3$ receptor than $D_2$ receptor by a factor of 5 or more, more particularly 10 or more, most particularly 25 or more.

TABLE 1

Binding affinities to HEK293 EBNA cells expressing human (h) receptors of representative examples.

| Ex. | $D_2$ $K_i$ [nM] | $D_3$ $K_i$ [nM] | 5-$HT_{2a}$ $K_i$ [nM] |
|---|---|---|---|
| 1 | 486 | 18.3 | 9.1 |
| 2 | 802 | 28.8 | 6.4 |
| 3 | 1538 | 54.6 | 8.8 |
| 4 | 780 | 11.8 | 6.5 |
| 5 | 1347 | 24 | 8.1 |
| 6 | 959 | 19.9 | 10.3 |
| 7 | 1360 | 43 | 5.6 |
| 8 | 1158 | 77.2 | 4.4 |
| 9 | 1463 | 32.7 | 5.6 |
| 10 | 683 | 30.3 | 6.1 |
| 11 | 515 | 55.7 | 2.9 |
| 12 | 996 | 150 | 7.4 |
| 13 | 261 | 21.8 | 4.4 |
| 14 | 866 | 34.1 | 6.8 |
| 15 | 119 | 1.9 | 3.3 |
| 16 | 780 | 30.6 | 8.5 |
| 17 | 539 | 33 | 5.3 |
| 18 | 163 | 1.6 | 2.6 |
| 19 | 305 | 1.9 | 3.5 |
| 20 | 302 | 3 | 2.5 |
| 21 | 271 | 3.6 | 3.7 |
| 22 | 220 | 3.2 | 2.2 |
| 23 | 144 | 2.7 | 3 |
| 24 | 992 | 3.6 | 1.7 |
| 25 | 234 | 2.7 | 4.9 |
| 26 | 246 | 3 | 4.3 |
| 27 | 218 | 1.4 | 1.4 |
| 28 | 392 | 6 | 4 |
| 29 | 461 | 23.2 | 5.3 |
| 30 | 265 | 4.3 | 2.9 |
| 31 | 217 | 4.3 | 2.9 |
| 32 | 770.1 | 12.7 | 22.9 |
| 33 | 503.5 | 38.2 | 5.9 |
| 34 | 869 | 24.9 | 20.1 |
| 35 | 1488 | 17.4 | 24.1 |
| 36 | 812.7 | 9.7 | 13.3 |
| 37 | 1471.4 | 19.6 | 9.7 |
| 38 | 1545.4 | 45.4 | 11 |
| 39 | 1018.3 | 9.8 | 16.1 |
| 40 | 1568 | 15.9 | 12.2 |
| 41 | 733.5 | 11.5 | 35.7 |
| 42 | 609.5 | 18.2 | 9.9 |
| 43 | 1044 | 120 | 6.3 |
| 44 | 481.2 | 7.66 | 7.63 |
| 45 | 341.9 | 10.7 | 11.1 |
| 46 | 289.2 | 13.25 | 14.8 |
| 47 | 871.2 | 57 | 18.8 |
| 48 | 1269.5 | 31.6 | 21.7 |
| 49 | 1093.5 | 22 | 17.6 |
| 50 | 240 | 6.72 | 39.4 |
| 51 | 586.8 | 5.07 | 13.7 |
| 52 | 555 | 15.7 | 10.1 |
| 53 | 766.8 | 28.8 | 6.37 |
| 54 | 506.5 | 51.4 | 12.6 |
| 55 | 475 | 45.3 | 6.14 |
| 56 | 5340 | 44.3 | 19.2 |
| 57 | 867.1 | 16.9 | 4.52 |
| 58 | 592.9 | 27.1 | 5.92 |
| 59 | 702.5 | 7.74 | 15.7 |
| 60 | 687.5 | 6.55 | 11 |
| 61 | 1124 | 18.7 | 11.8 |
| 62 | 547.5 | 10.7 | 3.62 |
| 63 | 485.6 | 18.5 | 11.1 |
| 64 | 1262.8 | 24.2 | 16.7 |
| 65 | 2451.9 | 24.1 | 14.9 |
| 66 | 781.5 | 24.9 | 11.5 |
| 67 | 1461 | 24.3 | 8.15 |
| 68 | 914.7 | 27.1 | 14.6 |
| 69 | 857.9 | 18.1 | 24.9 |
| 70 | 523.9 | 59.2 | 9.4 |
| 71 | 654.8 | 10.9 | 15.7 |
| 72 | 444.2 | 17 | 16.2 |
| 73 | 602.7 | 8.92 | 13.3 |
| 74 | 438.3 | 23.8 | 17.3 |
| 75 | 705.1 | 16.6 | 10.2 |
| 76 | 709.4 | 25.4 | 13.2 |
| 77 | 754.6 | 12.1 | 11 |
| 78 | 322.5 | 92.8 | 28.7 |
| 79 | 773.3 | 47.3 | 19.2 |
| 80 | 198.4 | 15.4 | 16.2 |
| 81 | 945.4 | 12.9 | 22.8 |
| 82 | 425.6 | 17.2 | 12.2 |
| 83 | 837.2 | 28 | 23.5 |
| 84 | 1304.6 | 4.01 | 15.2 |
| 85 | 396.8 | 31.1 | 15.7 |
| 86 | 2562.7 | 37.6 | 23.9 |
| 87 | 999.7 | 21.6 | 25 |
| 88 | 731.8 | 19.7 | 33.1 |
| 89 | 887.4 | 20 | 30 |
| 90 | 1291.7 | 19.4 | 22.4 |
| 91 | 926.5 | 14.2 | 22.5 |
| 92 | 828.3 | 15.4 | 23.1 |
| 93 | 1277.1 | 22.7 | 24.6 |
| 94 | 1143.6 | 19.2 | 24.7 |
| 95 | 1253.7 | 20 | 29.6 |
| 96 | 248.8 | 4.64 | 75.2 |
| 97 | 274.6 | 14.2 | 25.5 |
| 98 | 640.6 | 9.45 | 75.9 |
| 99 | 429.7 | 4.8 | 86.9 |
| 100 | 915 | 7.58 | 215 |
| 101 | 1950 | 34.6 | 58.5 |
| 102 | 1935 | 18.7 | 193.4 |
| 103 | 1486 | 11.8 | 255 |
| 104 | 1461 | 21.5 | 13.7 |
| 105 | 1126 | 72.7 | 5.67 |
| 106 | 2718 | 38 | 11.7 |
| 107 | 2471 | 30 | 12 |
| 108 | 2308 | 48.2 | 67.5 |
| 109 | 4510 | 98.7 | 19.7 |
| 110 | 2951 | 69.4 | 44 |
| 111 | 3564 | 46.8 | 37 |
| 112 | 842.6 | 37.9 | 11.4 |
| 113 | 1384.9 | 19.3 | 15.7 |
| 114 | 2365.4 | 68 | 18.1 |
| 115 | 516 | 33.8 | 9.46 |
| 116 | 312.6 | 52.1 | 15.5 |
| 117 | 381.2 | 28 | 13 |
| 118 | 179.5 | 14.7 | 4.51 |
| 119 | 998.4 | 44.7 | 15.6 |
| 120 | 222.9 | 16.1 | 12.3 |
| 121 | 3372 | 21.8 | 17.6 |
| 122 | 3042 | 18.6 | 33.7 |
| 123 | 958.6 | 131.2 | 9.8 |
| 124 | 1265 | 194.6 | 7.82 |
| 125 | 116.6 | 14.4 | 16.6 |
| 126 | 478 | 44.3 | 35.9 |
| 127 | 2147 | 19.5 | 48.9 |
| 128 | 500.6 | 20.5 | 23.2 |
| 129 | 1308.9 | 14.9 | 27.8 |
| 130 | 506 | 119.4 | 18.4 |
| 131 | 1663 | 146.7 | 66.7 |
| 132 | 518.3 | 26.7 | 21.7 |
| 133 | 163.3 | 24.4 | 24.2 |
| 134 | 1132 | 18.6 | 23.4 |

TABLE 1-continued

Binding affinities to HEK293 EBNA cells expressing human (h) receptors of representative examples.

| Ex. | $D_2$ $K_i$ [nM] | $D_3$ $K_i$ [nM] | $5\text{-}HT_{2a}$ $K_i$ [nM] |
|---|---|---|---|
| 135 | 680.5 | 109.3 | 7 |
| 136 | 3161 | 69.5 | 41.4 |
| 137 | 788.5 | 252.5 | 20.1 |
| 138 | 242.6 | 15.5 | 70.5 |
| 139 | 801.3 | 40.6 | 30.4 |
| 140 | 842.7 | 44.4 | 42 |
| 141 | 408.6 | 25.8 | 22.5 |

The invention claimed is:

1. A compound of formula (I)

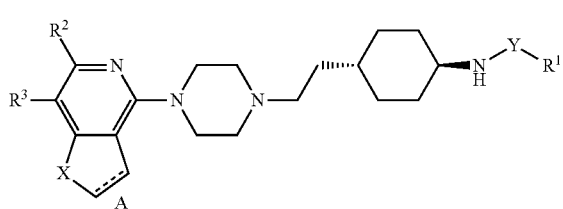

wherein
X is O or S;
Y is —C(O)— or —S(O)$_2$—;
A is a single bond or double bond,
  with the proviso that when X is S then A is a double bond;
$R^1$ is hydrogen, $C_{1-7}$ alkyl, $C_{1-7}$ haloalkyl, $C_{2-7}$ alkenyl, $C_{2-7}$ alkynyl, cycloalkyl, heterocycloalkyl, aryl, aryl annellated to heterocycloalkyl, heteroaryl, or —N($R^6$)$_2$, wherein $C_{1-7}$ alkyl, $C_{1-7}$ haloalkyl, $C_{2-7}$ alkenyl, $C_{2-7}$ alkynyl are optionally substituted by one to three substituents selected independently from the group consisting of cyano, cycloalkyl, heterocycloalkyl, aryl, aryl annellated to heterocycloalkyl, heteroaryl, —C(O)N($R^6$)$_2$, —N($R^6$)$_2$, —NH(CO)—$C_{1-7}$ alkyl, hydroxy, $C_{1-7}$ alkoxy, $C_{1-7}$ haloalkoxy, oxo, and —S(O)$_2R^7$, and wherein cycloalkyl, heterocycloalkyl, aryl, aryl annellated to heterocycloalkyl and heteroaryl are optionally substituted by one to three independent $R^4$;
$R^2$ and $R^3$ are each independently hydrogen, halogen, $C_{1-7}$ alkyl, $C_{1-7}$ haloalkyl, hydroxy, $C_{1-7}$ alkoxy or $C_{1-7}$ haloalkoxy;
$R^4$ is halogen, cyano, $C_{1-7}$ alkyl, $C_{1-7}$ haloalkyl, cycloalkyl, heterocycloalkyl, aryl, aryl annellated to heterocycloalkyl, heteroaryl, —C(O)N($R^6$)$_2$, —N($R^6$)$_2$, —NH(CO)—$C_{1-7}$ alkyl, hydroxy, $C_{1-7}$ alkoxy, $C_{1-7}$ haloalkoxy, oxo, —S(O)$_2R^7$, or $C_{1-7}$ alkyl substituted by one to three substituents selected independently from the group consisting of cyano, hydroxy, $C_{1-7}$ alkoxy, and $C_{1-7}$ haloalkoxy, wherein cycloalkyl, heterocycloalkyl, aryl, and heteroaryl are optionally substituted by one to three independent $R^5$;
$R^5$ is halogen, cyano, $C_{1-7}$ alkyl, $C_{1-7}$ haloalkyl, hydroxy, $C_{1-7}$ alkoxy, $C_{1-7}$ haloalkoxy, or oxo;
$R^6$ is hydrogen or $C_{1-7}$ alkyl;
$R^7$ is hydrogen, $C_{1-7}$ alkyl, or aryl, wherein aryl is optionally substituted by one to three independent $R^5$;
or a pharmaceutically acceptable salt or ester thereof.

2. The compound of claim 1, wherein X is O and A is a single bond.

3. The compound of claim 1, wherein X is O and A is a double bond.

4. The compound of claim 1, wherein X is S and A is a double bond.

5. The compound of claim 2, wherein X is O, A is a single bond and Y is —C(O)—.

6. The compound of claim 1, wherein
$R^1$ is hydrogen, $C_{1-7}$ alkyl, $C_{1-7}$ haloalkyl, $C_{2-7}$ alkenyl, $C_{2-7}$ alkynyl, cycloalkyl, heterocycloalkyl, aryl, aryl annellated to heterocycloalkyl, heteroaryl, or —N($R^6$)$_2$, wherein $C_{1-7}$ alkyl, and $C_{1-7}$ haloalkyl are optionally substituted by one to three substituents selected independently from the group consisting of cyano, cycloalkyl, heterocycloalkyl, aryl annellated to heterocycloalkyl, heteroaryl, —C(O)N($R^6$)$_2$, hydroxy, $C_{1-7}$ alkoxy, $C_{1-7}$ haloalkoxy, and
—S(O)$_2R^7$, and wherein cycloalkyl, heterocycloalkyl, aryl, and heteroaryl are optionally substituted by one to three independent $R^4$.

7. The compound of claim 1, wherein $R^1$ is methyl; methyl substituted by a substituent selected from the group consisting of cyano, cyclopropyl, cyclobutyl, hydroxy-cyclobutyl, methoxy-cyclopentyl, hydroxy-cyclohexyl, methoxy-cyclohexyl, oxetanyl, tetrahydrofuranyl, hydroxy-tetrahydrofuranyl, tetrahydropyranyl, dioxanyl, benzodioxolyl, methylisoxazolyl, benzoisoxazolyl, hydroxy, methoxy, ethoxy, and —S(O)$_2$-methyl; ethyl; ethyl substituted with a substituent selected from the group consisting of hydroxy, methoxy, and C(O)—N(methyl)$_2$; n-propyl; n-propyl substituted by methoxy; iso-propyl; iso-propyl substituted by hydroxy; n-butyl; n-butyl substituted by hydroxy; iso-butyl; iso-butyl substituted by hydroxy; tert-butyl; iso-pentyl; tert-pentyl; trifluoro-methyl; trifluoro-ethyl; trifluoro-ethyl substituted by hydroxy; trifluoro-n-propyl; trifluoro-n-propyl substituted by hydroxy; (E)-butenyl; iso-butenyl; propynyl; cyclopropyl; cyclopropyl substituted by fluoro; cyclopropyl substituted by hydroxy; cyclobutyl; cyclobutyl substituted by hydroxy; cyclohexyl; cyclohexyl substituted by methyl and hydroxy; tetrahydrofuranyl; tetrahydropyranyl; phenyl; phenyl substituted by a substituent selected from the group consisting of fluoro, chloro, cyano, methyl, tert-butyl, tert-butoxy, piperidinyl, methyl-piperazinyl, morpholinyl, dioxothiomorpholinyl, phenyl, pyrrolyl, pyrazolyl, methyloxadiazolyl, and pyridinyl; benzodioxolyl; thienyl; thienyl substituted by —S(O)$_2$-methyl; isoxazolyl; methylisoxazolyl; pyridinyl; methyl-pyridinyl; morpholinyl-pyridinyl; pyrazinyl; morpholinyl-pyrazinyl; or quinolinyl.

8. The compound of claim 7, wherein $R^1$ is methyl; methyl substituted with a substituent selected from the group consisting of cyano, cyclopropyl, hydroxy, dioxanyl and —S(O)$_2$-methyl; ethyl; ethyl substituted with fluoro; iso-propyl; cyclopropyl; cyclobutyl; or tetrahydrofuranyl.

9. The compound of claim 1, wherein $R^2$ is hydrogen.

10. The compound of claim 1, wherein $R^3$ is hydrogen or methyl.

11. The compound of claim 1, wherein $R^3$ is hydrogen.

12. The compound of claim 1, wherein $R^4$ is halogen, cyano, $C_{1-7}$ alkyl, $C_{1-7}$ haloalkyl, cycloalkyl, heterocycloalkyl, hydroxy, $C_{1-7}$ alkoxy, aryl, aryl annellated to heterocycloalkyl, heteroaryl or —S(O)$_2R^7$, wherein cycloalkyl, heterocycloalkyl, aryl, aryl annellated to heterocycloalkyl and heteroaryl, are optionally substituted by one to three independent $R^5$.

13. The compound of claim 1, wherein $R^4$ is fluoro, chloro, cyano, methyl, trifluoro-methyl, tert-butyl, cyclopropyl, cyclobutyl, cyclopentyl substituted by methoxy, cyclohexyl substituted by hydroxy or methoxy, oxetanyl, tetrahydrofuranyl, tetrahydropyranyl, piperidinyl, piperazinyl, morpholinyl, thiomorpholinyl, thiomorpholinyl substituted by oxo, dioxanyl, phenyl, benzodioxolyl, pyrrolyl, pyrazolyl, oxadiazolyl, methyl-oxadiazolyl, pyridinyl, hydroxy, methoxy, ethoxy, tert-butoxy, or —S(O)$_2$-methyl.

14. The compound of claim 1, wherein $R^4$ is fluoro, cyano, cyclopropyl, dioxanyl, morpholinyl, phenyl, hydroxy, or —S(O)$_2$-methyl.

15. The compound of claim 1, wherein $R^5$ is halogen, hydroxy, $C_{1-7}$ alkyl, $C_{1-7}$ alkoxy, or oxo.

16. The compound of claim 15, wherein $R^5$ is fluoro, hydroxy, methyl, methoxy, or oxo.

17. The compound of claim 1, wherein $R^6$ is $C_{1-7}$ alkyl.

18. The compound of claim 1, wherein $R^6$ is methyl.

19. The compound of claim 1, wherein $R^7$ is $C_{1-7}$ alkyl.

20. The compound of claim 19, wherein $R^7$ is methyl.

21. The compound of claim 1, selected from the group consisting of:

N-{trans-4-[2-(4-Furo[3,2-c]pyridin-4-yl-piperazin-1-yl)-ethyl]-cyclohexyl}-acetamide;

N-{trans-4-[2-(4-Furo[3,2-c]pyridin-4-yl-piperazin-1-yl)-ethyl]-cyclohexyl}-2-(trans-3-methoxy-cyclopentyl)-acetamide;

N-{trans-4-[2-(4-Furo[3,2-c]pyridin-4-yl-piperazin-1-yl)-ethyl]-cyclohexyl}-2-(trans-4-hydroxy-cyclohexyl)-acetamide;

N-{trans-4-[2-(4-Furo[3,2-c]pyridin-4-yl-piperazin-1-yl)-ethyl]-cyclohexyl}-propionamide;

N-{trans-4-[2-(4-Furo[3,2-c]pyridin-4-yl-piperazin-1-yl)-ethyl]-cyclohexyl}-3-methoxy-propionamide;

N-{trans-4-[2-(4-Furo[3,2-c]pyridin-4-yl-piperazin-1-yl)-ethyl]-cyclohexyl}-3-hydroxy-propionamide;

N-{trans-4-[2-(4-Furo[3,2-c]pyridin-4-yl-piperazin-1-yl)-ethyl]-cyclohexyl}-2-hydroxy-acetamide;

N-{trans-4-[2-(4-Furo[3,2-c]pyridin-4-yl-piperazin-1-yl)-ethyl]-cyclohexyl}-2-methoxy-acetamide;

N-{trans-4-[2-(4-Furo[3,2-c]pyridin-4-yl-piperazin-1-yl)-ethyl]-cyclohexyl}-2-(trans-4-methoxy-cyclohexyl)-acetamide; and N-{trans-4-[2-(4-Furo[3,2-c]pyridin-4-yl-piperazin-1-yl)-ethyl]-cyclohexyl}-2-(tetrahydro-pyran-4-yl)-acetamide or a pharmaceutically acceptable salt or ester thereof.

22. The compound of claim 1, selected from the group consisting of:

Tetrahydro-pyran-4-carboxylic acid {trans-4-[2-(4-furo[3,2-c]pyridin-4-yl-piperazin-1-yl)-ethyl]-cyclohexyl}-amide;

2-Ethoxy-N-{trans-4-[2-(4-furo[3,2-c]pyridin-4-yl-piperazin-1-yl)-ethyl]-cyclohexyl}-acetamide;

Cyclopropanecarboxylic acid {trans-4-[2-(4-furo[3,2-c]pyridin-4-yl-piperazin-1-yl)-ethyl]-cyclohexyl}-amide;

N-{trans-4-[2-(4-Furo[3,2-c]pyridin-4-yl-piperazin-1-yl)-ethyl]-cyclohexyl}-methanesulfonamide;

N-{trans-4-[2-(4-Thieno[3,2-c]pyridin-4-yl-piperazin-1-yl)-ethyl]-cyclohexyl}-acetamide;

Ethanesulfonic acid {trans-4-[2-(4-furo[3,2-c]pyridin-4-yl-piperazin-1-yl)-ethyl]-cyclohexyl}-amide;

N'-(trans-4{[4-(furo[3,2-c]pyridin-4-yl)-piperazin-1-yl]-ethyl}cyclohexyl)-N,N-dimethylsulfamide;

N-{trans-4-[2-(4-Thieno[3,2-c]pyridin-4-yl-piperazin-1-yl)-ethyl]-cyclohexyl}-propionamide;

3-Methoxy-N-{trans-4-[2-(4-thieno[3,2-c]pyridin-4-yl-piperazin-1-yl)-ethyl]-cyclohexyl}-propionamide; and 2-(trans-4-Methoxy-cyclohexyl)-N-{trans-4-[2-(4-thieno[3,2-c]pyridin-4-yl-piperazin-1-yl)-ethyl]-cyclohexyl}-acetamide or a pharmaceutically acceptable salt thereof.

23. The compound of claim 1, selected from the group consisting of:

2-(trans-3-Methoxy-cyclopentyl)-N-{trans-4-[2-(4-thieno[3,2-c]pyridin-4-yl-piperazin-1-yl)-ethyl]-cyclohexyl}-acetamide;

2-Methoxy-N-{trans-4-[2-(4-thieno[3,2-c]pyridin-4-yl-piperazin-1-yl)-ethyl]-cyclohexyl}-acetamide;

2-(Tetrahydro-pyran-4-yl)-N-{trans-4-[2-(4-thieno[3,2-c]pyridin-4-yl-piperazin-1-yl)-ethyl]-cyclohexyl}-acetamide;

Tetrahydro-pyran-4-carboxylic acid {trans-4-[2-(4-thieno[3,2-c]pyridin-4-yl-piperazin-1-yl)-ethyl]-cyclohexyl}-amide;

2-((1R,3R)-3-Methoxy-cyclopentyl)-N-{trans-4-[2-(4-thieno[3,2-c]pyridin-4-yl-piperazin-1-yl)-ethyl]-cyclohexyl}-acetamide;

2-((1S,3S)-3-Methoxy-cyclopentyl)-N-{trans-4-[2-(4-thieno[3,2-c]pyridin-4-yl-piperazin-1-yl)-ethyl]-cyclohexyl}-acetamide;

2-Hydroxy-N-{trans-4-[2-(4-thieno[3,2-c]pyridin-4-yl-piperazin-1-yl)-ethyl]-cyclohexyl}-acetamide;

2-(trans-4-Hydroxy-cyclohexyl)-N-{trans-4-[2-(4-thieno[3,2-c]pyridin-4-yl-piperazin-1-yl)-ethyl]-cyclohexyl}-acetamide;

Quinoline-4-carboxylic acid {trans-4-[2-(4-furo[3,2-c]pyridin-4-yl-piperazin-1-yl)-ethyl]-cyclohexyl}-amide; and N-{trans-4-[2-(4-Thieno[3,2-c]pyridin-4-yl-piperazin-1-yl)-ethyl]-cyclohexyl}-methanesulfonamide or a pharmaceutically acceptable salt or ester thereof.

24. The compound of claim 1, selected from the group consisting of:

Ethanesulfonic acid {trans-4-[2-(4-thieno[3,2-c]pyridin-4-yl-piperazin-1-yl)-ethyl]-cyclohexyl}-amide;

trans-N-(4-{2-[4-(2,3-Dihydro-furo[3,2-c]pyridin-4-yl)-piperazin-1-yl]-ethyl}-cyclohexyl)-acetamide;

trans-N-(4-{2-[4-(2,3-Dihydrofuro[3,2-c]pyridin-4-yl)-piperazin-1-yl]-ethyl}-cyclohexyl)-tetrahydro-2H-pyran-4-carboxamide;

trans-N-(4-{2-[4-(2,3-Dihydrofuro[3,2-c]pyridin-4-yl)-piperazin-1-yl]-ethyl}-cyclohexyl)-2-(tetrahydro-2H-pyran-4-yl)-acetamide;

trans-N-(4-{2-[4-(2,3-Dihydrofuro[3,2-c]pyridin-4-yl)-piperazin-1-yl]-ethyl}-cyclohexyl)-3-methoxypropanamide;

trans-N-(4-{2-[4-(2,3-Dihydrofuro[3,2-c]pyridin-4-yl)-piperazin-1-yl]-ethyl}-cyclohexyl)-propionamide;

trans-N-(4-{2-[4-(2,3-Dihydrofuro[3,2-c]pyridin-4-yl)-piperazin-1-yl]-ethyl}-cyclohexyl)-2-(rac-1,4-dioxan-2-yl)-acetamide;

trans-N-(4-{2-[4-(2,3-Dihydrofuro[3,2-c]pyridin-4-yl)-piperazin-1-yl]-ethyl}-cyclohexyl)-2-methoxyacetamide;

trans-N-(4-{2-[4-(2,3-Dihydrofuro[3,2-c]pyridin-4-yl)-piperazin-1-yl]-ethyl}-cyclohexyl)-methylsulfonyl-acetamide; and trans-N-(4-{2-[4-(2,3-Dihydrofuro[3,2-c]pyridin-4-yl)-piperazin-1-yl]-ethyl}-cyclohexyl)-hydroxyacetamide or a pharmaceutically acceptable salt thereof.

25. The compound of claim 1, selected from the group consisting of:

trans-N-(4-{2-[4-(2,3-Dihydrofuro[3,2-c]pyridin-4-yl)-piperazin-1-yl]-ethyl}-cyclohexyl)-3-hydroxypropanamide;

trans-N-(4-{2-[4-(2,3-Dihydrofuro[3,2-c]pyridin-4-yl)-piperazin-1-yl]-ethyl}-cyclohexyl)-rac-tetrahydrofuran-3-carboxamide;

trans-N-(4-{2-[4-(2,3-Dihydrofuro[3,2-c]pyridin-4-yl)-piperazin-1-yl]-ethyl}-cyclohexyl)-rac-tetrahydrofuran-2-carboxamide;

trans-N-(4-{2-[4-(2,3-Dihydro-furo[3,2-c]pyridin-4-yl)-piperazin-1-yl]-ethyl}-cyclohexyl)-benzamide;

trans-N-(4-{2-[4-(2,3-Dihydro-furo[3,2-c]pyridin-4-yl)-piperazin-1-yl]-ethyl}-cyclohexyl)-4-fluoro-benzamide;

trans-4-Chloro-N-(4-{2-[4-(2,3-dihydro-furo[3,2-c]pyridin-4-yl)-piperazin-1-yl]-ethyl}-cyclohexyl)-benzamide;

trans-N-(4-{2-[4-(2,3-Dihydro-furo[3,2-c]pyridin-4-yl)-piperazin-1-yl]-ethyl}-cyclohexyl)-4-trifluoromethyl-benzamide;

trans-N-(4-{2-[4-(2,3-Dihydro-furo[3,2-c]pyridin-4-yl)-piperazin-1-yl]-ethyl}-cyclohexyl)-methanesulfonamide;

Ethanesulfonic acid trans-(4-{2-[4-(2,3-dihydro-furo[3,2-c]pyridin-4-yl)-piperazin-1-yl]-ethyl}-cyclohexyl)-amide; and trans-N-(4-{2-[4-(2,3-Dihydro-furo[3,2-c]pyridin-4-yl)-piperazin-1-yl]-ethyl}-cyclohexyl)-4-fluoro-benzenesulfonamide or a pharmaceutically acceptable salt thereof.

26. The compound of claim 1, selected from the group consisting of:

trans-2-Cyclopropyl-N-(4-{2-[4-(2,3-dihydro-furo[3,2-c]pyridin-4-yl)-piperazin-1-yl]-ethyl}-cyclohexyl)-acetamide;

Cyclobutanecarboxylic acid trans-(4-{2-[4-(2,3-dihydro-furo[3,2-c]pyridin-4-yl)-piperazin-1-yl]-ethyl}-cyclohexyl)-amide;

rac-Tetrahydro-pyran-3-carboxylic acid trans-(4-{2-[4-(2,3-dihydro-furo[3,2-c]pyridin-4-yl)-piperazin-1-yl]-ethyl}-cyclohexyl)-amide;

trans-4-Hydroxy-4-methyl-cyclohexanecarboxylic acid trans-(4-{2-[4-(2,3-dihydro-furo[3,2-c]pyridin-4-yl)-piperazin-1-yl]-ethyl}-cyclohexyl)-amide;

cis-4-Hydroxy-4-methyl-cyclohexanecarboxylic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-4-piperidin-1-yl-benzamide;

trans-N-(4-{2-[4-(2,3-Dihydro-furo[3,2-c]pyridin-4-yl)-piperazin-1-yl]-ethyl}-cyclohexyl)-4-morpholin-4-yl-benzamide;

1-Hydroxy-cyclopropanecarboxylic acid trans-(4-{2-[4-(2,3-dihydro-furo[3,2-c]pyridin-4-yl)-piperazin-1-yl]-ethyl}-cyclohexyl)-amide;

trans-2-Cyano-N-(4-{2-[4-(2,3-dihydro-furo[3,2-c]pyridin-4-yl)-piperazin-1-yl]-ethyl}-cyclohexyl)-acetamide; and trans-N-(4-{2-[4-(2,3-Dihydro-furo[3,2-c]pyridin-4-yl)-piperazin-1-yl]-ethyl}-cyclohexyl)-3,3,3-trifluoro-propionamide or a pharmaceutically acceptable salt or ester thereof.

27. The compound of claim 1, selected from the group consisting of:

trans-N-(4-{2-[4-(2,3-Dihydro-furo[3,2-c]pyridin-4-yl)-piperazin-1-yl]-ethyl}-cyclohexyl)-2-(R)-[1,4]dioxan-2-yl-acetamide;

Quinoline-4-carboxylic acid trans-(4-{2-[4-(2,3-dihydro-furo[3,2-c]pyridin-4-yl)-piperazin-1-yl]-ethyl}-cyclohexyl)-amide;

Cyclopropanecarboxylic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-2-rac-(tetrahydro-furan-2-yl)-acetamide;

trans-N-(4-{2-[4-(2,3-Dihydro-furo[3,2-c]pyridin-4-yl)-piperazin-1-yl]-ethyl}-cyclohexyl)-2-trans-(4-methoxy-cyclohexyl)-acetamide;

N'-trans-(4-{2-[4-(2,3-dihydro-furo[3,2-c]pyridin-4-yl)-piperazin-1-yl]-ethyl}-cyclohexyl)-N,N-dimethyl-sulfamide;

trans-N-(4-{2-[4-(2,3-Dihydro-furo[3,2-c]pyridin-4-yl)-piperazin-1-yl]-ethyl}-cyclohexyl)-2-(S)-[1,4]dioxan-2-yl-acetamide;

trans-N-(4-{2-[4-(2,3-Dihydro-furo[3,2-c]pyridin-4-yl)-piperazin-1-yl]-ethyl}-cyclohexyl)-2-(R)-(tetrahydro-furan-2-yl)-acetamide;

trans-N-(4-{2-[4-(2,3-Dihydro-furo[3,2-c]pyridin-4-yl)-piperazin-1-yl]-ethyl}-cyclohexyl)-2-(S)-(tetrahydro-furan-2-yl)-acetamide; and trans-N-(4-{2-[4-(2,3-Dihydro-furo[3,2-c]pyridin-4-yl)-piperazin-1-yl]-ethyl}-cyclohexyl)-2,2-dimethyl-propionamide or a pharmaceutically acceptable salt thereof.

28. The compound of claim 1, selected from the group consisting of:

trans-N-(4-{2-[4-(2,3-Dihydro-furo[3,2-c]pyridin-4-yl)-piperazin-1-yl]-ethyl}-cyclohexyl)-3-methyl-butyramide;

trans-N-(4-{2-[4-(2,3-Dihydro-furo[3,2-c]pyridin-4-yl)-piperazin-1-yl]-ethyl}-cyclohexyl)-3,3-dimethyl-butyramide;

trans-2-Cyclobutyl-N-(4-{2-[4-(2,3-dihydro-furo[3,2-c]pyridin-4-yl)-piperazin-1-yl]-ethyl}-cyclohexyl)-acetamide;

trans-2,2-Difluoro-cyclopropanecarboxylic acid (4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-isobutyramide;

trans-N-(4-{2-[4-(2,3-Dihydro-furo[3,2-c]pyridin-4-yl)-piperazin-1-yl]-ethyl}-cyclohexyl)-rac-2-methyl-butyramide;

trans-N-(4-{2-[4-(2,3-Dihydro-furo[3,2-c]pyridin-4-yl)-piperazin-1-yl]-ethyl}-cyclohexyl)-2-oxetan-3-yl-acetamide;

trans-3-(4-{2-[4-(2,3-Dihydro-furo[3,2-c]pyridin-4-yl)-piperazin-1-yl]-ethyl}-cyclohexyl)-1,1-dimethyl-urea;

trans-N-(4-{2-[4-(2,3-Dihydro-furo[3,2-c]pyridin-4-yl)-piperazin-1-yl]-ethyl}-cyclohexyl)-2,2,2-trifluoro-acetamide; and 3-Methyl-but-2-enoic acid trans-(4-{2-[4-(2,3-dihydro-furo[3,2-c]pyridin-4-yl)-piperazin-1-yl]-ethyl}-cyclohexyl)-amide or a pharmaceutically acceptable salt thereof.

29. The compound of claim 1, selected from the group consisting of:

(E)-Pent-3-enoic acid trans-(4-{2-[4-(2,3-dihydro-furo[3,2-c]pyridin-4-yl)-piperazin-1-yl]-ethyl}-cyclohexyl)-amide;

But-2-ynoic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-formamide;

trans-N-(4-{2-[4-(2,3-Dihydro-furo[3,2-c]pyridin-4-yl)-piperazin-1-yl]-ethyl}-cyclohexyl)-2-(3-methyl-isoxazol-5-yl)-acetamide;

3-Methyl-isoxazole-5-carboxylic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-N',N'-dimethyl-succinamide;

trans-N-(4-{2-[4-(2,3-Dihydro-furo[3,2-c]pyridin-4-yl)-piperazin-1-yl]-ethyl}-cyclohexyl)-3-hydroxy-3-methyl-butyramide;

trans-(R)—N-(4-{2-[4-(2,3-Dihydro-furo[3,2-c]pyridin-4-yl)-piperazin-1-yl]-ethyl}-cyclohexyl)-4,4,4-trifluoro-3-hydroxy-butyramide;

(S)-3-Hydroxy-pentanoic acid trans-(4-{2-[4-(2,3-dihydro-furo[3,2-c]pyridin-4-yl)-piperazin-1-yl]-ethyl}-cyclohexyl)-amide; and trans-N-(4-{2-[4-(2,3-Dihydro-furo[3,2-c]pyridin-4-yl)-piperazin-1-yl]-ethyl}-cyclohexyl)-2-((1S,3S)-3-methoxy-cyclopentyl)-acetamide or a pharmaceutically acceptable salt or ester thereof.

30. The compound of claim 1, selected from the group consisting of:

trans-N-(4-{2-[4-(2,3-Dihydro-furo[3,2-c]pyridin-4-yl)-piperazin-1-yl]-ethyl}-cyclohexyl)-2-((S)-4-hydroxy-tetrahydro-furan-2-yl)-acetamide;

trans-N-(4-{2-[4-(2,3-Dihydro-furo[3,2-c]pyridin-4-yl)-piperazin-1-yl]-ethyl}-cyclohexyl)-butyramide;

4-Methyl-pentanoic acid trans-(4-{2-[4-(2,3-dihydro-furo[3,2-c]pyridin-4-yl)-piperazin-1-yl]-ethyl}-cyclohexyl)-amide;

Pentanoic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-4,4,4-trifluoro-butyramide;

trans-N-(4-{2-[4-(6-Methyl-furo[3,2-c]pyridin-4-yl)-piperazin-1-yl]-ethyl}-cyclohexyl)-acetamide;

trans-Tetrahydro-pyran-4-carboxylic acid (4-{2-[4-(6-methyl-furo[3,2-c]pyridin-4-yl)-piperazin-1-yl]-ethyl}-cyclohexyl)-amide;

trans-N-(4-{2-[4-(6-Methyl-furo[3,2-c]pyridin-4-yl)-piperazin-1-yl]-ethyl}-cyclohexyl)-2-(tetrahydro-pyran-4-yl)-acetamide;

trans-3-Methoxy-N-(4-{2-[4-(6-methyl-furo[3,2-c]pyridin-4-yl)-piperazin-1-yl]-ethyl}-cyclohexyl)-propionamide; and trans-N-(4-{2-[4-(6-Methyl-2,3-dihydro-furo[3,2-c]pyridin-4-yl)-piperazin-1-yl]-ethyl}-cyclohexyl)-acetamide or a pharmaceutically acceptable salt thereof.

31. The compound of claim 1, selected from the group consisting of:

Tetrahydro-pyran-4-carboxylic acid trans-(4-{2-[4-(6-methyl-2,3-dihydro-furo[3,2-c]pyridin-4-yl)-piperazin-1-yl]-ethyl}-cyclohexyl)-amide;

trans-N-(4-{2-[4-(6-Methyl-2,3-dihydro-furo[3,2-c]pyridin-4-yl)-piperazin-1-yl]-ethyl}-cyclohexyl)-2-(tetrahydro-pyran-4-yl)-acetamide;

trans-3-Methoxy-N-(4-{2-[4-(6-methyl-2,3-dihydro-furo[3,2-c]pyridin-4-yl)-piperazin-1-yl]-ethyl}-cyclohexyl)-propionamide;

trans-N-(4-{2-[4-(7-Methyl-furo[3,2-c]pyridin-4-yl)-piperazin-1-yl]-ethyl}-cyclohexyl)-acetamide;

trans-Tetrahydro-pyran-4-carboxylic acid (4-{2-[4-(7-methyl-furo[3,2-c]pyridin-4-yl)-piperazin-1-yl]-ethyl}-cyclohexyl)-amide;

trans-N-(4-{2-[4-(7-Methyl-furo[3,2-c]pyridin-4-yl)-piperazin-1-yl]-ethyl}-cyclohexyl)-2-(tetrahydro-pyran-4-yl)-acetamide;

trans-3-Methoxy-N-(4-{2-[4-(7-methyl-furo[3,2-c]pyridin-4-yl)-piperazin-1-yl]-ethyl}-cyclohexyl)-propionamide;

trans-N-(4-{2-[4-(7-Methyl-2,3-dihydro-furo[3,2-c]pyridin-4-yl)-piperazin-1-yl]-ethyl}-cyclohexyl)-acetamide;

Tetrahydro-pyran-4-carboxylic acid trans-(4-{2-[4-(7-methyl-2,3-dihydro-furo[3,2-c]pyridin-4-yl)-piperazin-1-yl]-ethyl}-cyclohexyl)-amide; and trans-N-(4-{2-[4-(7-Methyl-2,3-dihydro-furo[3,2-c]pyridin-4-yl)-piperazin-1-yl]-ethyl}-cyclohexyl)-2-(tetrahydro-pyran-4-yl)-acetamide or a pharmaceutically acceptable salt thereof.

32. The compound of claim 1, selected from the group consisting of:

trans-3-Methoxy-N-(4-{2-[4-(7-methyl-2,3-dihydro-furo[3,2-c]pyridin-4-yl)-piperazin-1-yl]-ethyl}-cyclohexyl)-propionamide;

trans-(RS)—N-(4-{2-[4-(2,3-Dihydro-furo[3,2-c]pyridin-4-yl)-piperazin-1-yl]-ethyl}-cyclohexyl)-3,3,3-trifluoro-2-hydroxy-propionamide;

trans-N-(4-{2-[4-(2,3-Dihydro-furo[3,2-c]pyridin-4-yl)-piperazin-1-yl]-ethyl}-cyclohexyl)-3,3-dimethoxy-propionamide;

trans-N-(4-{2-[4-(2,3-Dihydro-furo[3,2-c]pyridin-4-yl)-piperazin-1-yl]-ethyl}-cyclohexyl)-4,4-dimethoxy-butyramide;

5-Methanesulfonyl-thiophene-2-carboxylic acid trans-(4-{2-[4-(2,3-dihydro-furo[3,2-c]pyridin-4-yl)-piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-6-methyl-nicotinamide;

trans-4-Cyano-N-(4-{2-[4-(2,3-dihydro-furo[3,2-c]pyridin-4-yl)-piperazin-1-yl]-ethyl}-cyclohexyl)-benzamide;

trans-N-(4-{2-[4-(2,3-Dihydro-furo[3,2-c]pyridin-4-yl)-piperazin-1-yl]-ethyl}-cyclohexyl)-4-(4-methyl-piperazin-1-yl)-benzamide;

trans-N-(4-{2-[4-(2,3-Dihydro-furo[3,2-c]pyridin-4-yl)-piperazin-1-yl]-ethyl}-cyclohexyl)-6-morpholin-4-yl-nicotinamide; and trans-N-(4-{2-[4-(2,3-Dihydro-furo[3,2-c]pyridin-4-yl)-piperazin-1-yl]-ethyl}-cyclohexyl)-4-pyridin-3-yl-benzamide or a pharmaceutically acceptable salt thereof.

33. The compound of claim 1, selected from the group consisting of:

Benzo[1,3]dioxole-5-carboxylic acid trans-(4-{2-[4-(2,3-dihydro-furo[3,2-c]pyridin-4-yl)-piperazin-1-yl]-ethyl}-cyclohexyl)-amide;

trans-2-Benzo[1,3]dioxol-5-yl-N-(4-{2-[4-(2,3-dihydro-furo[3,2-c]pyridin-4-yl)-piperazin-1-yl]-ethyl}-cyclohexyl)-acetamide;

1-Hydroxy-cyclobutanecarboxylic acid trans-(4-{2-[4-(2,3-dihydro-furo[3,2-c]pyridin-4-yl)piperazin-1-yl]-ethyl}-cyclohexyl)-amide;

trans-N-(4-{2-[4-(2,3-Dihydro-furo[3,2-c]pyridin-4-yl)-piperazin-1-yl]-ethyl}-cyclohexyl)-2-hydroxy-2-methyl-propionamide;

trans-N-(4-{2-[4-(2,3-Dihydro-furo[3,2-c]pyridin-4-yl)-piperazin-1-yl]-ethyl}-cyclohexyl)-4-(1,1-dioxo-1λ6-thiomorpholin-4-yl)-benzamide;

trans-N-(4-{2-[4-(2,3-Dihydro-furo[3,2-c]pyridin-4-yl)-piperazin-1-yl]-ethyl}-cyclohexyl)-4-pyrazol-1-yl-benzamide;

trans-N-(4-{2-[4-(2,3-Dihydro-furo[3,2-c]pyridin-4-yl)-piperazin-1-yl]-ethyl}-cyclohexyl)-3-(5-methyl-[1,2,4]oxadiazol-3-yl)-benzamide;

Quinoline-6-carboxylic acid trans-(4-{2-[4-(2,3-dihydro-furo[3,2-c]pyridin-4-yl)-piperazin-1-yl]-ethyl}-cyclohexyl)-amide;

trans-2-Benzo[d]isoxazol-3-yl-N-(4-{2-[4-(2,3-dihydro-furo[3,2-c]pyridin-4-yl)-piperazin-1-yl]-ethyl}-cyclohexyl)-acetamide; and 5-Morpholin-4-yl-pyrazine-2-carboxylic acid trans-(4-{2-[4-(2,3-dihydro-furo[3,2-c]pyridin-4-yl)-piperazin-1-yl]-ethyl}-cyclohexyl)-amide or a pharmaceutically acceptable salt thereof.

34. The compound of claim 1, selected from the group consisting of:

trans-4-tert-Butyl-N-(4-{2-[4-(2,3-dihydro-furo[3,2-c]pyridin-4-yl)-piperazin-1-yl]-ethyl}-cyclohexyl)-benzamide;

trans-2,4-Dichloro-N-(4-{2-[4-(2,3-dihydro-furo[3,2-c]pyridin-4-yl)-piperazin-1-yl]-ethyl}-cyclohexyl)-benzamide;

trans-N-(4-{2-[4-(2,3-Dihydro-furo[3,2-c]pyridin-4-yl)-piperazin-1-yl]-ethyl}-cyclohexyl)-4-pyrrol-1-yl-benzamide;

Biphenyl-4-carboxylic acid trans-(4-{2-[4-(2,3-dihydro-furo[3,2-c]pyridin-4-yl)-piperazin-1-yl]-ethyl}-cyclohexyl)-amide;

trans-(R)—N-(4-{2-[4-(2,3-Dihydro-furo[3,2-c]pyridin-4-yl)-piperazin-1-yl]-ethyl}-cyclohexyl)-2-methoxy-propionamide;

trans-4-tert-Butoxy-N-(4-{2-[4-(2,3-dihydro-furo[3,2-c]pyridin-4-yl)-piperazin-1-yl]-ethyl}-cyclohexyl)-benzamide;

trans-(S)—N-(4-{2-[4-(2,3-Dihydro-furo[3,2-c]pyridin-4-yl)-piperazin-1-yl]-ethyl}-cyclohexyl)-2-methoxy-propionamide;

trans-N-(4-{2-[4-(2,3-Dihydro-furo[3,2-c]pyridin-4-yl)-piperazin-1-yl]-ethyl}-cyclohexyl)-benzenesulfonamide;

trans-N-(4-{2-[4-(2,3-Dihydro-furo[3,2-c]pyridin-4-yl)-piperazin-1-yl]-ethyl}-cyclohexyl)-3-methoxy-butyramide;

(R)-3-Hydroxy-pentanoic acid trans-(4-{2-[4-(2,3-dihydro-furo[3,2-c]pyridin-4-yl)-piperazin-1-yl]-ethyl}-cyclohexyl)-amide and trans-N-(4-{2-[4-(2,3-Dihydro-furo[3,2-c]pyridin-4-yl)-piperazin-1-yl]-ethyl}-cyclohexyl)-2-(1-hydroxy-cyclobutyl)-acetamide;

or a pharmaceutically acceptable salt thereof.

35. The compound of claim 1, selected from the group consisting of:

trans-N-(4-{2-[4-(2,3-Dihydro-furo[3,2-c]pyridin-4-yl)-piperazin-1-yl]-ethyl}-cyclohexyl)-acetamide;

trans-N-(4-{2-[4-(2,3-Dihydrofuro[3,2-c]pyridin-4-yl)-piperazin-1-yl]-ethyl}-cyclohexyl)-propionamide;

trans-N-(4-{2-[4-(2,3-Dihydrofuro[3,2-c]pyridin-4-yl)-piperazin-1-yl]-ethyl}-cyclohexyl)-2-(rac-1,4-dioxan-2-yl)-acetamide;

trans-N-(4-{2-[4-(2,3-Dihydrofuro[3,2-c]pyridin-4-yl)-piperazin-1-yl]-ethyl}-cyclohexyl)-methylsulfonyl-acetamide;

trans-N-(4-{2-[4-(2,3-Dihydrofuro[3,2-c]pyridin-4-yl)-piperazin-1-yl]-ethyl}-cyclohexyl)-hydroxyacetamide;

trans-N-(4-{2-[4-(2,3-Dihydrofuro[3,2-c]pyridin-4-yl)-piperazin-1-yl]-ethyl}-cyclohexyl)-rac-tetrahydrofuran-3-carboxamide;

trans-2-Cyclopropyl-N-(4-{2-[4-(2,3-dihydro-furo[3,2-c]pyridin-4-yl)-piperazin-1-yl]-ethyl}-cyclohexyl)-acetamide;

Cyclobutanecarboxylic acid trans-(4-{2-[4-(2,3-dihydro-furo[3,2-c]pyridin-4-yl)-piperazin-1-yl]-ethyl}-cyclohexyl)-amide;

trans-2-Cyano-N-(4-{2-[4-(2,3-dihydro-furo[3,2-c]pyridin-4-yl)-piperazin-1-yl]-ethyl}-cyclohexyl)-acetamide;

trans-N-(4-{2-[4-(2,3-Dihydro-furo[3,2-c]pyridin-4-yl)-piperazin-1-yl]-ethyl}-cyclohexyl)-3,3,3-trifluoro-propionamide;

trans-N-(4-{2-[4-(2,3-Dihydro-furo[3,2-c]pyridin-4-yl)-piperazin-1-yl]-ethyl}-cyclohexyl)-2-(R)-[1,4]dioxan-2-yl-acetamide;

Cyclopropanecarboxylic acid trans-(4-{2-[4-(2,3-dihydro-furo[3,2-c]pyridin-4-yl)-piperazin-1-yl]-ethyl}-cyclohexyl)-amide; and trans-N-(4-{2-[4-(2,3-Dihydro-furo[3,2-c]pyridin-4-yl)-piperazin-1-yl]-ethyl}-cyclohexyl)-isobutyramide;

or a pharmaceutically acceptable salt thereof.

36. A pharmaceutical composition comprising a compound in accordance with claim 1 and a pharmaceutically acceptable carrier.

* * * * *